US012078646B2

United States Patent
Ge et al.

(10) Patent No.: US 12,078,646 B2
(45) Date of Patent: Sep. 3, 2024

(54) STRATEGY ENABLED BY A PHOTO-CLEAVABLE SURFACTANT FOR EXTRACELLULAR VESICLE PROTEOMICS

(71) Applicant: Wisconsin Alumni Research Foundation, Madison, WI (US)

(72) Inventors: Ying Ge, Madison, WI (US); Song Jin, Madison, WI (US); Kyle Brown, Madison, WI (US); Kevin Buck, Madison, WI (US)

(73) Assignee: Wisconsin Alumni Research Foundation

( * ) Notice: Subject to any disclaimer, the term of this patent is extended or adjusted under 35 U.S.C. 154(b) by 0 days.

(21) Appl. No.: 17/978,793

(22) Filed: Nov. 1, 2022

(65) Prior Publication Data

US 2023/0138788 A1    May 4, 2023

Related U.S. Application Data

(60) Provisional application No. 63/274,851, filed on Nov. 2, 2021.

(51) Int. Cl.
*G01N 33/92* (2006.01)
*C11D 1/14* (2006.01)
(Continued)

(52) U.S. Cl.
CPC ............. *G01N 33/92* (2013.01); *C11D 1/143* (2013.01); *G01N 21/33* (2013.01); *G01N 33/52* (2013.01)

(58) Field of Classification Search
CPC ........ G01N 33/92; G01N 33/52; G01N 21/33; C11D 1/143
See application file for complete search history.

(56) References Cited

U.S. PATENT DOCUMENTS 6,537,432 B1   3/2003   Schneider et al.
8,697,447 B2   4/2014   Caprioli et al.
(Continued)

FOREIGN PATENT DOCUMENTS

WO   WO-2019236620 A1 * 12/2019 ........... C07C 309/14

OTHER PUBLICATIONS

Zhang et al., "Liposomes formed from photo-cleavable phospholipids: in situ formation and photo-induced enhancement in permeability", 2018, Royal Society of Chemistry, 8, 14669-14675. (Year: 2018).*

(Continued)

*Primary Examiner* — Jennifer Wecker
*Assistant Examiner* — Kathryn Elizabeth Limbaugh
(74) *Attorney, Agent, or Firm* — Leydig, Voit & Mayer, Ltd.

(57) ABSTRACT

Exosomes are a small type of extracellular vesicles containing nucleic acids, lipids, and proteins that are implicated in tumorigenesis, metastasis, and cardiac regeneration, and therefore serve as potentially useful biomarkers from fluids or as vehicles for drug delivery. Global bottom-up mass spectrometry-based proteomics has been previously used to profile exosome cargo for diagnostic purposes. However, the current protocols for MS analysis of extracellular vesicles and exosome proteomics are challenging due to labor-intensive sample preparation, including lengthy digestion times and removal of MS incompatible reagents, and the need for high sensitivity. To address these challenges, the present invention provides a novel, high-throughput strategy for extracellular vesicle analysis and exosome proteomics using a photo-cleavable, anionic surfactant, preferably 4-hexylphenylazosulfonate (Azo). These photo-cleavable, anionic surfactants are able to facilitate high-throughput (Continued)

digestion with minimal sample cleanup for quantitative and highly reproducible analysis.

17 Claims, 29 Drawing Sheets

(51) Int. Cl.
 *G01N 21/33* (2006.01)
 *G01N 33/52* (2006.01)

(56) References Cited

U.S. PATENT DOCUMENTS

| | | |
|---|---|---|
| 9,816,054 B2 | 11/2017 | Saveliev et al. |
| 11,567,085 B2 | 1/2023 | Ge et al. |
| 2018/0299463 A1 | 10/2018 | Piehowski et al. |
| 2023/0139837 A1 | 5/2023 | Ge et al. |

OTHER PUBLICATIONS

"Proteomics of Extracellular Vesicles: Update on Their Composition, Biological Roles and Potential Use as Diagnostic Tools in Atherosclerotic Cardiovascular Diseases", 2020, Diagnostics, 10, 843, pp. 1-34. (Year: 2020).*
Aballo et al. (Aug. 2021) Ultrafast and Reproducible Proteomics from Small Amounts of Heart Tissue Enabled by Azo and TimsTOF Pro. J. Proteome Res. 20 (8), 4203-4211.
Aebersold et al. (2016) "Mass-spectrometric exploration of proteome structure and function" Nature 537, 347-355.
Aebersold et al. (Mar. 2018) "How many human proteoforms are there?" Nature Chemical Biology 14, 206-214.
Altelaar et al. (2013) "Next-generation proteomics: towards an integrative view of proteome dynamics" Nature Reviews | Genetics 14, 35-48.
Apweiler et al. (2004) "UniProt: The Universal Protein knowledgebase" Nucleic Acids Research 32, D115-D119.
Barrera et al. (2011) "Advances in the Mass Spectrometry of Membrane Proteins: From Individual Proteins to Intact Complexes" Annu. Rev. Biochem. 80, 247-271.
Bereman et al. (2011) "Comparison between procedures using SDS for shotgun proteomic analyses of complex samples" Proteomics, 11, 2931-2935.
Bogen et al. (2012) "Light-triggered conversion of non-ionic into ionic surfactants: towards cameleon detergents for 2-D gel electrophoresis," Photochemical & Photobiological Sciences, 11, 497-499.
Botelho et al. (2010) "Top-Down and Bottom-Up Proteomics of SDS-Containing Solutions Following Mass-Based Separation" Journal of Proteome Research, 9, 2863-2870.
Bradley et al. (2006) "Photoresponsive Surfactants in Microgel Dispersions," Langmuir vol. 22, 101-105.
Brodbelt (Jan. 2014) Photodissociation mass spectrometry: new tools for characterization of biological molecules. Chem. Soc. Rev., 43(8): 2757-2783.
Brown et al. (Feb. 2020) High-Throughput Proteomics Enabled by a Photocleavable Surfactant. Angew. Chem., Int. Ed. 59 (22), 8406-8410.
Brown et al. (May 2019) A Photocleavable Surfactant for Top-down Proteomics. Nat. Methods 16 (5), 417-420.
Buck et al. (May 2022) "One-Pot Exosome Proteomics Enabled by a Photocleavable Surfactant," with Supporting Information, Anal. Chem. 94, 20, 7164-7168.
Buck et al. (Nov. 2021) "Rapid Exosome Proteomics Enabled by Azo and timsTOF Pro," Poster Presentation, ASMS Conference, Nov. 3, 2021.
Budnik et al. (Mar. 2016) Extracellular Vesicles Round off Communication in the Nervous System. Nat. Rev. Neurosci. 17 (3), 160-172.

Cai et al. (2014) Plasma Membrane Translocation of Trimerized MLKL Protein Is Required for TNF-Induced Necroptosis. Nat. Cell Biol. 16 (1), 55-65.
Cai et al. (2016) "MASH Suite Pro: A Comprehensive Software Tool for Top-Down Proteomics" Molecular & Cellular Proteomics 15.2, 703-714.
Cai et al. (2016) "Top-down Proteomics: Technology Advancements and Applications to Heart Diseases" Expert Rev Proteomics, 13(8), 717-730.
Chang et al. (2015) "New Mass-Spectrometry-Compatible Degradable Surfactant for Tissue Proteomics" Journal of Proteome Research, 14, 1587-1599.
Chen et al. (2013) Diverse Sequence Determinants Control Human and Mouse Receptor Interacting Protein 3 (RIP3) and Mixed Lineage Kinase Domain-like (MLKL) Interaction in Necroptotic Signaling. J. Biol. Chem. 288 (23), 16247-16261.
Chen et al. (Jan. 2018) "Top-Down Proteomics: Ready for Prime Time?" Anal. Chem. 90, 110-127.
Cho et al. (2009) Phosphorylation-Driven Assembly of the RIP1-RIP3 Complex Regulates Programmed Necrosis and Virus-Induced Inflammation. Cell 137 (6), 1112-1123.
Cravatt et al. (2007) "The biological impact of mass-spectrometry-based proteomics" Nature 450, 991-1001.
Douanne et al. (Aug. 2019) Pannexin-1 Limits the Production of Proinflammatory Cytokines during Necroptosis. EMBO Rep. 20 (10), e47840.
Douhal et al. (1995) "Femtosecond molecular dynamics of tautomerization in model base pairs" Nature, 378, 260-263.
Duan et al. (2009) "A Straightforward and Highly Efficient Precipitation/On-Pellet Digestion Procedure Coupled with a Long Gradient Nano-LC Separation and Orbitrap Mass Spectrometry for Label-Free Expression Profiling of the Swine Heart Mitochondrial Proteome" Journal of Proteome Research, 8, 2838-2850.
Dunkin et al. (1996) "Synthesis, characterization and applications of azo-containing photodestructible surfactants," Journal of the Chemical Society, Perkin Transactions 2, Issue 9, 1837-1842.
Durbin et al. (2014) "Autopilot: An Online Data Acquisition Control System for the Enhanced High-Throughput Characterization of Intact Proteins" Anal. Chem. 86, 1485-1492.
Ea et al. (2006) Activation of IKK by TNF$\alpha$ Requires Site-Specific Ubiquitination of RIP1 and Polyubiquitin Binding by NEMO. Mol. Cell 22 (2), 245-257.
Fan et al. (May 2019) Flotillin-Mediated Endocytosis and ALIX-Syntenin-1—Mediated Exocytosis Protect the Cell Membrane from Damage Caused by Necroptosis. Sci. Signal. 12 (583) eaaw3423.
Ferguson et al. (2016) Exosomes as Therapeutics: The Implications of Molecular Composition and Exosomal Heterogeneity. J. Controlled Release. 228, 179-190.
Gao et al. (Apr. 2018) "Large Cardiac Muscle Patches Engineered From Human Induced-Pluripotent Stem Cell-Derived Cardiac Cells Improve Recovery From Myocardial Infarction in Swine" Circulation 137, 1717-1730.
Gong et al. (2017) ESCRT-III Acts Downstream of MLKL to Regulate Necroptotic Cell Death and Its Consequences. Cell 169 (2), 286-300.e16.
Goulet et al. (Jul. 2018) Exosomes Induce Fibroblast Differentiation into Cancer-Associated Fibroblasts through TGFB Signaling. Mol Cancer Res 16(7): 1196-1204 (accessed Jan. 31, 2021).
Gregorich et al. (2014) "Top-down proteomics in health and disease: Challenges and opportunities" Proteomics 14, 1195-1210.
Gupta et al. (Sep. 2022) "Necroptosis is associated with Rab27-independent expulsion of extracellular vesicles containing RIPK3 and MLKL," Journal of Extracellular Vesicles, 11, e12261. https://doi.org/10.1002/jev2.12261.
Harmati et al. (Oct. 2019) Small Extracellular Vesicles Convey the Stress-Induced Adaptive Responses of Melanoma Cells. Sci. Rep. 9 (1), 15329.
He et al. (2009) Receptor Interacting Protein Kinase-3 Determines Cellular Necrotic Response to TNF-$\alpha$. Cell A86137 (6), 1100-1111.
Hildebrand et al. (2014) Activation of the Pseudokinase MLKL Unleashes the Four-Helix Bundle Domain to Induce Membrane Localization and Necroptotic Cell Death. Proc. Natl. Acad. Sci. 111 (42), 15072-15077.

(56) References Cited

OTHER PUBLICATIONS

Holliday et al. (Dec. 2019) Actin and Actin-Associated Proteins in Extracellular Vesicles Shed by Osteoclasts. Int. J. Mol. Sci. 21 (1), 158.
Hoover et al. (Jan. 2020) Evaluation of Nanoparticle Tracking Analysis for the Detection of Rod-Shaped Particles and Protein Aggregates. J. Pharm. Sci. 109, 452-463.
Hoshino et al. (2015) Tumour Exosome Integrins Determine Organotropic Metastasis. Nature. 527 (7578), 329-335.
Hsu et al. (1996) TNF-Dependent Recruitment of the Protein Kinase RIP to the TNF Receptor-1 Signaling Complex. Immunity 4 (4), 387-396.
Huynh et al. (2005) The Small Chemical Vacuolin-1 Alters the Morphology of Lysosomes without Inhibiting Ca2+-Regulated Exocytosis. EMBO Rep. 6 (9), 843-847.
Hwang et al. (2016) "A Family of Photolabile Nitroveratryl-Based Surfactants That Self-Assemble into Photodegradable Supramolecular Structures," Langmuir vol. 32, 3963-3969.
Hwang et al. (2016) "A Family of Photolabile Nitroveratryl-Based Surfactants That Self-Assemble into Photodegradable Supramolecular Structures," Langmuir, Supporting Information, issue 32, pp. S1-S13.
Kalluri et al. (Feb. 2020) The Biology, Function, and Biomedical Applications of Exosomes. Science 367 (6478).
Kanayama et al. (2004) TAB2 and TAB3 Activate the NF-KB Pathway through Binding to Polyubiquitin Chains. Mol. Cell 15 (4), 535-548 . . . .
Keerthikumar et al. (2016) ExoCarta: A Web-Based Compendium of Exosomal Cargo. J. Mol. Biol. 428 (4), 688-692.
Kim et al. (2006) "Photocleavage of o-nitrobenzyl ether derivatives for rapid biomedical release applications" Bioorg. Med. Chem. Lett. 16, 4007-4010.
Kim et al. (2014) "A draft map of the human proteome" Nature 509, 575-581.
Kim et al. (2017) Caspase-8 Controls the Secretion of Inflammatory Lysyl-TRNA Synthetase in Exosomes from Cancer Cells. J. Cell Biol. 216 (7), 2201-2216.
Kist et al. (Sep. 2020) Impaired RIPK1 Ubiquitination Sensitizes Mice to TNF Toxicity and Inflammatory Cell Death. Cell Death Differ. 28, 985-1000.
Knott et al. (Nov. 2020) Photocleavable Surfactant-Enabled Extracellular Matrix Proteomics. Anal. Chem. 92 (24), 15693-15698.
Kong et al. (2017) MSFragger: ultrafast and comprehensive peptide identification in mass spectrometry-based proteomics. Nat Methods 14, 513-520.
Kowal et al. (2016) Proteomic Comparison Defines Novel Markers to Characterize Heterogeneous Populations of Extracellular Vesicle Subtypes. PNAS. 113 (8), E968-E977.
Kugeratski et al. (Jun. 2021) Quantitative Proteomics Identifies the Core Proteome of Exosomes with Syntenin-1 as the Highest Abundant Protein and a Putative Universal Biomarker. Nat. Cell Biol. 23 (6), 631-641.
Loo et al. (1994) "Surfactant effects on protein structure examined by electrospray ionization mass spectrometry" Protein Science 3, 1975-1983.
Loughrey et al. (2016) Using the NanoDrop One to Quantify Protein and Peptide Preparations at 205 nm. Thermo Fisher Scientific.
MacLennan et al. (2003) "Phospholamban: A Crucial Regulator of Cardiac Contractility" Nature 4, 566-577.
Medina et al. (Apr. 2020) Metabolites released from apoptotic cells act as tissue messengers. Nature 580, 130-135. (accessed Jan. 31, 2021).
Meier et al. (Dec. 2018) Online Parallel Accumulation-Serial Fragmentation (PASEF) with a Novel Trapped Ion Mobility Mass Spectrometer. Mol. Cell. Proteomics. 17 (12), 2534-2545.
Melby et al. (Jun. 2021) Novel Strategies to Address the Challenges in Top-Down Proteomics. J. Am. Soc. Mass Spectrom 32 (6), 1278-1294.
Mezger et al. (1996) "Light decomposable emulsifiers: application of alkyl-substituted aromatic azosulfonates in emulsion polymerization" Progress in Organic Coatings 29, 147-157.
Muller et al. (2017) Systematic Evaluation of Protein Reduction and Alkylation Reveals Massive Unspecific Side Effects by Iodine-Containing Reagents. Molecular & cellular proteomics : Molecular & Cellular Proteomics 16 (7), 1173-1187.
Orozco et al. (2014) RIPK1 Both Positively and Negatively Regulates RIPK3 Oligomerization and Necroptosis. Cell Death Differ. 21 (10), 1511-1521.
Ostrowski (2010) Rab27a and Rab27b Control Different Steps of the Exosome Secretion Pathway. Nat. Cell Biol. 12 (1), 19-30.
Pathan et al. (Jan. 2019) Vesiclepedia 2019: A Compendium of RNA, Proteins, Lipids and Metabolites in Extracellular Vesicles. Nucleic Acids Res. 2019, 47 (D1), D516-D519.
Pavlyukov et al. (Jul. 2018) Apoptotic Cell-Derived Extracellular Vesicles Promote Malignancy of Glioblastoma via Intercellular Transfer of Splicing Factors. Cancer Cell. 34 (1), 119-135.e10.
Prive et al. (2007) "Detergents for the stabilization and crystallization of membrane proteins" Methods 41, 388-397.
Reddy et al. (2001) Plasma Membrane Repair Is Mediated by Ca2+-Regulated Exocytosis of Lysosomes. Cell 106 (2), 157-169.
Rock (2008) The Inflammatory Response to Cell Death. Annu. Rev. Pathol. 3, 99-126.
Rontogianni et al. (Sep. 2019) Proteomic Profiling of Extracellular Vesicles Allows for Human Breast Cancer Subtyping. Commun. Biol. 2 (1), 325 . . . .
Sahoo et al. (Apr. 2021) Therapeutic and Diagnostic Translation of Extracellular Vesicles in Cardiovascular Diseases. Circulation 143 (14), 1426-1449.
Samson et al. (Jun. 2020) MLKL Trafficking and Accumulation at the Plasma Membrane Control the Kinetics and Threshold for Necroptosis. Nat. Commun. 11 (1), 3151.
Schey et al. (2015) Proteomics Characterization of Exosome Cargo. Methods 87, 75-82.
Sedger et al. (2014) TNF and TNF-Receptors: From Mediators of Cell Death and Inflammation to Therapeutic Giants-Past, Present and Future. Cytokine Growth Factor Rev. 25 (4), 453-472.
Seo et al. (2016) CHIP Controls Necroptosis through Ubiquitylation- and Lysosome-Dependent Degradation of RIPK3. Nat. Cell Biol. 18 (3), 291-302.
Shlomovitz et al. (Nov. 2021) Proteomic analysis of necroptotic extracellular vesicles. Cell Death and Disease 12: 1059 (accessed Jan. 31, 2021).
Simpson (2009) Exosomes: Proteomic Insights and Diagnostic Potential. Expert Rev. Proteomics. 6 (3), 267-283.
Siuti et al. (2007) "Decoding protein modifications using top-down mass spectrometry" Nature Methods, 4(10), 817-821.
Smith et al. (2013) "Proteoform: a single term describing protein complexity" Nature Methods 10(3), 186-187.
Smith et al. (2018) "Proteoforms as the next proteomics currency" Science 359(6380), 1106-1108.
Sokolova et al. (2011) Characterisation of Exosomes Derived from Human Cells by Nanoparticle Tracking Analysis and Scanning Electron Microscopy. Colloids and Surfaces B: Biointerfaces. 87 (1), 146-150.
Speers et al. (2007) "Proteomics of Integral Membrane Proteomics—Theory and Application" Chem. Rev. 107, 3687-3714.
Su et al. (2014) A Plug Release Mechanism for Membrane Permeation by MLKL. Structure 2014, 22 (10), 1489-1500.
Sun et al. (2002) Identification of a Novel Homotypic Interaction Motif Required for the Phosphorylation of Receptor-Interacting Protein (RIP) by RIP3. J. Biol. Chem. 277 (11), P9505-9511.
Sung et al. (2015) Directional Cell Movement through Tissues Is Controlled by Exosome Secretion. Nat. Comm. 6 (1), 7164.
Szklarczyk et al. (Nov. 2018) String V11: Protein-Protein Association Networks with Increased Coverage, Supporting Functional Discovery in Genome-Wide Experimental Datasets. Nucleic Acids Res. 47 (D1), D607-D613.
Tanzer et al. (Jan. 2020) Quantitative and Dynamic Catalogs of Proteins Released during Apoptotic and Necroptotic Cell Death. Cell Rep. 30 (4), 1260-1270.e5.
Tehrani-Bagha et al. (2007) "Cleavable Surfactants" Current Opinion in Colloid & Interface Science 12, 81-91.
Théry et al. (Dec. 2018) Minimal Information for Studies of Extracellular Vesicles 2018 (MISEV2018): A Position Statement of

(56) References Cited

OTHER PUBLICATIONS the International Society for Extracellular Vesicles and Update of the MISEV2014 Guidelines. J. Extracell. Vesicles 7 (1), 1535750.

Tkach et al. (2016) Communication by Extracellular Vesicles: Where We Are and Where We Need to Go. Cell 164 (6), 1226-1232.

Trairak et al. (2004) Identification and Proteomic Profiling of Exosomes in Human Urine. PNAS 101 (36), 13368-13373.

Waas et al. (2014) Combine and Conquer: Surfactants, Solvents, and Chaotropes for Robust Mass Spectrometry Based Analyses of Membrane Proteins. Analytical Chemistry 86 (3), 1551-1559.

Walbrecq et al. (Jul. 2020) Distinct Cargos of Small Extracellular Vesicles Derived from Hypoxic Cells and Their Effect on Cancer Cells. Int. J. Mol. Sci. 21 (14), 5071.

Walpole et al. (2015) "Conservation of Complete Trimethylation of Lysine-43 in the Rotor Ring of c-Subunits of Metazoan Adenosine Triphosphate (ATP) Synthases" Molecular & Cellular Proteomics 14(4), 828-840.

Whitelegge (2013) "Integral Membrane Proteins and Bilayer Proteomics" Anal. Chem. 85, 2558-2568.

Whitelegge et al. (1999) "Toward the bilayer proteome, electrospray ionization-mass spectrometry of large, intact transmembrane proteins" Proc. Natl. Acad. Sci. 96, 10695-10698.

Wientzek et al. (1991) "Isolation and Characterization of Purified Sarcoplasmic Reticulum Membranes from Isolated Adult Rat Ventricular Myocytes" J Mol Cell Cardiol 23, 1149-1163.

Wisniewski et al. (2009) "Universal Sample preparation method for proteome analysis" Nature Methods 6(5), 359-363.

Wu et al. (2003) "The application of mass spectrometry to membrane proteomics" Nature Biotechnology 21, 262-267.

Wu et al. (2013) Mlkl Knockout Mice Demonstrate the Indispensable Role of Mlkl in Necroptosis. Cell Res. 23 (8), 994-1006.

Yan et al. (2013) "Photoisomerization Quantum Yield of Azobenzene-Modified DNA Depends on Local Sequence" J. Am. Chem. Soc. 135, 8382-8387.

Yergey (1983) "A general approach to calculating isotopic distributions for mass spectrometry" International Journal of Mass Spectrometry and Ion Physics, 52, 337-349.

Yoon et al. (2017) MLKL, the Protein That Mediates Necroptosis, Also Regulates Endosomal Trafficking and Extracellular Vesicle Generation. Immunity 47 (1), 51-65.e7.

Yu et al. (2003) "Enzyme-Friendly, Mass Spectrometry-Compatible Surfactant for In-Solution Enzymatic Digestion of Proteins" Anal. Chem. 75, 6023-6028.

Yu et al. (Apr. 2021) IonQuant Enables Accurate and Sensitive Label-Free Quantification With FDR-Controlled Match-Between-Runs. Molecular & Cellular Proteomics 20: 100077.

Yu et al. (Sep. 2020) Fast Quantitative Analysis of TimsTOF PASEF Data with MSFragger and IonQuant. Mol. Cell. Proteomics. 2020, 19 (9), 1575-1585.

Zargarian et al. (2017) Phosphatidylserine Externalization, "Necroptotic Bodies" Release, and Phagocytosis during Necroptosis. PLOS Biol. 15 (6), e2002711.

Zhang et al. (2009) RIP3, an Energy Metabolism Regulator That Switches TNF-Induced Cell Death from Apoptosis to Necrosis. Science 325 (5938), 332-336.

Zhang et al. (Sep. 2019) Ubiquitination of RIPK1 Suppresses Programmed Cell Death by Regulating RIPK1 Kinase Activation during Embryogenesis. Nat. Commun., 10 (1), 4158.

Zhou et al. (2015) "Palmitoyl acyltransferase Aph2 in cardiac function and the development of cardiomyopathy" PNAS 112(51), 15666-15671.

Zulkefli et al. (Jul. 2019) A Role for Rab11 in the Homeostasis of the Endosome-Lysosomal Pathway. Exp. Cell Res. 380 (1), 55-68.

\* cited by examiner

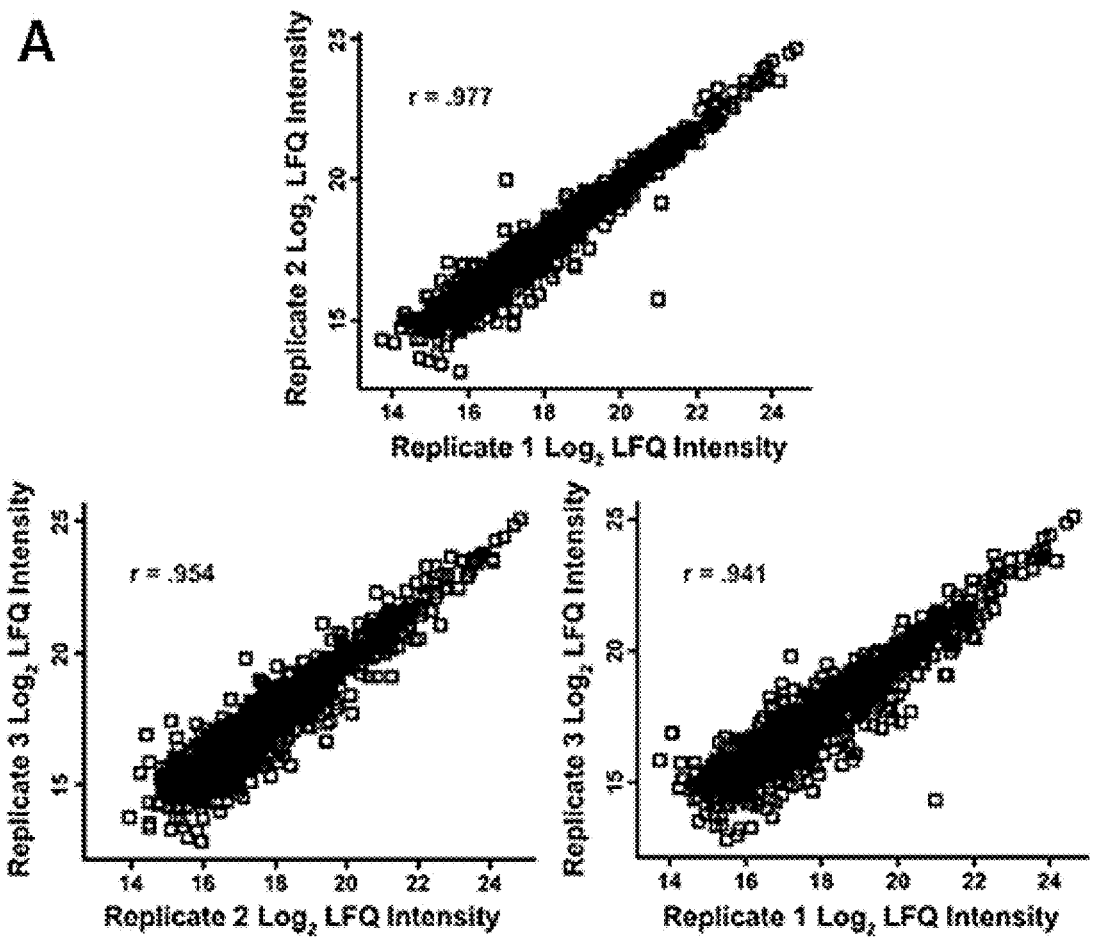
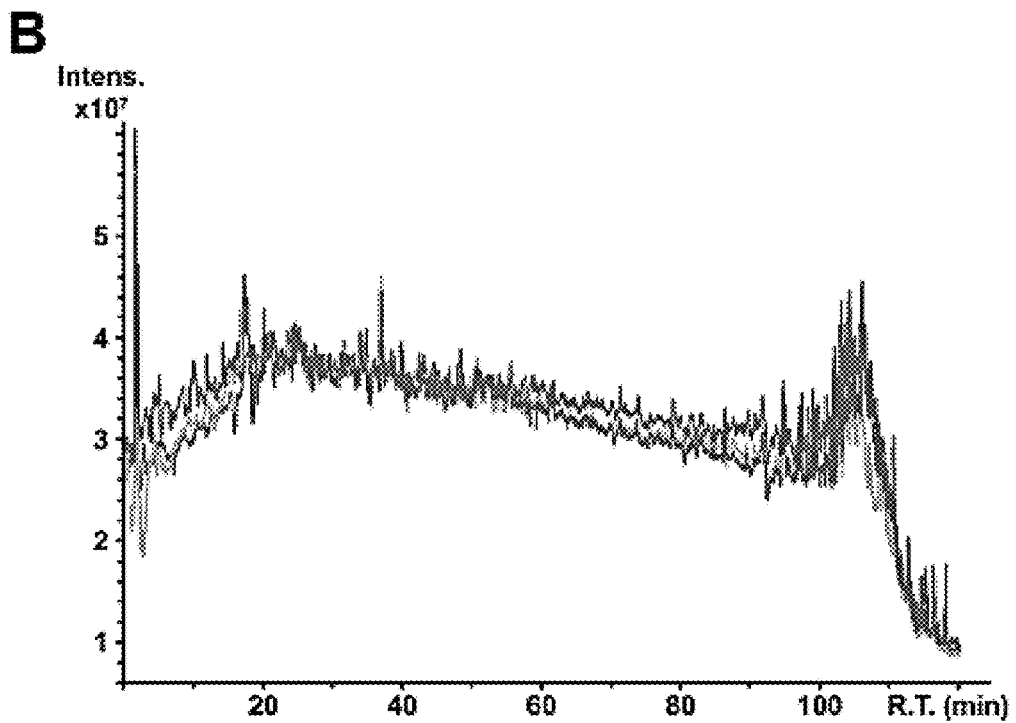
Fig. 7

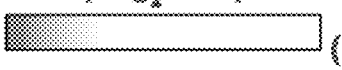

| Rank in Top 100 | Gene Symbol | Rank in Top 100 | Gene Symbol | Rank in Top 100 | Gene Symbol |
|---|---|---|---|---|---|
| 1 | CD9 | 35 | HSPA5 | 68 | ACTG1 |
| 2 | PDCD6IP | 36 | SLC3A2 | 69 | KPNB1 |
| 3 | HSPA8 | 37 | HIST1H4A | 70 | EZR |
| 4 | GAPDH | 38 | GNB2 | 71 | ANXA4 |
| 5 | ACTB | 39 | ATP1A1 | 72 | ACLY |
| 6 | ANXA2 | 40 | YWHAQ | 73 | TUBA1C |
| 7 | CD63 | 41 | FLOT1 | 74 | TFRC |
| 8 | SDCBP | 42 | FLNA | 75 | RAB14 |
| 9 | ENO1 | 43 | CLIC1 | 76 | HIST2H4A |
| 10 | HSP90AA1 | 44 | CCT2 | 77 | GNB1 |
| 11 | TSG101 | 45 | CDC42 | 78 | THBS1 |
| 12 | PKM | 46 | YWHAG | 79 | RAN |
| 13 | LDHA | 47 | A2M | 80 | RAB5A |
| 14 | EEF1A1 | 48 | TUBA1B | 81 | PTGFRN |
| 15 | YWHAZ | 49 | RAC1 | 82 | CCT5 |
| 16 | PGK1 | 50 | LGALS3BP | 83 | CCT3 |
| 17 | EEF2 | 51 | HSPA1A | 84 | AHCY |
| 18 | ALDOA | 52 | GNAI2 | 85 | UBA1 |
| 19 | HSP90AB1 | 53 | ANXA1 | 86 | RAB5B |
| 20 | ANXA5 | 54 | RHOA | 87 | RAB1A |
| 21 | FASN | 55 | MFGE8 | 88 | LAMP2 |
| 22 | YWHAE | 56 | PRDX2 | 89 | ITGA6 |
| 23 | CLTC | 57 | GDI2 | 90 | HIST1H4B |
| 24 | CD81 | 58 | EHD4 | 91 | BSG |
| 25 | ALB | 59 | ACTN4 | 92 | YWHAH |
| 26 | VCP | 60 | YWHAB | 93 | TUBA1A |
| 27 | TPI1 | 61 | RAB7A | 94 | TKT |
| 28 | PPIA | 62 | LDHB | 95 | TCP1 |
| 29 | MSN | 63 | GNAS | 96 | STOM |
| 30 | CFL1 | 64 | RAB5C | 97 | SLC16A1 |
| 31 | PRDX1 | 65 | ARF1 | 98 | RAB8A |
| 32 | PFN1 | 66 | ANXA6 | 99 | MYH9 |
| 33 | RAP1B | 67 | ANXA11 | 100 | MVP |
| 34 | ITGB1 | | | | |

Fig. 9

Color Scale (Log$_2$ LFQ)

24 (max.) — 12 (min.)

| | | | | | |
|---|---|---|---|---|---|
| AARS1 | CIAO2B | GPATCH4 | LSM8 | PTPA | SSPN |
| ABRAXAS2 | CIAO3 | GPKOW | LY96 | PYCR3 | SSU72 |
| ACTR6 | CMC2 | GRK2 | MACROH2A1 | QARS1 | SSX1 |
| ADGRF5 | CNPY4 | GSDME | MAD2L1 | QKI | SUMF1 |
| ADPRS | COA4 | GTF2A1 | MARS1 | RAB3IL1 | SUSD6 |
| ADSS2 | COA6 | GTF2E1 | MDFIC | RABEP2 | SYT11 |
| AK5 | COA7 | GTF2F2 | MEAK7 | RABL6 | TACC3 |
| AKAP8L | COMMD8 | GTSF1 | MENT | RACK1 | TARS1 |
| ANKRD40 | COPRS | H1-10 | METTL9 | RAD9A | THUMPD1 |
| ARFGAP2 | COPZ2 | H1-2 | MGAT4B | RARS1 | TIGAR |
| ARL6IP4 | CPSF4 | H1-4 | MIER1 | RECQL5 | TIMM10 |
| ASCC1 | CRYBG1 | H1-5 | MIX23 | RELB | TIMM10B |
| ATP5F1A | CWC15 | H3-2 | MORF4L1 | RELCH | TMEM115 |
| ATP5F1B | CYRIB | H3-3A | MPC2 | RETREG3 | TMEM123 |
| ATP5F1C | CZIB | H3C1 | MRE11 | RFLNB | TMEM184C |
| ATP5F1D | DAP | H3C15 | MRPL24 | RMDN1 | TMEM199 |
| ATP5ME | DARS1 | H4C1 | MRPS10 | RNF24 | TMEM258 |
| ATP5MF | DPH2 | HAX1 | MSR1 | RO60 | TMEM263 |
| ATP5MK | ECPAS | HDGFL2 | MT-ATP6 | RPAP3 | TNS2 |
| ATP5PB | EFCAB14 | HGH1 | MT-CO2 | RTF1 | TOMM70 |
| ATP5PD | EIF4EBP1 | HNRNPLL | MTREX | RTRAF | TOX4 |
| ATP5PF | EIPR1 | HSBP1 | MYG1 | RWDD4 | TRAFD1 |
| ATP5PO | ELOB | HSP90AB4P | NAF1 | S1PR3 | TRIM27 |
| B4GAT1 | ELOC | HYPK | NAGPA | SAMSN1 | TRMT10C |
| BABAM2 | ELP1 | IARS1 | NARF | SAP30BP | TSC22D2 |
| BMPER | EML1 | IGHD | NARS1 | SARS1 | TSC22D4 |
| BPNT2 | ENDOG | IGHV1-18 | NAXE | SELENOF | TVP23C |
| C11orf98 | ENSA | IGKV3-7 | NECTIN2 | SELENOP | TXN2 |
| C18orf25 | EPRS1 | IGKV3D-20 | NECTIN3 | SEMA4B | TXNL4A |
| C4orf3 | ERBIN | IGLV1-47 | NIBAN1 | SENP3 | UBE2L5 |
| CA8 | ERI3 | JMJD6 | NIBAN2 | SEPTIN10 | UFD1 |
| CACNA1I | ERO1A | JPT1 | NOL10 | SEPTIN11 | UMAD1 |
| CALHM5 | ESF1 | JPT2 | NRDC | SEPTIN2 | UNC50 |
| CAMTA2 | FAM20B | KARS1 | NUFIP2 | SEPTIN7 | URI1 |
| CARS1 | FAM234A | KCT2 | OCC1 | SEPTIN8 | VARS1 |
| CAVIN1 | FBXL15 | KIAA1143 | OGA | SEPTIN9 | VPS9D1 |
| CAVIN2 | FBXO30 | KIAA1549L | OLFML1 | SGCZ | WARS1 |
| CAVIN3 | FKRP | KIFBP | ORC4 | SHTN1 | WASHC2A |
| CCDC177 | FLRT1 | KIRREL1 | PBDC1 | SKA3 | WASHC3 |
| CCDC43 | FOXG1 | KPNA7 | PCYT1A | SLC38A7 | WASHC4 |
| CCN1 | GARS1 | KRI1 | PIP4P1 | SLC49A4 | WASHC5 |
| CCN2 | GASK1B | KTI12 | PIP4P2 | SLC66A1 | WDR13 |
| CCN3 | GATA1 | KYAT3 | PLAC9 | SLX9 | WFDC12 |
| CDC42EP4 | GCN1 | L1RE1 | PLPP3 | SMAP | WNT2 |
| CDKN2AIP | GEMIN6 | L3HYPDH | POLR3D | SMNDC1 | YARS1 |
| CEMIP2 | GET3 | LAMTOR5 | PPP1R11 | SNU13 | ZDHHC8 |
| CERT1 | GFUS | LARS1 | PQBP1 | SNX11 | ZNF775 |
| CFAP298 | GINM1 | LDAH | PRRT1 | SQOR | ZNF806 |
| CHPF | GLMP | LNPK | PRSS3P2 | SRPRA | ZNRD2 |
| CHTOP | GOLM2 | LRCH2 | PSME3IP1 | SS18 | ZPR1 |

Fig. 10

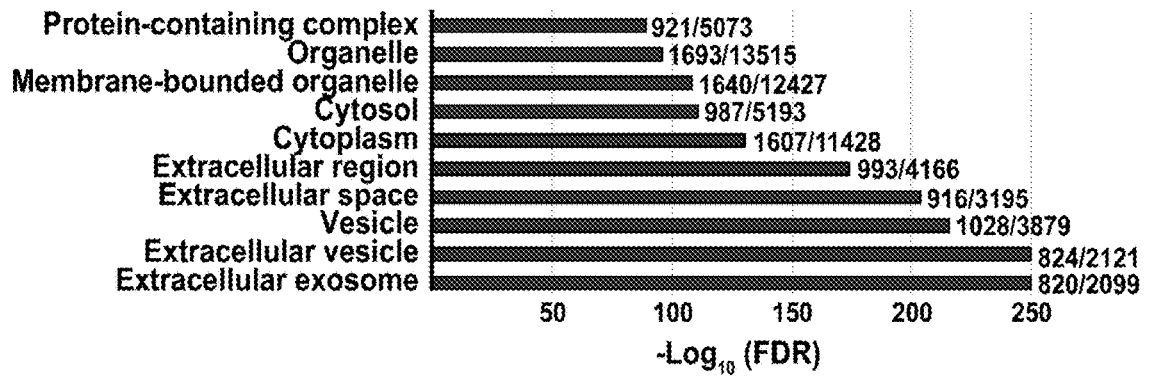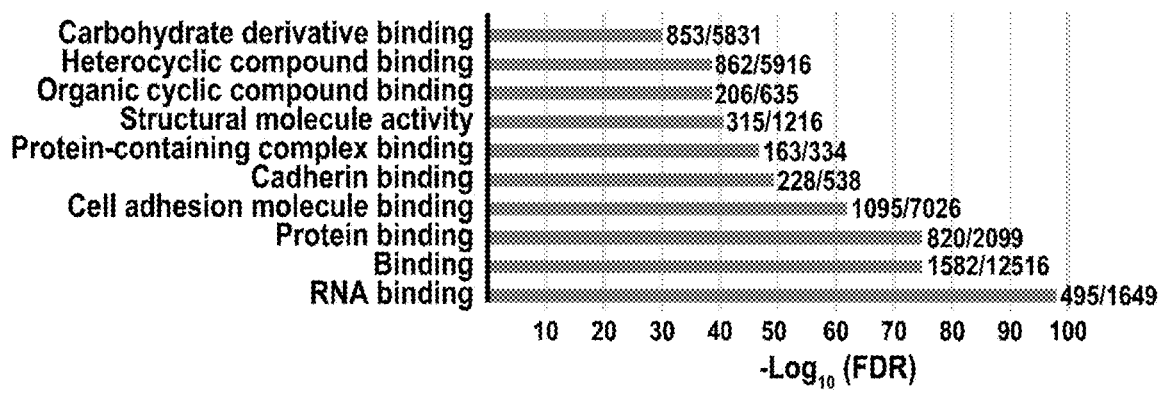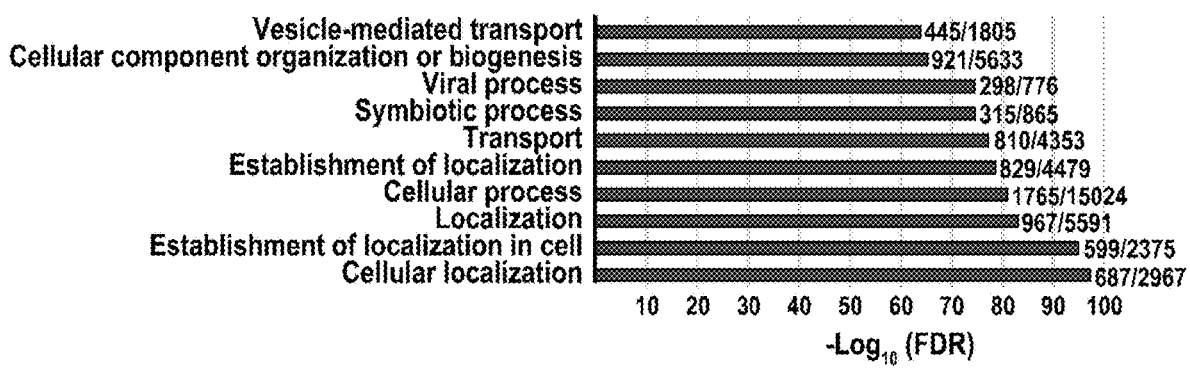
Fig. 11

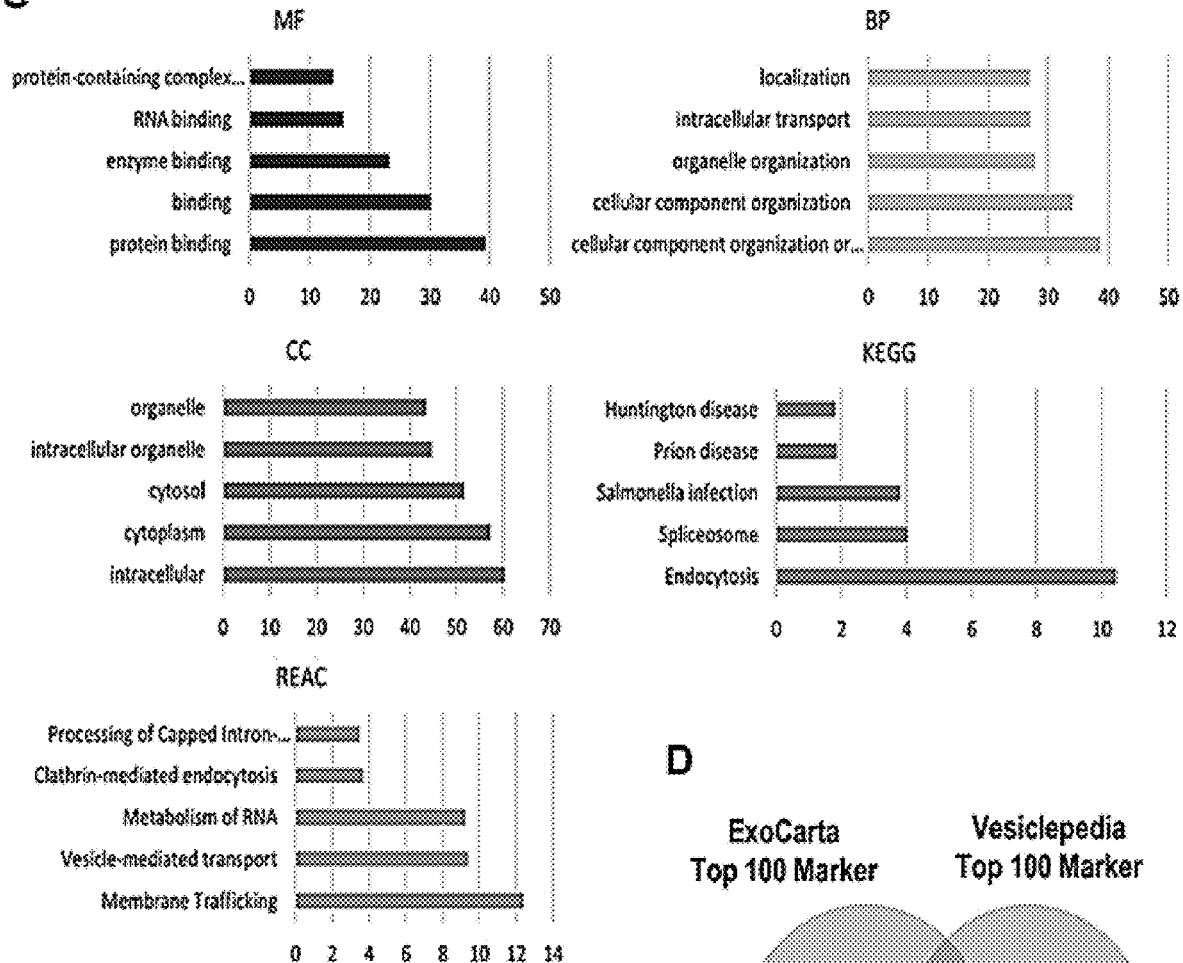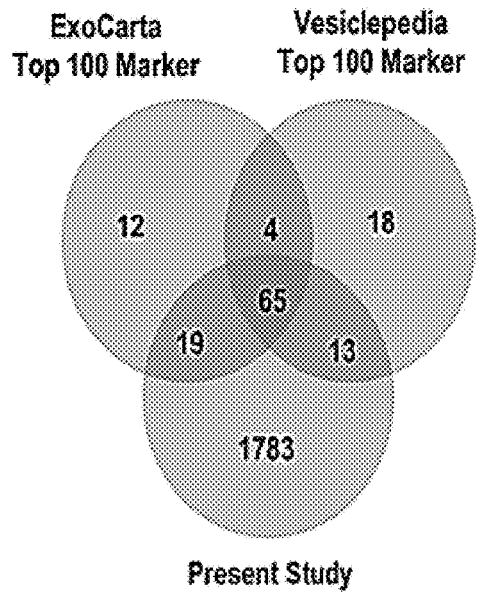
Fig. 14 Cont.

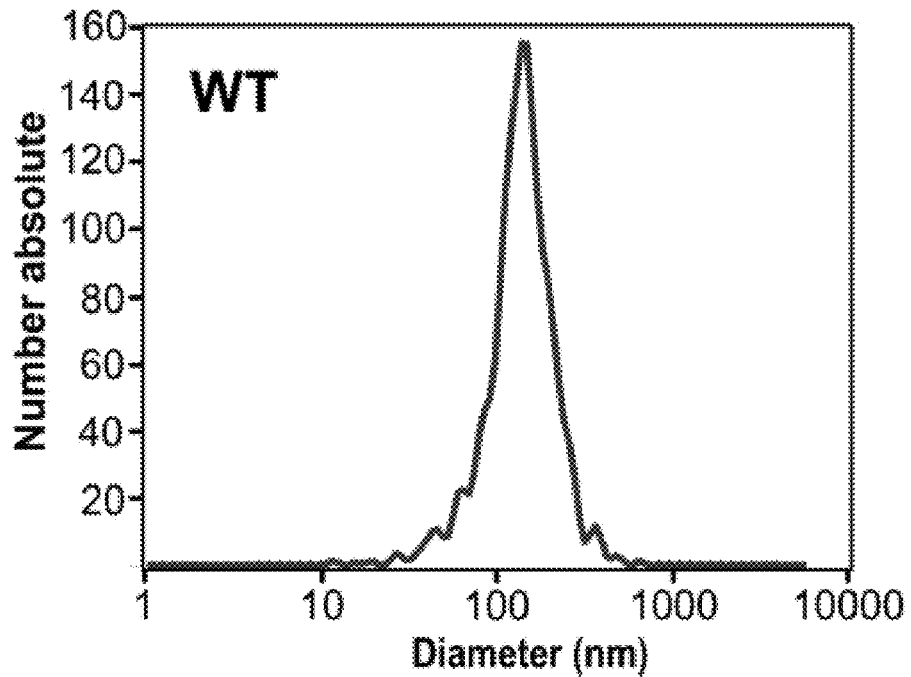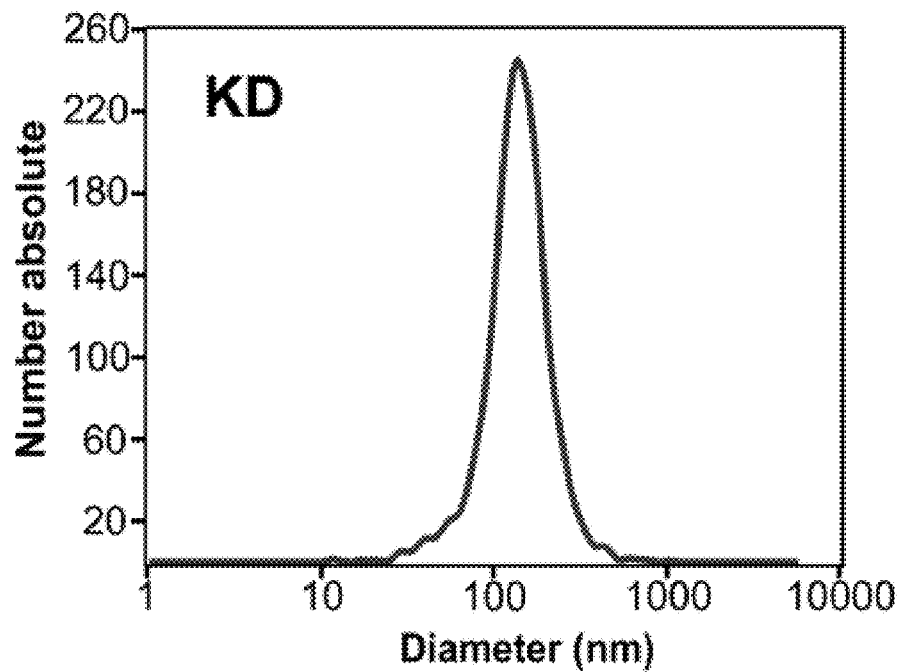
Fig. 19

STRATEGY ENABLED BY A PHOTO-CLEAVABLE SURFACTANT FOR EXTRACELLULAR VESICLE PROTEOMICS

CROSS-REFERENCE TO RELATED APPLICATIONS

This application claims the benefit of priority to U.S. Provisional Patent Application No. 63/274,851, filed Nov. 2, 2021, which is specifically incorporated by reference to the extent not inconsistent herewith.

STATEMENT REGARDING FEDERALLY SPONSORED RESEARCH OR DEVELOPMENT

This invention was made with government support under GM117058 awarded by the National Institutes of Health. The government has certain rights in the invention.

BACKGROUND OF THE INVENTION

Extracellular vesicles (EVs) are nano-sized lipid bound vesicles released from all cells and accessible in most bodily fluids, carry nucleic acid, protein, lipid, and metabolite cargo to facilitate intercellular signaling. EVs are increasingly recognized to have great potential for the development of non-invasive markers for early detection and diagnosis of diseases and monitoring therapy treatments. In particular, exosomes are a type of small EVs (between 30 and 150 nm in diameter) containing nucleic acids, lipids, and proteins that are implicated in tumorigenesis, metastasis, and cardiac regeneration, serving as potentially useful biomarkers from fluids or vehicles for drug delivery. The proteomic contents of these vesicles have potential for detection and as therapeutics for pathologies such as cancer and cardiovascular disease.

Mass spectrometry (MS)-based proteomics represents a powerful tool for detecting potential proteomic biomarkers and other molecules in exosomes and other types of EVs. Recently, global bottom-up MS-based proteomics has been used to profile exosome and other EV cargo for diagnostic purposes. However, current protocols for sample preparation and MS analysis of EV/exosome proteomics are limited by ineffective protein extraction, lengthy digestion times, use of MS incompatible reagents, and lack of analytical sensitivity. Traditional bottom-up sample preparation results in poor proteome coverage and though more sensitive methods for exosome sample preparation have been developed, these methods are laborious and rely on lengthy or multiple digestions, cleanup steps or offline multidimensional separations, which limit sample throughput.

Accordingly, what are needed are methods and compounds for the improved MS analysis of EVs and exosome proteomics, including methods and compounds able to provide quantitative and highly reproducible exosome proteomic analysis. Preferably, the methods and compounds would be able to facilitate high-throughput digestion with minimal sample cleanup and would be compatible with both top-down and bottom-up proteomics.

SUMMARY OF THE INVENTION

To address these challenges, the present invention provides novel, high-throughput strategies for analysis of lipid vesicles, including but not limited to exosomes and other types of extracellular vesicles, using photo-cleavable surfactants. Preferably, the photo-cleavable surfactants are stable under acidic conditions, but can be cleaved and degraded upon irradiation with light, especially ultraviolet (UV) radiation, before mass spectrometry (MS) analysis.

In an embodiment, the photo-cleavable surfactants of the present invention are provided in a method for analyzing lipid vesicles comprising the steps of:
a) contacting one or more lipid vesicles or a mixture of compounds obtained from within one or more lipid vesicles with a photo-cleavable surfactant in a solution until the one or more lipid vesicles or mixture of compounds is dissolved in the solution, wherein the photo-cleavable surfactant comprises: i) a hydrophilic head, ii) a hydrophobic tail, and iii) a photo-cleavable moiety covalently linking the hydrophilic head and hydrophobic tail; and
b) exposing the solution containing the photo-cleavable surfactant and dissolved one or more lipid vesicles or mixture of compounds to electromagnetic radiation, thereby decomposing the photo-cleavable moiety and generating an irradiated solution containing the one or more lipid vesicles or mixture of compounds.

As used herein, a "lipid vesicle" refers to a structure within or outside a cell, containing a liquid or cytoplasm enclosed by a lipid bilayer. In an embodiment, the lipid vesicles are one or more extracellular vesicles obtained from one or more cells or samples from a subject. Examples of suitable extracellular vesicles able to be analyzed using the present invention include but are not limited to exosomes, ectosomes, oncosomes, microvesicles (MVs), and apoptotic bodies. Preferably, the lipid vesicles are one or more exosomes obtained from one or more cells or samples from a subject. Suitable samples include, but are not limited to, cells, tissues, and biofluids. In an embodiment, the lipid vesicles are one or more liposomes. In an embodiment, the lipid vesicles have an average diameter between 10 and 1,000 nm, preferably between 20 and 500 nm, or preferably between 30 and 150 nm.

Preferably, the method further comprises performing mass spectrometry (MS) analysis on a portion of the irradiated solution containing the one or more lipid vesicles or mixture of compounds. Optionally, the MS analysis comprises tandem mass spectrometry and/or liquid chromatography-mass spectrometry. In an embodiment, after dissolving the one or more lipid vesicles or mixture of compounds in the solution containing the photo-cleavable surfactant, a separation step (including but not limited to chromatography) is performed on the solution in order to purify or separate the components in the solution. In an embodiment, the solution which contains the photo-cleavable surfactant and the dissolved one or more lipid vesicles or mixture of compounds is exposed to the electromagnetic radiation before injecting or spraying the dissolved compound into the mass spectrometer. Optionally, the photodegradation caused by exposure to electromagnetic radiation occurs after chromatography separation and before spraying into the mass spectrometer, as the experiments happen in real time.

In an embodiment, the solution which contains the photo-cleavable surfactant and the dissolved one or more lipid vesicles or mixture of compounds is exposed to the electromagnetic radiation within the mass spectrometer device after the solution has been injected or sprayed into the mass spectrometer. For example, in an embodiment photodegradation of the photo-cleavable surfactant occurs within the mass spectrometer during ultraviolet photo-dissociation (UVPD) (see Brodbelt et al., 2014, Chem. Soc. Rev., 43(8): 2757-2783). However, it should be noted that the mass spectrometer device may irradiate the solution with other forms of electromagnetic radiation.

In an embodiment, the method further comprises obtaining the one or more lipid vesicles from one or more cells or samples of at least one subject. Preferably, the cells, samples are involved in one or more diseases or cellular mechanisms of interest, including but not limited to tumorigenesis, metastasis, cardiac regeneration, necroptosis or apoptosis. Optionally, the method further comprises lysing the one or more lipid vesicles to generate the mixture of compounds. In an embodiment, the mixture of compounds comprises nucleic acids, lipids, saccharides, proteins, protein fragments, and combinations thereof. Preferably, the mixture of compounds comprises one or more proteins or protein fragments. In an embodiment, the proteins are part of pathways involved with tumorigenesis, metastasis, cardiac regeneration, necroptosis or apoptosis.

In an embodiment, suitable photo-labile surfactants may be generated by inserting a photo-cleavable moiety in between the hydrophilic head and hydrophobic tail. Preferably, O-nitrobenzyl (ONB), O-nitroveratryl (ONV), and azobenzene (AZO) groups are chosen as the photo-cleavable moieties.

In an embodiment, the photo-cleavable surfactant has the formula:

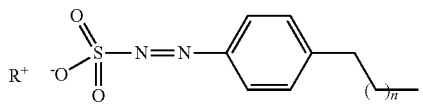

where n is an integer selected from 2 to 30 and R is any atom or molecule able to form a cation in solution. Preferably, n is an integer selected from 2 to 20, an integer selected from 4 to 15, or an integer selected from 6 to 12. Preferably, n is 6, 8, 10 or 12. Preferably, R is calcium, sodium, potassium, hydrogen, or combinations thereof.

In a further embodiment, the photo-cleavable anionic surfactant comprises 4-hexylphenylazosulfonate (also referred to herein as "Azo"), which can be rapidly degraded upon UV irradiation. Azo can effectively solubilize proteins, and after solubilization, a sample to be analyzed using mass spectrometry is exposed to UV radiation, which decomposes the Azo prior to entering the mass spectrometer. It is believed this invention is the first application of a photo-cleavable surfactant (Azo) for extracellular vesicle analysis and exosome proteomics. Optionally, the photo-cleavable surfactant is sodium 4-hexylphenylazosulfonate.

In an embodiment, the Azo-enabled exosome proteomics method is used for basic research seeking to understand the role of exosomes in diseases, including but not limited to cancer, cardiovascular diseases, and vascular diseases, as well as for the detection and discovery of biomarkers. Given the emerging role of exosomes for disease diagnosis, an embodiment of the present method would have clinical applications.

The use of the Azo surfactant enables global protein extraction, rapid digestion, and minimal sample clean-up for high-throughput proteomics of exosomes. The method greatly minimizes the time and labor required to characterize proteins and other molecules in exosomes, which are increasingly recognized in their role in tumorigenesis, metastasis, and cardiac regeneration. Exosomes can serve as potentially useful biomarkers from fluids or vehicles for drug delivery, thus methods improving the characterization of exosome proteins is highly advantageous.

In an embodiment, the present invention provides a dedicated protocol for exosome lysis and protein extraction combined with trapped ion mobility (TIMS)-LC-MS/MS analysis separation for a rapid, sensitive, and quantitative approach to exosome proteomics. This embodiment provides a means for studying protein expression differences between exosomes obtained from two different populations or sources, such as between exosomes obtained from a normal (i.e., wild type) source and an altered (i.e., knockout) source.

Preferably, the electromagnetic radiation used to decompose the photo-cleavable moiety is ultraviolet (UV) light. Preferably, the photo-cleavable moiety releases the hydrophilic head, releases the hydrophobic tail, or degrades under light having a wavelength between 150-450 nm, between 200-400 nm, between 250-350 nm, or between 280-300 nm. In an embodiment, the solution containing the photo-cleavable surfactant and dissolved one or more exosomes or mixture of compounds is exposed to the electromagnetic radiation for a time period between 10 and 500 seconds, preferably between 15 and 400 seconds, between 20 and 300 seconds, between 25 and 200 seconds, or between 30 and 150 seconds.

Preferably, the photo-cleavable surfactant is stable at any pH, but is especially functional at a pH range that is not operable for other existing surfactants, such as acid labile surfactants. In an embodiment, the photo-cleavable surfactant is able to remain stable at a pH of 4 or lower, at a pH of 3 or lower, at a pH of or lower 2, or at a pH of 1 or lower. Conventional acid labile surfactants typically hydrolyze at a pH of approximately 2-3. In an embodiment, the photo-cleavable surfactants of the present invention, such as the Azo surfactant, are stable at any pH and photo degradation is optimal at low pH (~2) with an organic solvent. Under aqueous conditions, pH has little or no effect on the surfactant. This makes surfactants of the present invention well suited for both offline and online LC/MS analysis of proteins, which commonly utilize acid in the electrospray solution and mobile phases. Moreover, many proteins and other molecules need to be extracted under acidic conditions, which renders conventional rapidly acid-labile surfactants ineffective.

The solution comprises an organic solvent, aqueous solvent, or combinations thereof. Optionally, the solution also comprises 10% or less of an acid or reducing agent. Alternatively, the solution does not contain any additional acids or reducing agents. The solution also comprises 1% or less of the photo-cleavable surfactant, preferably 0.5% or less of the photo-cleavable surfactant, preferably 0.1% or less of the photo-cleavable surfactant. In an embodiment, the solution comprises water, acetonitrile, isopropanol, or combinations thereof. In an embodiment, the solution comprises 70% or less of an organic solvent, 5% or less of an acid, and 0.1% or less of the photo-cleavable surfactant.

While aspects of the present invention provide improvements over surfactants and methods used in conjunction with top-down proteomics, it should be noted the present invention is useful for bottom-up proteomics as well. In bottom-up proteomics, proteins are solubilized and digested into smaller polypeptides, and the mixtures of polypeptides are analyzed together. The present methods and surfactants can be utilized to improve solubility of proteins and facilitate the extraction of proteins from exosomes for both top-down proteomics and bottom-up proteomics.

BRIEF DESCRIPTION OF THE DRAWINGS

FIG. 7: Representative injection replicates showing reproducibility of analysis. Panel A) Scatter plots comparing LC injection replicates for sample 3 to each other, with corresponding PCCs. Panel B) Overlaid total ion chromatogram (TIC) traces from injection replicates of sample 3.

FIG. 9: ExoCarta top 100 list, which collects most frequently identified protein markers in exosomes. Markers are color-scaled to the overall range of observed LFQ intensities in the mammary fibroblast exosome samples. High abundance of these markers shows agreement with previous exosome studies.

FIG. 10: Heat map of proteins not annotated in ExoCarta or Vesiclepedia but identified in mammary fibroblast exosome samples. Markers are color-scaled to the overall range of observed LFQ intensities.

FIG. 11: Results from GO analysis of the top 2000 protein groups by LFQ intensity, showing terms for cellular component (red), molecular function (orange), and biological process (grey) with associated $-\log_{10}$ (FDR) values and ratios of gene counts in network to background genes for the top ten highest −log 10 (FDR) terms in each category.

FIG. 19: Results of NanoSight nanoparticle tracking analysis for determination of vesicle size and concentration in exosomes obtained from a wild-type sample (top) and an alpha-5 integrin knockdown sample (bottom).

DETAILED DESCRIPTION OF THE INVENTION

The present invention describes a novel method for characterizing the biomolecule content of exosomes and other lipid vesicles. In particular embodiments, the present invention provides a method for characterizing the protein content of exosomes which achieves reproducible, deep coverage of the proteome. Use of photocleavable surfactants, such as 4-hexylphenylazosulfonate (Azo), enables greater sensitivity of exosome peptide and other biomolecule analysis in a shorter timeframe than conventional methods. In general, these methods show promise for application to the study of exosomes obtained from cells and other means, such as from biofluids.

EXAMPLES

Example 1—One-Pot Exosome Proteomics Enabled by a Photocleavable Surfactant

Exosomes are nano-sized extracellular vesicles (EVs) of endosomal origin ranging between 30 and 150 nm in diameter and package biomolecular markers reflecting the cells that secrete them.[1] The exchange of exosomal protein, nucleic acid, metabolite cargoes via exosome binding and uptake represents an increasingly recognized mechanism of intercellular communication.[2,3] Recently, exosome-mediated communication has attracted significant attention for its involvement in diseases such as cancer, cardiovascular dysfunction, and neurodegeneration.[4,5] Since exosomes are secreted by all cells and are present in all biological fluids, they represent attractive targets as minimally-invasive liquid biopsies to diagnose disease, understand disease progression, and serve as therapeutic drug delivery vehicles.[3,6]

Hence, it is important to develop robust techniques for the rapid and reproducible analysis of the biomolecules in exosomes.

Mass spectrometry (MS)-based proteomics is one of the most promising techniques for the global identification and quantification of proteins,[7,8] and has recently been employed to characterize exosomal protein cargoes.[1,9-14] Typically, bottom-up proteomic methods are used in these MS-based analyses of EVs, but the sample preparation typically involves the use of MS-incompatible detergents for protein extraction, overnight and/or multiple enzymatic digestions, and lengthy multidimensional chromatographic separations.[12-14] The elongated experimental time and complexity required to improve exosomal proteome coverage in these previously established methods significantly reduce the throughput and reproducibility, limiting the potential of MS-based proteomic analysis of exosomes in translational and clinical applications.

Figure 1:
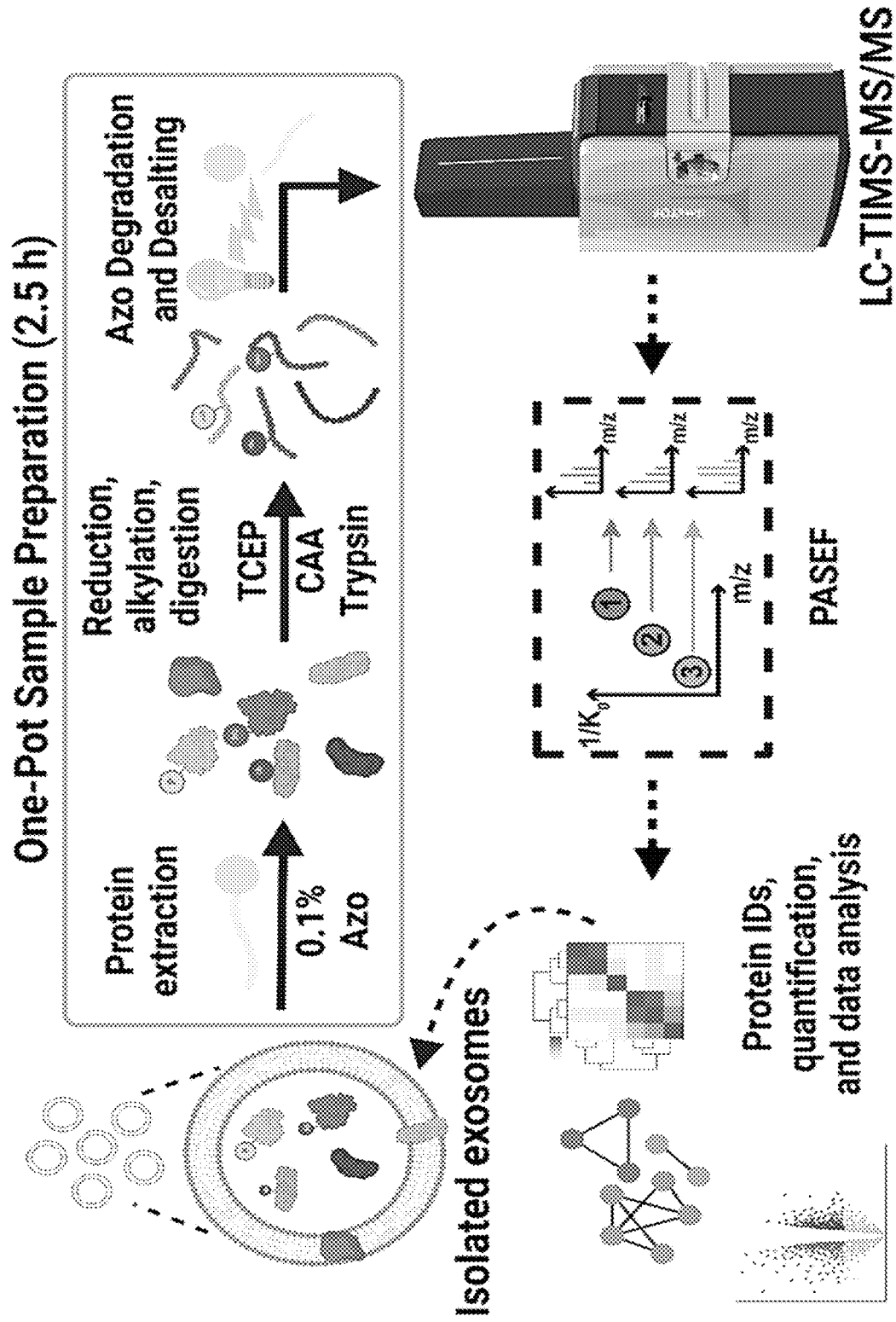
FIG. 1: Schematic representation of Azo-based exosome proteomics method in an embodiment of the invention. Exosomes are lysed and proteins extracted in 0.1% Azo. Proteins are reduced and alkylated simultaneously using TCEP and chloroacetamide, followed by Azo-aided rapid trypsin digestion (1 h). Resulting peptides are irradiated with a high-powered UV lamp for 5 min to degrade Azo, then samples are centrifuged and desalted before LC-TIMS-MS/MS analysis. The resulting data are searched with MSFragger and further analyzed using Perseus.

To overcome these limitations, a new method was developed for exosome proteomics with a one-pot preparation of exosomes using a photocleavable surfactant, Azo[15], to simplify protein extraction and expedite digestion (see FIG. 1). Azo has been previously shown to be comparable to SDS for complete cell lysis and global protein solubilization.[16] Azo is capable of extracting those extremely difficult to be solubilized proteins which cannot be completely solubilized in chaotropic agents such as urea, making it suitable to the task of exosomal lysis and protein extraction.[15-17]

After Azo-assisted digestion and surfactant photodegradation, the peptides are analyzed using trapped ion mobility spectrometry (TIMS)-quadrupole time-of-flight mass spectrometer (Bruker timsTOF Pro) with parallel accumulation-serial fragmentation (PASEF)[18] for improved sensitivity and coverage. Azo promotes protein solubilization including both membrane and extracellular matrix proteins, enables rapid digestion, and yields reproducible protein identification and quantitation.[15-17] Here, it is shown that Azo can be used to simultaneously lyse and extract proteins from exosome samples and then assist rapid trypsin digestion. Using this Azo-enabled method, exosome extraction and sample preparation require only ~2.5 h, compared to traditional methods employing overnight digestion and/or lengthy pre-fractionation that may take 16 to 24 h total.[12-14] Subsequent LC-TIMS-MS/MS analysis enhanced by PASEF improves sensitivity without increasing analysis time, obviating the need for multidimensional LC or prefractionation, and increasing the total number of proteins identified in the extraction.[19] This method has been applied to analyze mammary fibroblast-derived exosomes, a subtype which contributes to the pool of breast tumor exosomes which have previously shown involvement in breast cancer metastatic niche formation and growth.[11] This one-pot, photocleavable surfactant-assisted sample preparation is simple, rapid, and yields deep exosomal proteome coverage.

Figure 2:
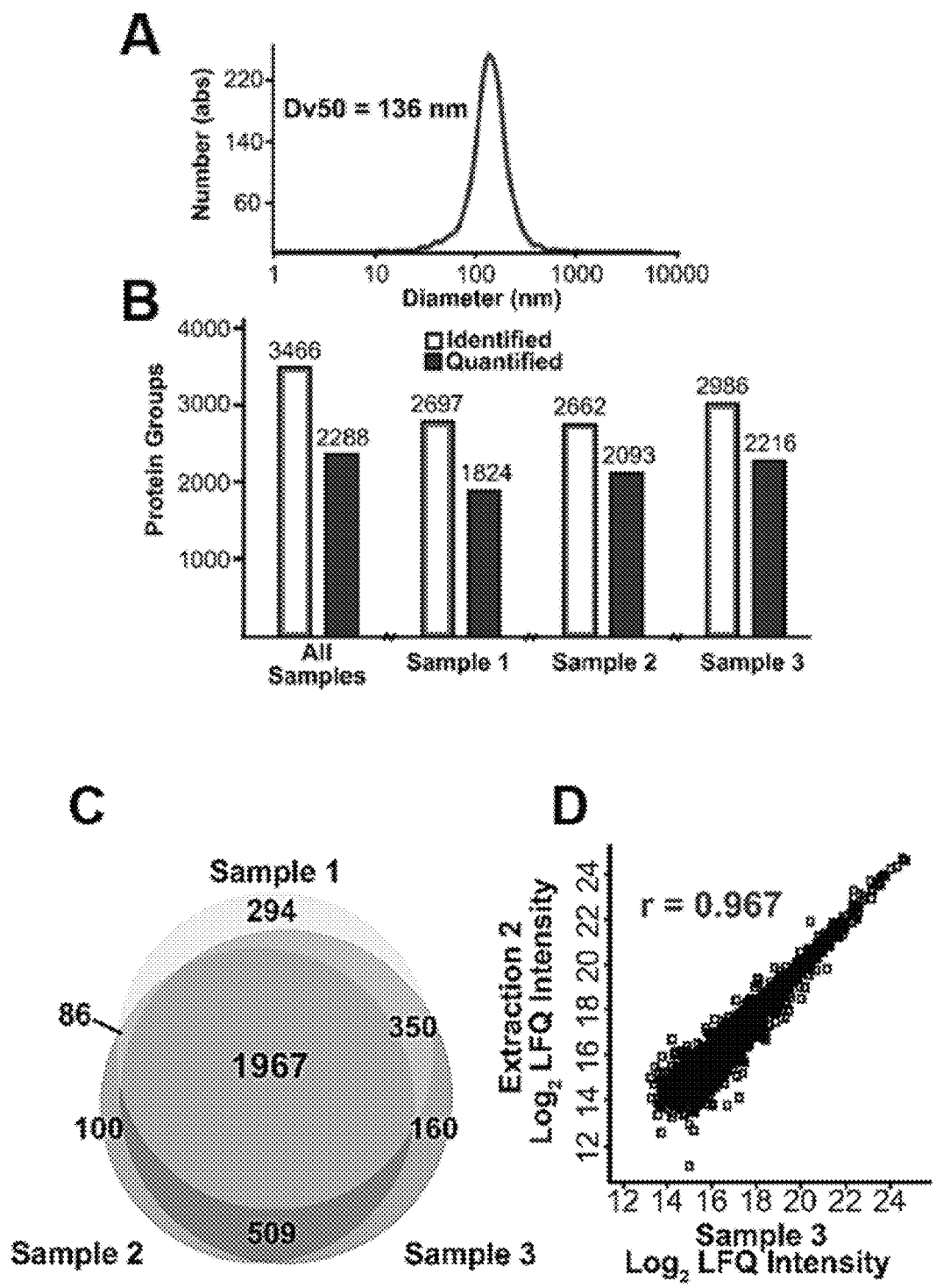
FIG. 2: Assessment of exosome isolation, method efficacy, reproducibility, and quantitation in three mammary fibroblast exosome samples. Panel A) Nanoparticle tracking analysis (NTA) results show a particle size distribution characteristic of exosome samples, with a Dv50 of 136 nm. Panel B) Bar graph showing protein groups identified with at least one unique peptide spectral match (PSM) and quantified in at least two samples. From all samples combined, 3,466 protein groups were identified and of those 2,288 were quantified in two of the three extractions. Panel C) Venn diagram showing 1,967 identified protein groups common to all three samples and 2,912 in at least two. Panel D) Representative scatter plot with associated Pearson correlation coefficient (PCC) depicting a pairwise relationship between log 2 transformed LFQ intensities of samples 2 and 3.
Figure 3:
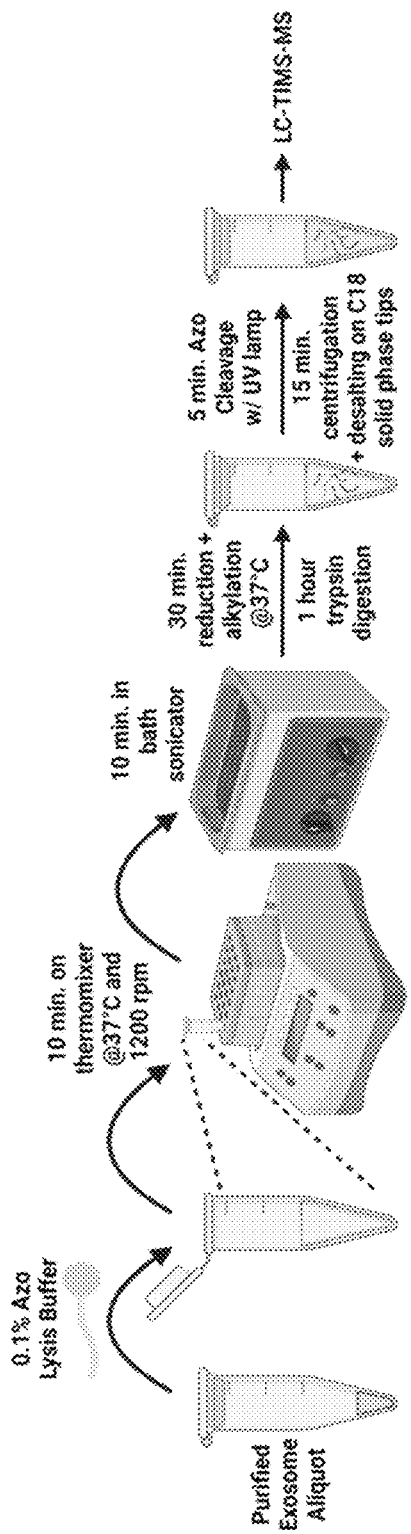
FIG. 3: Schematic representation of a one-pot sample preparation for a photocleavable surfactant, Azo-enabled exosome proteomics method. Exosomes are first treated with 0.1% Azo then placed on a thermomixer for 10 min at 37° C. to allow for protein extraction. This is followed by 10 min incubation in a bath sonicator to effectively lyse exosomal membranes. Next, samples are treated with TCEP and CAA for simultaneous reduction and alkylation, while incubating in a 37° C. water bath prior to trypsin digestion (1 h). Afterward, the surfactant is degraded by UV and sample cleanup proceeds following centrifugation.

Sample preparation and data acquisition. Exosomes were isolated from mammary fibroblasts by differential ultracentrifugation[20] and characterized by nanoparticle tracking analysis (NTA) with a Dv50 median particle diameter of 136 nm (50% of the sample exosomes by volume were below 136 nm in diameter) (FIG. 2, panel A). This size is consistent with the values of exosome and other small EV hydrodynamic diameters, as reported previously.[21] Exosome isolation methods vary across studies and offer differing balances between specificity, yield, and efficiency, though ultracentrifugation is the most common.[22] Isolated exosomes were aliquoted to microcentrifuge tubes or one-pot sample preparation (FIG. 3). Detailed sample preparation and data acquisition descriptions are provided further below.

Figure 4:
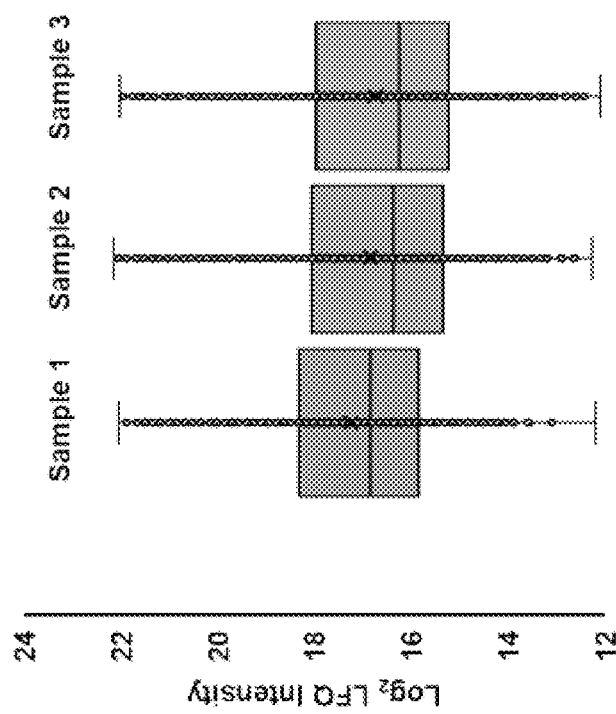
FIG. 4: Box and whisker plots showing ranges of log 2 normalized LFQ intensities, derived from median values from injection replicates three samples. Outliers are omitted and an exclusive median is used to calculate the ranges shown.
Figure 5:
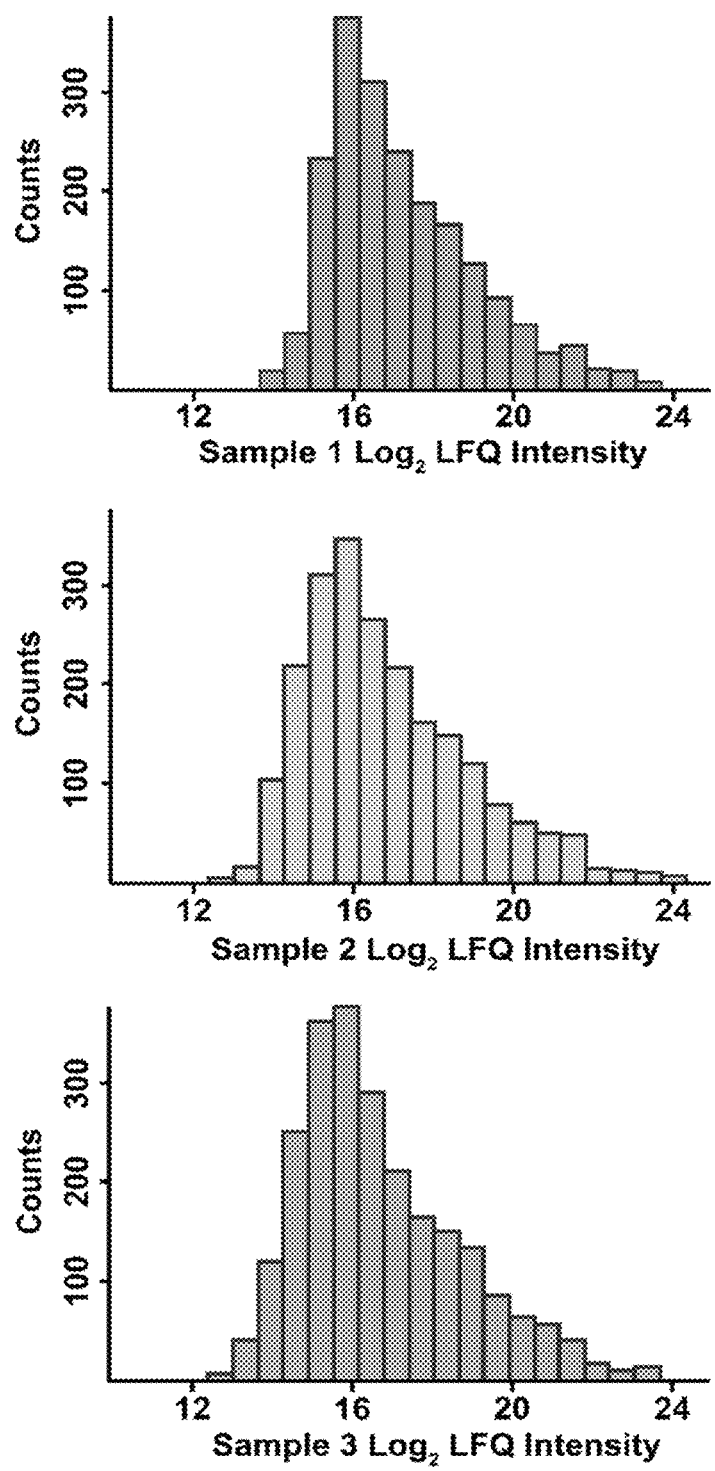
FIG. 5: Histogram showing normally-distributed counts of log 2 transformed LFQ intensities for median values taken from injection replicates for the three samples. Results demonstrate reproducible quantification.

Identification and label-free quantification (LFQ) following MS analysis were carried out using MSFragger (1% FDR) with IonQuant.[23] $\log_2$ transformed protein LFQ intensities from the three samples showed normally distributed values that spanned similar ranges, suggesting that the extractions were reproducible (FIGS. 4 and 5).

Figure 6:
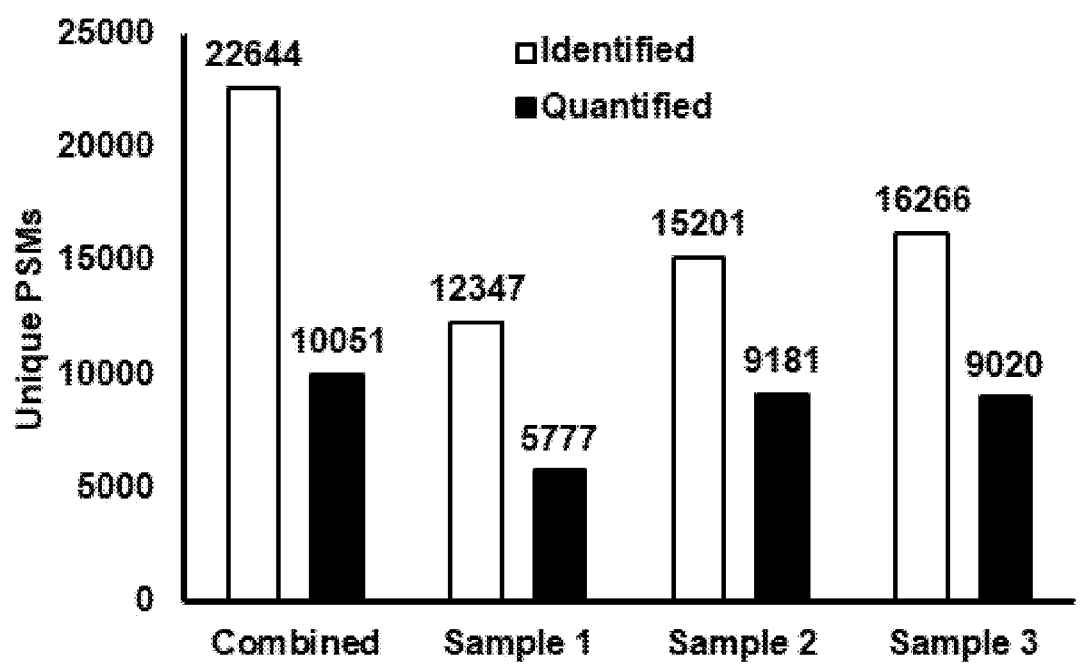
FIG. 6: Bar graph showing the number of unique peptide spectral matches (PSMs) identified in each sample (green) and the number of PSMs with valid LFQ intensities (purple) in two of three samples. For each sample, LFQ intensities were log 2 transformed and the median intensity for each PSM across injection replicates was used.

A total of 3,466 unique protein groups were identified across all samples and quantified 2,288 unique protein groups in at least two of three (FIG. 2, panel B). Disaggregated unique protein group counts for each sample and the corresponding number of quantified proteins match roughly with the unique peptides identified (FIG. 2, panel B and FIG. 6). For comparison, Rontogianni et al.[12] used 8 M urea to extract proteins for in-solution digestion and identified similar numbers (approximately 2,000 to 3,500) of protein groups in each of their ten cell lines, using 2 µg of peptides compared to the 200 ng used for the present analyses. Urea in-solution digestion is the most commonly used method in preparing exosome samples for proteomic analysis.[11-12,14] However, these urea-based methods suffer from possible protein carbamylation, require cleanup steps, and are less effective at solubilizing highly hydrophobic membrane proteins,[23] which is critical for exosomal analysis. A high degree of overlap in protein group identifications was observed across the present samples, with 1,967 protein groups being reliably identified in all three samples (FIG. 2, panel C).

To evaluate the quantitative reproducibility of this method, pairwise comparisons of $\log_2$ transformed LFQ intensities for samples were plotted against each other as scatter plots with associated Pearson correlation coefficients (PCCs).[18,24] The median LFQ intensity from injection replicates was used from each sample for the downstream analyses. Representative injection replicates for sample 3 showed highly correlated data with an average PCC of r=0.957, and the total ion chromatogram (TIC) of all three replicates remains consistent in intensity throughout the RPLC-MS analysis (FIG. 7). The scatter plots comparing samples show high correlations with PCCs off r=0.842, r=0.882, and r=0.967 with samples 2 and 3 compared in FIG. 2, panel D.

Figure 8:
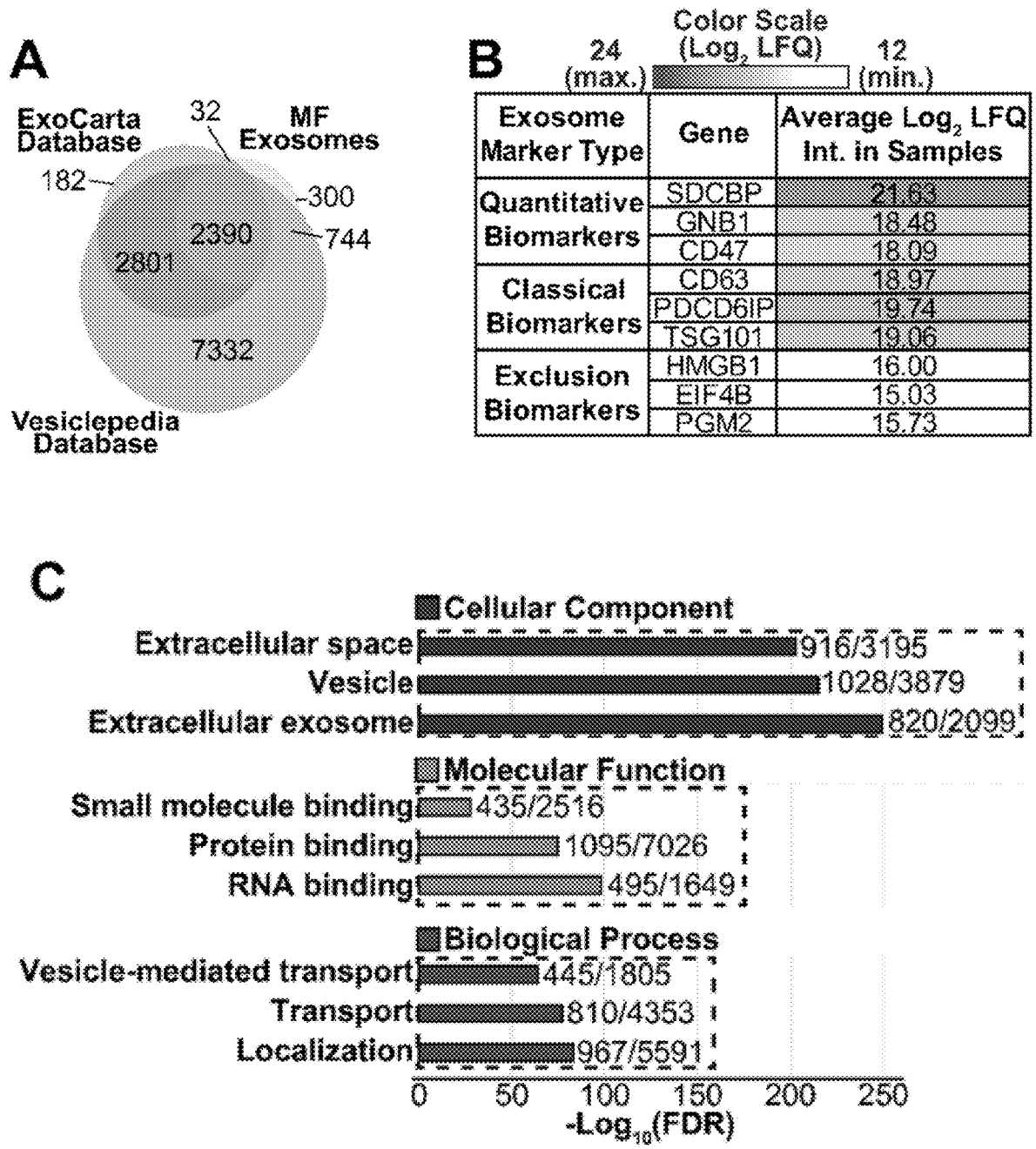
FIG. 8: Exosome proteomics results enabled by the Azo surfactant in an experiment. Panel A) Venn diagram showing the overlap between proteins identified from mammary fibroblast (MF) exosome samples (3466), ExoCarta (5324), and Vesiclepedia (13186). Panel B) Table showing classical, quantitative, and negative exosomal protein markers, color-scaled to overall range of observed LFQ intensities of the proteins in MF exosome samples. Panel C) Gene ontology results from STRING PPI analysis, shown grouped by cellular component, molecular function, and biological process, with corresponding −log 10 normalized false-discovery rates and the ratio of counts in the network to expected counts. Panel D) Zoom-in of STRING PPI network. Clusters show (left to right) aminoacyl-tRNA synthetases, spliceosome proteins, and a group of actin-related proteins.
Figure 8:
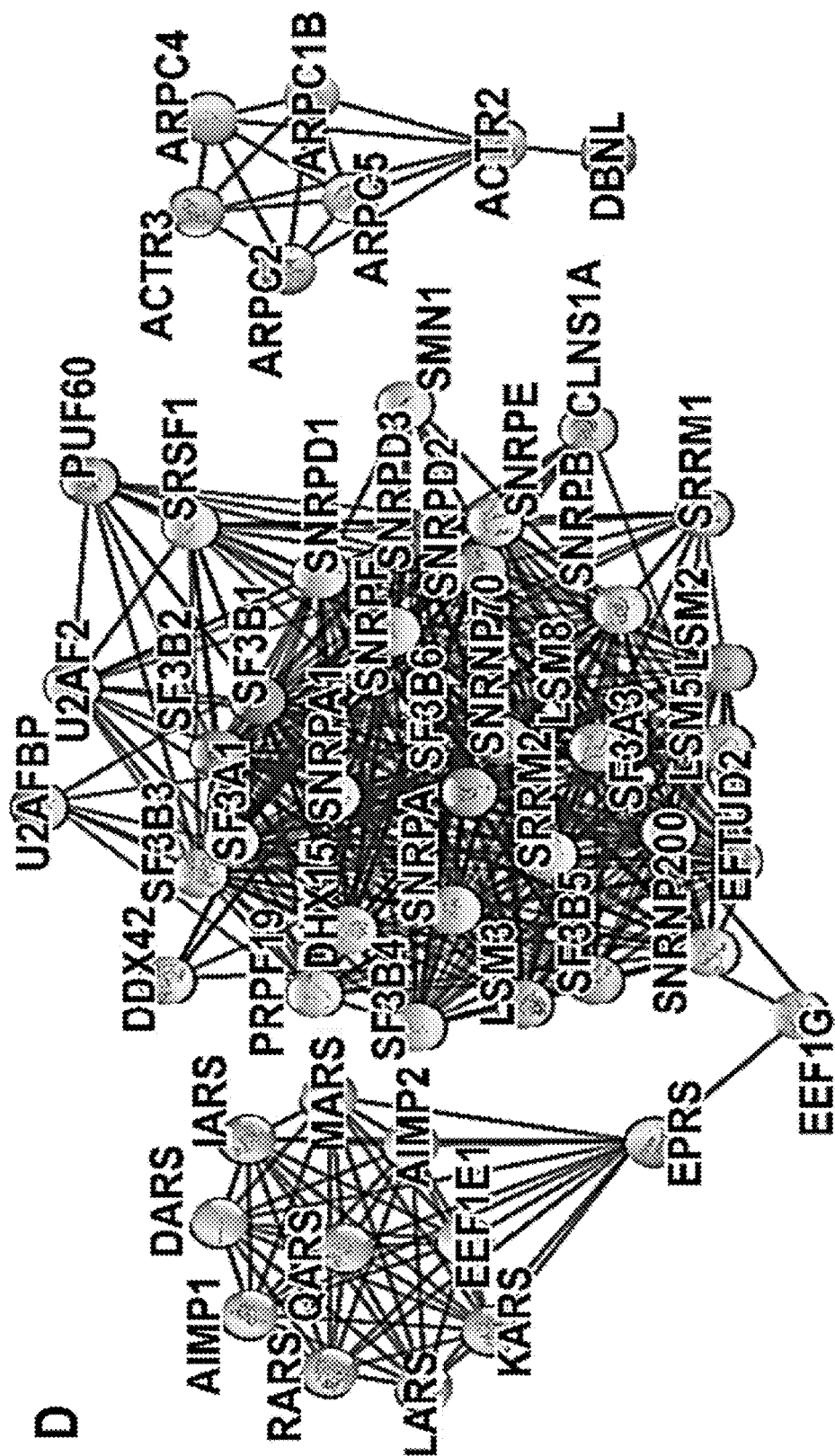

To benchmark the performance of this Azo-enabled method, all the identified protein groups from the samples were compared to those reported in ExoCarta,[25] a manually-curated online exosome database that collects proteins and nucleic acids identified in previous exosome studies for researchers to use, and Vesiclepedia,[26] which is similar but includes results from broader categories of EVs including microvesicles (FIG. 8). 3, 166 (91%) protein groups identified in this study from mammary fibroblast exosome samples are annotated in the ExoCarta and Vesiclepedia databases (FIG. 8, panel A). Among them, 2390 protein groups are annotated in both ExoCarta and Vesiclepedia databases, 32 annotated only in ExoCarta, and 744 annotated only in Vesiclepedia. This demonstrates the high quality of the exosome isolation and proteome coverage, 45% overlap with ExoCarta in proteins (2,422) using one cell line, despite the highly heterogeneous nature of exosome content.[6] In addition, the present samples showed generally high abundance based on normalized LFQ intensity of proteins from the ExoCarta top 100 list that collects the most frequently identified protein markers in exosomes (FIG. 9).

A small percentage (<9%) of the proteins identified in the Azo-extracted samples were not annotated in ExoCarta or Vesiclepedia. GO analysis of these proteins showed they were largely composed of histone proteins, ATP synthase subunits, and tRNA synthetases. Normalized LFQ intensities of these 300 proteins show their overall low abundance, especially compared to expected markers from ExoCarta and other previous studies (FIGS. 9 and 10). Given the low abundances of these proteins, it is possible that they are uniquely present in mammary fibroblast exosomes and have yet to be included in the database from previous studies, or are from residual cellular remnants.

Exosomal protein markers were further investigated by plotting the averaged, transformed LFQ intensities of specifically identified characteristic exosome protein markers (FIG. 8, panel B). A recent study of exosome heterogeneity showed the ubiquity of traditional[1] tetraspanin markers (CD9, CD81, CD63) to be questionable and proposed 22 quantitative high-abundance markers and 15 low-abundance "exclusion" markers. Three representative proteins were selected from each category of traditional, quantitative and exclusion markers to show their respective enrichment or depletion in the samples. The LFQ intensities for the exclusion markers in the samples fell below the lower quartile for all replicates and near the upper quartile for traditional and quantitative inclusion markers (FIG. 8, panel B and FIG. 4). These numbers are shown in FIG. 8, panel B with the color scaled to reflect the range of $\log_2$ LFQ intensities observed from the samples. The relative intensities of these specific positive and negative exosomal markers provide proteomic support for the purity of the exosome isolation.

Using STRING[27] network analysis, the interactions present in proteins identified from the samples were then assessed. The quantified protein groups showing the highest LFQ intensities across the replicates are shown in a protein-protein interaction network that showed an enrichment p-value of $<1.0\times10^{-16}$ indicating a significant enrichment. The resulting densely connected network contained clusters of interactors with relevant functional roles in exosomes, including aminoacyl-tRNA synthetases,[28] splicing factors and other spliceosome-associated proteins,[29] and actin-related proteins[30]. Specific proteins from these clusters have been plotted independently in FIG. 8, panel D.

Figure 12:
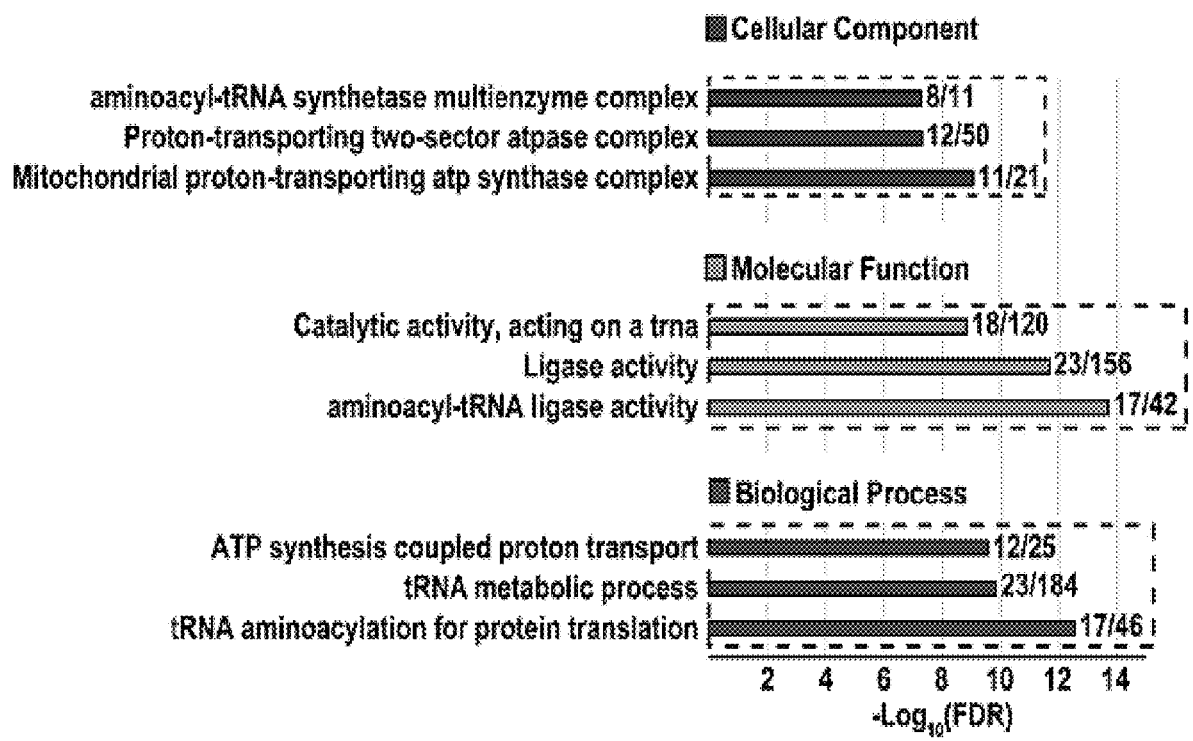
FIG. 12: GO analysis from STRING network of proteins identified in the mammary fibroblast-derived exosomes samples using the method which were not found in ExoCarta or Vesiclepedia databases. Plot shows top three GO cellular component, molecular function, and biological process terms by their $-\log_{10}$ (FDR) and the ratio of observed to background genes in the network. Of the 300 proteins identified in this study which are not annotated in either database, primary categories included ATP synthase subunits, tRNA ligases, and histones.

Further analysis was carried out using the built-in GO capability of STRING to display terms pertaining to the locations, processes, and functions of networked proteins along with their associated FDRs and ratio of gene counts in the network to expected counts (FIG. 8, panel D). The most confidently assigned cellular components from the GO analysis were all related to extracellular spaces or vesicles (FIG. 11). Additional gene ontology (GO) analysis of the proteins not currently annotated in either ExoCarta or Vesiclepedia is shown in FIG. 12.

Thus, in summary, an Azo-enabled exosome proteomics method was developed capable of one-pot exosome lysis and protein extraction to allow high-throughput sample processing and proteomic analysis. The use of Azo for effective protein extraction and rapid digestion before MS analysis expedites exosome sample preparation. Moreover, the use of TIMS front-end separation and PASEF provides high sensitivity MS/MS analysis for deep proteome coverage. Notably, 3,466 proteins were identified from mammary fibroblast exosome samples and 2,288 proteins were reliably quantified with high reproducibility. This one-pot Azo-enabled exosome method is simple, rapid, and robust, making it amenable for exosome proteomics in general. As a result, this method enables studies of exosomal protein cargoes to understand the role of exosomes in intercellular communication and accelerate the use of exosomes in therapeutic interventions and clinical diagnosis.

REFERENCES CITED IN EXAMPLE 1

(1) Kowal, J.; Arras, G.; Colombo, M.; Jouve, M.; Morath, J. P.; Primdal-Bengtson, B.; Dingli, F.; Loew, D.; Tkach, M.; Théry, C. Proteomic Comparison Defines Novel Markers to Characterize Heterogeneous Populations of Extracellular Vesicle Subtypes. *PNAS*. 2016, 113 (8), 968-977.

(2) Tkach, M.; Théry, C. Communication by Extracellular Vesicles: Where We Are and Where We Need to Go. *Cell*. 2016, 164 (6), 1226-1232.

(3) Raghu, K.; S, L. V. The Biology, Function, and Biomedical Applications of Exosomes. *Science* 2020, 367 (6478).

(4) Sahoo, S.; Adamiak, M.; Mathiyalagan, P.; Kenneweg, F.; Kafert-Kasting, S.; Thum, T. Therapeutic and Diagnostic Translation of Extracellular Vesicles in Cardiovascular Diseases. *Circulation*. 2021, 143 (14), 1426-1449.

(5) Budnik, V.; Ruiz-Cañada, C.; Wendler, F. Extracellular Vesicles Round off Communication in the Nervous System. *Nat. Rev. Neurosci.* 2016, 17 (3), 160-172.

(6) Ferguson, S. W.; Nguyen, J. Exosomes as Therapeutics: The Implications of Molecular Composition and Exosomal Heterogeneity. *J. Controlled Release*. 2016, 228, 179-190.

(7) Aebersold, R.; Mann, M. Mass-Spectrometric Exploration of Proteome Structure and Function. *Nature*. 2016, 537 (7620), 347-355.

(8) A. Melby, J.; S. Roberts, D.; J. Larson, E.; A. Brown, K.; F. Bayne, E.; Jin, S.; Ge, Y. Novel Strategies to Address the Challenges in Top-Down Proteomics. *J. Am. Soc. Mass Spectrom.* 2021, 32 (6), 1278-1294.

(9) Simpson, R. J.; Lim, J. W. E.; Moritz, R. L.; Mathivanan, S. Exosomes: Proteomic Insights and Diagnostic Potential. *Expert Rev. Proteomics*. 2009, 6 (3), 267-283.

(10) Trairak, P.; Rong-Fong, S.; A, K. M. Identification and Proteomic Profiling of Exosomes in Human Urine. *PNAS*. 2004, 101 (36), 13368-13373.

(11) Hoshino, A. et al. Tumour Exosome Integrins Determine Organotropic Metastasis. *Nature*. 2015, 527 (7578), 329-335.

(12) Rontogianni, S.; Synadaki, E.; Li, B.; Liefaard, M. C.; Lips, E. H.; Wesseling, J.; Wu, W.; Altelaar, M. Proteomic Profiling of Extracellular Vesicles Allows for Human Breast Cancer Subtyping. *Commun. Biol.* 2019, 2 (1), 325.

(13) Schey, K. L.; Luther, J. M.; Rose, K. L. Proteomics Characterization of Exosome Cargo. *Methods*. 2015, 87, 75-82.

(14) Kugeratski, F. G.; Hodge, K.; Lilla, S.; McAndrews, K. M.; Zhou, X.; Hwang, R. F.; Zanivan, S.; Kalluri, R. Quantitative Proteomics Identifies the Core Proteome of Exosomes with Syntenin-1 as the Highest Abundant Protein and a Putative Universal Biomarker. *Nat. Cell Biol.* 2021, 23 (6), 631-641.

(15) Brown, K. A.; Chen, B.; Guardado-Alvarez, T. M.; Lin, Z.; Hwang, L.; Ayaz-Guner, S.; Jin, S.; Ge, Y. A Photocleavable Surfactant for Top-down Proteomics. *Nat. Methods*. 2019, 16 (5), 417-420.

(16) Brown, K. A.; Tucholski, T.; Eken, C.; Knott, S.; Zhu, Y.; Jin, S.; Ge, Y. High-Throughput Proteomics Enabled by a Photocleavable Surfactant. *Angew. Chem., Int. Ed.* 2020, 59 (22), 8406-8410.

(17) Knott, S. J.: Brown, K. A.; Josyer, H.; Carr, A.; Inman, D.; Jin, S.; Friedl, A.; Ponik, S. M.; Ge, Y. Photocleavable Surfactant-Enabled Extracellular Matrix Proteomics. *Anal. Chem.* 2020, 92 (24), 15693-15698.

(18) Meier, F.; Brunner, A. D.; Koch, S.; Koch, H.; Lubeck, M.; Krause, M.; Goedecke, N.; Decker, J.; Kosinski, T.; Park, M. A.; Bache, N.; Hoerning, O.; Cox, J.; Rather, O.; Mann, M. Online Parallel Accumulation-Serial Fragmentation (PASEF) with a Novel Trapped Ion Mobility Mass Spectrometer. *Mol. Cell.* Proteomics. 2018, 17 (12), 2534-2545.

(19) Aballo, T. J.; Roberts, D. S.; Melby, J. A.; Buck, K. M.; Brown, K. A.; Ge, Y. Ultrafast and Reproducible Proteomics from Small Amounts of Heart Tissue Enabled by Azo and TimsTOF Pro. *J. Proteome Res.* 2021, 20 (8), 4203-4211.

(20) Sung, B. H.; Ketova, T.; Hoshino, D.; Zijlstra, A.; Weaver, A. M. Directional Cell Movement through Tissues Is Controlled by Exosome Secretion. *Nat. Comm.* 2015, 6 (1), 7164.

(21) Sokolova, V.; Ludwig, A. K.; Hornung, S.; Rotan, O.; Horn, P. A.; Epple, M.; Giebel, B. Characterisation of Exosomes Derived from Human Cells by Nanoparticle Tracking Analysis and Scanning Electron Microscopy. *Colloids Surf., B.* 2011, 87 (1), 146-150.

(22) Théry, C. et al. Minimal Information for Studies of Extracellular Vesicles 2018 (MISEV2018): A Position Statement of the International Society for Extracellular Vesicles and Update of the MISEV2014 Guidelines. *J. Extracell. Vesicles.* 2018, 7 (1), 1535750.

(23) Waas, M.; Bhattacharya, S.; Chuppa, S.; Wu, X.; R. Jensen, D.; Omasits, U.; Wollscheid, B.; F. Volkman, B.; R. Noon, K.; L. Gundry, R. Combine and Conquer: Surfactants, Solvents, and Chaotropes for Robust Mass Spectrometry Based Analyses of Membrane Proteins. *Analytical Chemistry* 2014, 86 (3), 1551-1559.

(24) Yu, F.; Haynes, S. E.; Teo, G. C.; Avtonomov, D. M.; Polasky, D. A.; Nesvizhskii, A. I. Fast Quantitative Analysis of TimsTOF PASEF Data with MSFragger and IonQuant. *Mol. Cell. Proteomics.* 2020, 19 (9), 1575-1585.

(25) Keerthikumar, S.; Chisanga, D.; Ariyaratne, D.; al Saffar, H.; Anand, S.; Zhao, K.; Samuel, M.; Pathan, M.; Jois, M.; Chilamkurti, N.; Gangoda, L.; Mathivanan, S. ExoCarta: A Web-Based Compendium of Exosomal Cargo. *J. Mol. Biol.* 2016, 428 (4), 688-692.

(26) Pathan, M.; Fonseka, P.; Chitti, S. v; Kang, T.; Sanwlani, R.; van Deun, J.; Hendrix, A.; Mathivanan, S. Vesiclepedia 2019: A Compendium of RNA, Proteins, Lipids and Metabolites in Extracellular Vesicles. *Nucleic Acids Res.* 2019, 47 (D1), D516-D519.

(27) Szklarczyk, D.; Gable, A. L.; Lyon, D.; Junge, A.; Wyder, S.; Huerta-Cepas, J.; Simonovic, M.; Doncheva, N. T.; Morris, J. H.; Bork, P.; Jensen, L. J.; Mering, C. von. STRING V11: Protein-Protein Association Networks with Increased Coverage, Supporting Functional Discovery in Genome-Wide Experimental Datasets. *Nucleic Acids Res.* 2019, 47 (D1), D607-D613.

(28) Kim, S. B.; Kim, H. R.; Park, M. C.; Cho, S.; Goughnour, P. C.; Han, D.; Yoon, I.; Kim, Y.; Kang, T.; Song, E.; Kim, P.; Choi, H.; Mun, J. Y.; Song, C.; Lee, S.; Jung, H. S.; Kim, S. Caspase-8 Controls the Secretion of Inflammatory Lysyl-TRNA Synthetase in Exosomes from Cancer Cells. *J. Cell Biol.* 2017, 216 (7), 2201-2216.

(29) Pavlyukov, M. S.; Yu, H.; Bastola, S.; Minata, M.; Shender, V. O.; Lee, Y.; Zhang, S.; Wang, J.; Komarova, S.; Wang, J.; Yamaguchi, S.; Alsheikh, H. A.; Shi, J.; Chen, D.; Mohyeldin, A.; Kim, S. H.; Shin, Y. J.; Anufrieva, K.; Evtushenko, E. G.; Antipova, N. v; Arapidi, G. P.; Govorun, V.; Pestov, N. B.; Shakhparonov, M. I.; Lee, L. J.; Nam, D. H.; Nakano, I. Apoptotic Cell-Derived Extracellular Vesicles Promote Malignancy of Glioblastoma Via Intercellular Transfer of Splicing Factors. *Cancer Cell.* 2018, 34 (1), 119-135.e10.

(30) Holliday, L. S.; Faria, L. P. de; Rody Jr, W. J. Actin and Actin-Associated Proteins in Extracellular Vesicles Shed by Osteoclasts. *Int. J. Mol. Sci.* 2019, 21 (1), 158.

Example 2—Methods and Materials Used in Example 1

Materials. All reagents were purchased from Millipore Sigma (St. Louis, MO, USA) and Fisher Scientific (Fair Lawn, NJ, USA) unless noted otherwise. All solutions were prepared with HPLC-grade water (Fisher Scientific). Trypsin Gold was purchased from Promega (Madison, WI, USA). Azo was synthesized in house as described previously.[1]

Exosome isolation. Cells were grown to 5 million per plate and cultured in OptiMEM for 48 h, after which conditioned media was collected. Media was centrifuged (CRB Optima Ultracentrifuge, SW32-Ti Rotor) at 300×g for 10 min to pellet cells, then 2000×g for 20 min and then 10,000×g for 30 min to pellet microvesicles. Vivacell concentrators were washed with 70 mL deionized water at 1000×g for 10 min, and 70 mL of the supernatant from the previous centrifugation was transferred to the filter. Concentrators were centrifuged for 8 min at 1000×g, the resulting flow-through was discarded, and additional supernatant was added to the concentrator. This process was repeated until all of the supernatant was transferred to the concentrator, and the final volume of concentrated material was approximately 12 mL.

12 mL of concentrated material was added to a 14×95 mm tube and spun at 100,000×g at 4° C. for 4 h (CRB Optima Ultracentrifuge, SW40 swinging rotor). The supernatant was removed and resuspended in 3 mL PBS. This resuspension was centrifuged at 100,000×g at 4° C. for 2 h in new tubes, and the resulting supernatant was then discarded. Pelleted exosomes were resuspended in 100 μL PBS and flash-frozen in 10 μL aliquots in liquid nitrogen for storage at −80° C. One aliquot was reserved for the characterization of exosome concentration and diameter using nanoparticle tracking analysis (Particle Metrix Zetaview).

Sample preparation. Exosome aliquots were thawed and dissolved in 0.1% working concentration of Azo (4-hexylphenylazosulfonate), 25 mM ammonium bicarbonate, and 1×HALT protease and phosphatase inhibitor cocktail. Aliquots were then placed on a thermoshaker at 37° C. and 600 rpm for 10 min. Samples were placed in a bath sonicator for 10 min and then normalization of protein concentration was performed using the Bradford assay. For reduction and alkylation of disulfide bonds, samples were treated simultaneously with 25 mM TCEP and 50 mM chloroacetamide (CAA)[2] and incubated at 37° C. and 600 rpm on a thermoshaker for 30 min, after which they were treated with 1 M ammonium bicarbonate to adjust pH to the active range for digestion (~8.5). Digestion was performed by treating samples with a 50:1 (w/w) protein:trypsin ratio and incubating them for an hour on a thermoshaker at 37° C. and 600 rpm.

Trypsin digestion was quenched by the addition of small volumes of neat formic acid to reduce sample pH to 2. UV degradation of Azo was then performed using a high-powered mercury lamp (Nikon housing with Nikon HB-10101AF power supply; Nikon) to irradiate samples for 10 min, after which they were spun down at 21,000×g for 15 min. To remove degradation products and other contaminating salts, 100 μL Pierce C18 tips were used according to the manufacturer's specifications, and the remaining peptides were resuspended in 0.1% formic acid. Peptide concentrations were determined using absorption at 205 nm from a NanoDrop, using the Scopes method to obtain the extinction coefficient used in the calculations.[3]

Data Acquisition. A Bruker timsTOF Pro trapped ion mobility Q-TOF instrument fitted with a captive-spray nano-ESI source and coupled to a nanoElute nanoflow LC was used for all analyses. In each analysis, 200 ng of peptides from exosomal digests was injected onto a C18 column (25 cm length, 75 µm inner diameter, 1.6 µm particle size, 120 Å pore size; IonOpticks). Separations were carried out at 55° C. using a stepwise gradient increasing from 2-85% of 0.1% formic acid in acetonitrile and decreasing percent of 0.1% formic acid in water.

To collect MS/MS spectra, the timsTOF Pro was operated in positive mode using DDA-PASEF (data-dependent acquisition parallel accumulation-serial fragmentation) with 10 PASEF MS/MS scans collected over a charge range of 0 to 5. Operating m/z was set between 100 and 1700 and a $1/k_0$ range of 0.6 to 1.6 (V·s/cm$^2$) was used with a polygonal mobility filter to exclude singly charged ions. TIMS ramp and accumulation times were set to maintain a 100% duty-cycle, with a ramp time of 100 ms and an accumulation time of 2 ms. Sample injection amounts were normalized by TIC intensity to 200 ng injections of K562 whole-cell lysate.

Data Analysis. Identification and protein quantification were performed using MSFragger with IonQuant.[4,5] For MSFragger searches, precursor mass tolerance was set to +/−20 ppm, and fragment mass tolerance was set to 20 ppm. A maximum of two missed trypsin cleavages were specified and peptide mass was set between 500 and 8,000 Da. For quantitation, default parameters for IonQuant within the FragPipe GUI were used, with match between runs (MBR) enabled. Imported search results were further analyzed in Perseus (ver. 1.1.15.0). After data were filtered for contaminants, values were Log$_2$ transformed, and plots were generated using the resulting LFQ intensities.

REFERENCES CITED IN EXAMPLE 2

(1) Brown, K. A.; Chen, B.; Guardado-Alvarez, T. M.; Lin, Z.; Hwang, L.; Ayaz-Guner, S.; Jin, S.; Ge, Y. A Photocleavable Surfactant for Top-down Proteomics. *Nature Methods* 2019, 16 (5), 417-420.
(2) Müller, T.; Winter, D. Systematic Evaluation of Protein Reduction and Alkylation Reveals Massive Unspecific Side Effects by Iodine-Containing Reagents. *Molecular & cellular proteomics: MCP* 2017, 16 (7), 1173-1187.
(3) Loughrey, S.; Mannion, J.; Matlock, B. A205 Performance on the NanoDrop One A205 Extinction Coefficients for Peptide and Protein Measurements; 2016.
(4) Yu, F.; Haynes, S. E.; Teo, G. C.; Avtonomov, D. M.; Polasky, D. A.; Nesvizhskii, A. I. Fast Quantitative Analysis of TimsTOF PASEF Data with MSFragger and IonQuant. *Molecular & cellular proteomics: MCP* 2020, 19 (9), 1575-1585.
(5) Yu, F.; Haynes, S. E.; Nesvizhskii, A. I. IonQuant Enables Accurate and Sensitive Label-Free Quantification With FDR-Controlled Match-Between-Runs. *Molecular & Cellular Proteomics* 2021, 20.

Example 3—RIPK3 is a Luminal Protein in Extracellular Vesicles that Enhances Lysosomal Exocytosis During Necroptosis RIPK3 mediated necrosis—or necroptosis—is associated with the release of biomolecules such as DNA, RNA, metabolomes, and proteins, that play pathological and homeostatic functions. One way in which biomolecules may be released is in membrane-bound vesicles called small extracellular vesicles (SEVs) which are under the autonomic control of cells. Recently, necroptosis and EV biogenesis machinery have been found to share a common factor—mixed lineage kinase like (MLKL). While during necroptosis, MLKL causes plasma membrane rupture when phosphorylated by RIPK3, it has now been identified as a moonlighting protein involved in the biogenesis of small and large EVs independent of necroptosis.

Despite this discovery, the mechanism behind RIPK3-MLKL dependent EV biogenesis remains poorly understood. To gain mechanistic insights into necroptosis and EV biogenesis, mass spectrometry-based proteomics was performed to identify the unique protein cargo found in SEVs released during the induction of RIPK3-mediated programmed necrosis. Using flow cytometry, it was found that there is an overall increase in the number of vesicles released by necroptotic cells and contain MLKL and RIPK3, among other necroptosis cargo. Further, MEFs from Rab27WT and Rab27DKO mice that have abrogated SEV release were unable to rescue SEV release during necroptosis. During necroptosis, SEVs are released via a lysosomal route of exocytosis in a calcium-dependent manner. The data suggests necroptosis is a special biological situation in which cells switch to a lysosomal mode of exocytosis and release RIPK3 carrying SEVs presumably as a mechanism to limit the membrane damaging events during necroptosis.

Activation of tumor necrosis factor receptors leads to intracellular responses such as inflammation and cell-death[1]. A dynamic balance of pro and anti-apoptotic factors determines whether cells survive or die. The receptor interacting protein kinase (RIP) family member RIPK1 plays a crucial role in this initial decision making[2]. Typically, ubiquitinated RIPK1 activates NF-kB and MAPK pathways that result in inflammatory cytokine production[3,4]. In contrast, de-ubiquitination of RIPK1 enables it to interact with apoptotic proteins such as caspase 8, leading to apoptotic cell death which is marked by an organized disintegration of cells[5,6]. However, another RIP family member RIPK3 can associate with RIPK1 when caspase 8 is absent or inhibited and leads to the execution of a form of regulated necrosis called necroptosis[7,8]. The association of RIPK3 with RIPK1 via RHIM-domain interaction and trans-autophosphorylation events that follow lead to RIPK3 activation[9]. Activated RIPK3 interacts with and phosphorylates a pseudokinase MLKL which translocates to the plasma membrane and ruptures it[10-12,12].

Even though intracellular signaling determines whether cells die by apoptosis or necroptosis, the latter is largely incomplete without the mechanical lysis of the plasma membrane. The dynamic process of exocytosis and endocytosis, by repairing the damaged plasma membrane, can alter the threshold at which cells can be defined as terminally necrotic[13-16]. Indeed, loss of MLKL can completely rescue necrosis even upon sustained activation of upstream signaling via RIPK1-RIPK3 by preventing lysis of the plasma membrane[17]. The delay in the lysis of the plasma membrane during necroptosis is likely to minimize the release of various intracellular molecules that can serve as damage-associated molecular patterns (DAMPs) and cause an inflammatory response[18].

Extracellular vesicles (EVs) are membrane-bound, micron to submicron-sized vesicles that are released from cells and have biological effects on their surroundings. A subset of these vesicles, called small EVs (SEVs), encompasses 30-200 nm-sized vesicles[19,20] some of which are produced via the endocytic machinery. Additionally, when these SEVs contain key cargo reflective of ongoing cellular events and are produced via the ESCRT pathway, these may be referred to as exosomes. The Rab family of proteins regulates many steps that are essential in vesicular trafficking such as formation, motility and fusion. These monomeric GTPase proteins shuttle between a GTP-bound active and GDP-bound inactive state. Specifically, Rab27A and Rab27B are widely known to promote distinct steps of SEV release from cells. New evidence also suggests that other routes of SEV exocytosis may co-exist with Rab27-mediated exocytosis. Other Rab proteins are essential for the upstream steps of SEV biogenesis. Towards this, the Rab11 family of proteins including Rab11A, Rab11B and Rab25 regulates many steps of MVB formation through recycling endosomes, a subset of which are essential for SEV formation. Curiously, the Rab11 family is found to be enriched in SEVs and has also been identified to interact with RIPK3 during necroptosis.

Recent work has highlighted that dying cells may generate extracellular vesicles such as exosomes that expel cargo that may otherwise compromise cellular integrity and may in turn serve as membrane-bound danger signals[21]. In this regard, necroptotic cell death is intriguing as cells not only generate extracellular vesicles during necroptosis but the effector protein MLKL is fundamental to the biogenesis of SEVs even in healthy cells[14,15]. Independent groups have demonstrated the role of MLKL in the endocytic and exocytotic mode of SEV biogenesis via the ESCRT complex. In both these processes, RIPK3 regulates the flux of SEV biogenesis.

The phosphorylation of MLKL by RIPK3 that causes its translocation to the plasma membrane is associated with the influx of calcium from the extracellular environment within the cell[10]. The phosphorylation of MLKL is a non-committal step in necroptosis as various "checkpoints" have been proposed which ensure that adequate opportunities are available for cells to repair membrane damage before necrosis[22]. As such, cells adopt numerous strategies to repair plasma membrane damage such as that caused during necroptosis. The influx of calcium from damaged plasma membrane is one such mechanism that can facilitate plasma membrane repair through a process called lysosomal exocytosis[23]. During lysosomal exocytosis, the fusion of the lysosomal membrane prevents further damage to the plasma membrane and is a calcium-dependent process. Ironically, MLKL appears to facilitate plasma membrane repair via calcium influx but is immediately cleared out from cells through extrusion in EVs or by internalization in lysosomes followed by its degradation[13]. Despite the key role of RIPK3 in phosphorylating MLKL, its involvement in the process of SEV biogenesis remains unknown.

Recently, mass spectrometry (MS)-based techniques have been utilized to profile metabolites, cytokines and proteins secreted from dying cells[21,26,27] including those factors secreted in EVs. The simultaneous assessment of post-translational modifications of proteins provides additional mechanistic insights that may be hard to garner from traditional assays.

The present examples assess the involvement of RIPK3 in extracellular vesicle generation during necroptosis and discover various unique characteristics of these necroptosis enhanced vesicles (NEEs). Using proteomics, the present examples further identify that the necroptotic components RIPK3 and MLKL are packaged inside these NEEs and provide mechanistic insights on how cells respond to necroptotic insult by adopting a lysosomal route of vesicle release to expel RIPK3 and MLKL.

Figure 13:
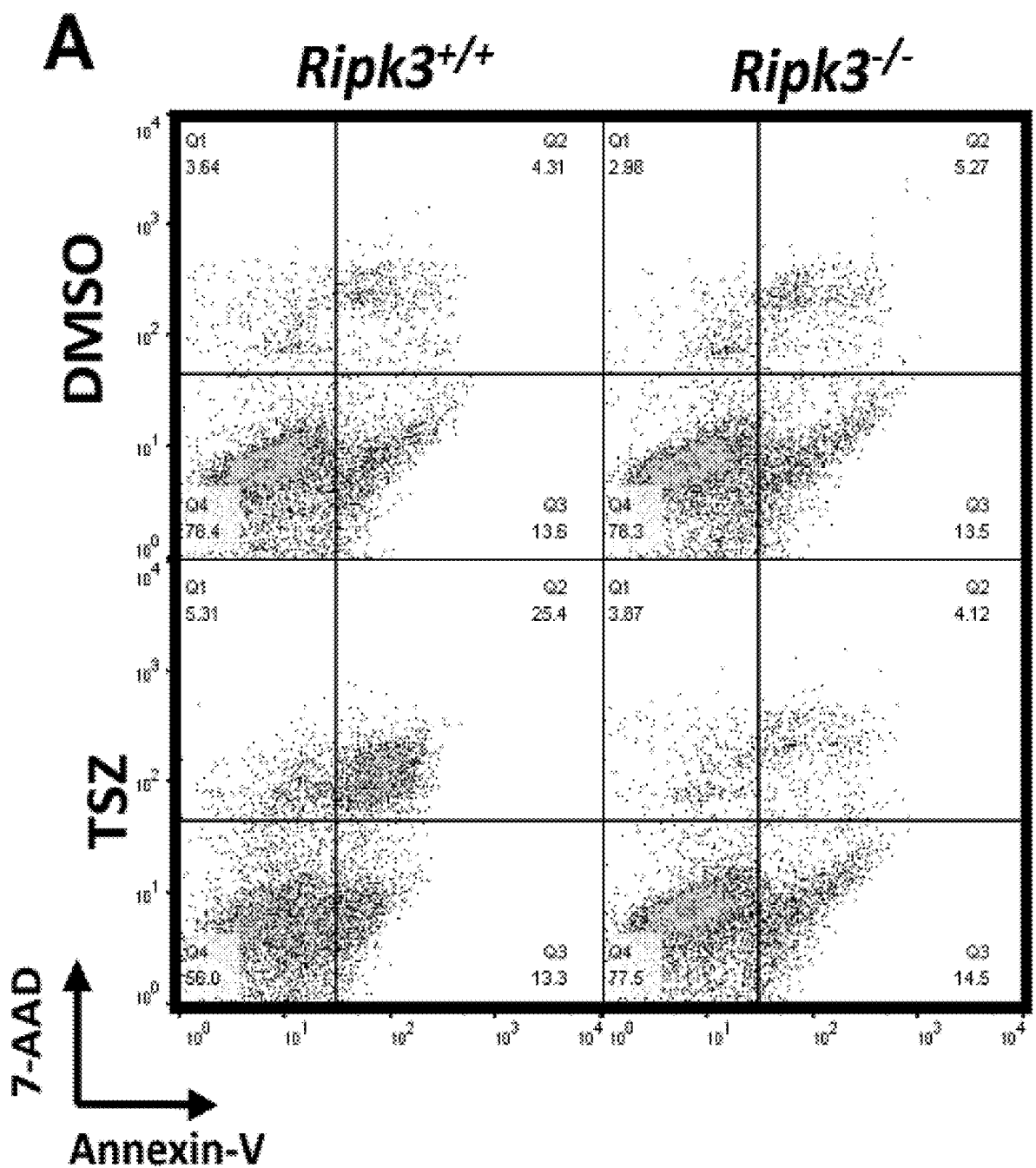
FIG. 13: Necroptotic cells release extracellular vesicles. Panel A) shows a representative scatter plot of Ripk3+/+ or Ripk3−/− MEFs treated with DMSO or TSZ where cell death is analyzed by flow cytometry. Panel B) presents representative traces of SEVs isolated from DMSO or TSZ treated Ripk3+/+ or Ripk3−/− MEFs isolated by ultracentrifugation and analyzed by NTA. Panel C) shows representative TEM images of SEV samples from Ripk3+/+ DMSO or TSZ treated MEFs fixed on carbon sputtered grids and labeled with uranyl acetate (scale bars=100 μm). Panels D, E) shows plots of particle size and number from NTA data, respectively.
Figure 13:
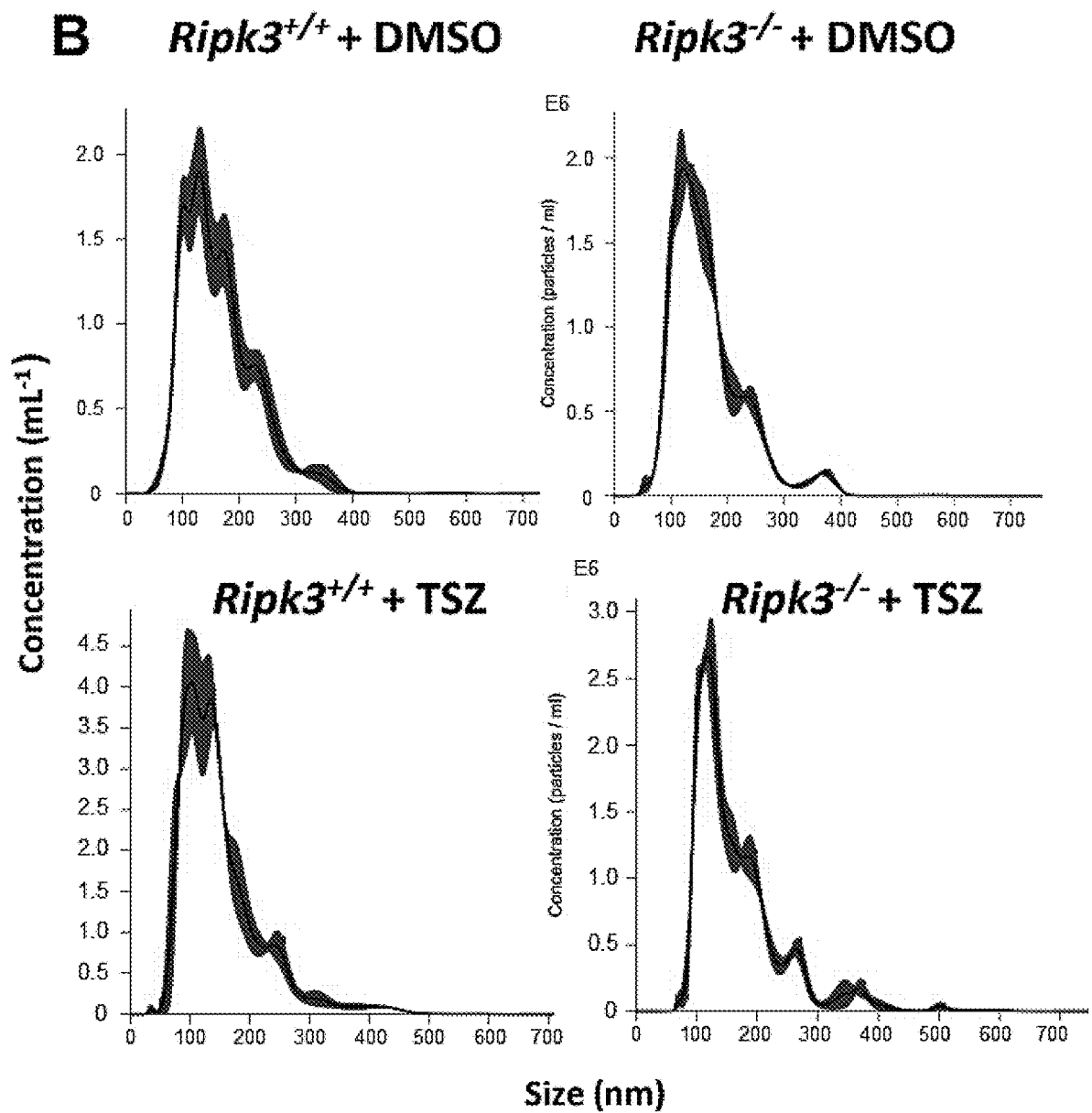
Figure 13:
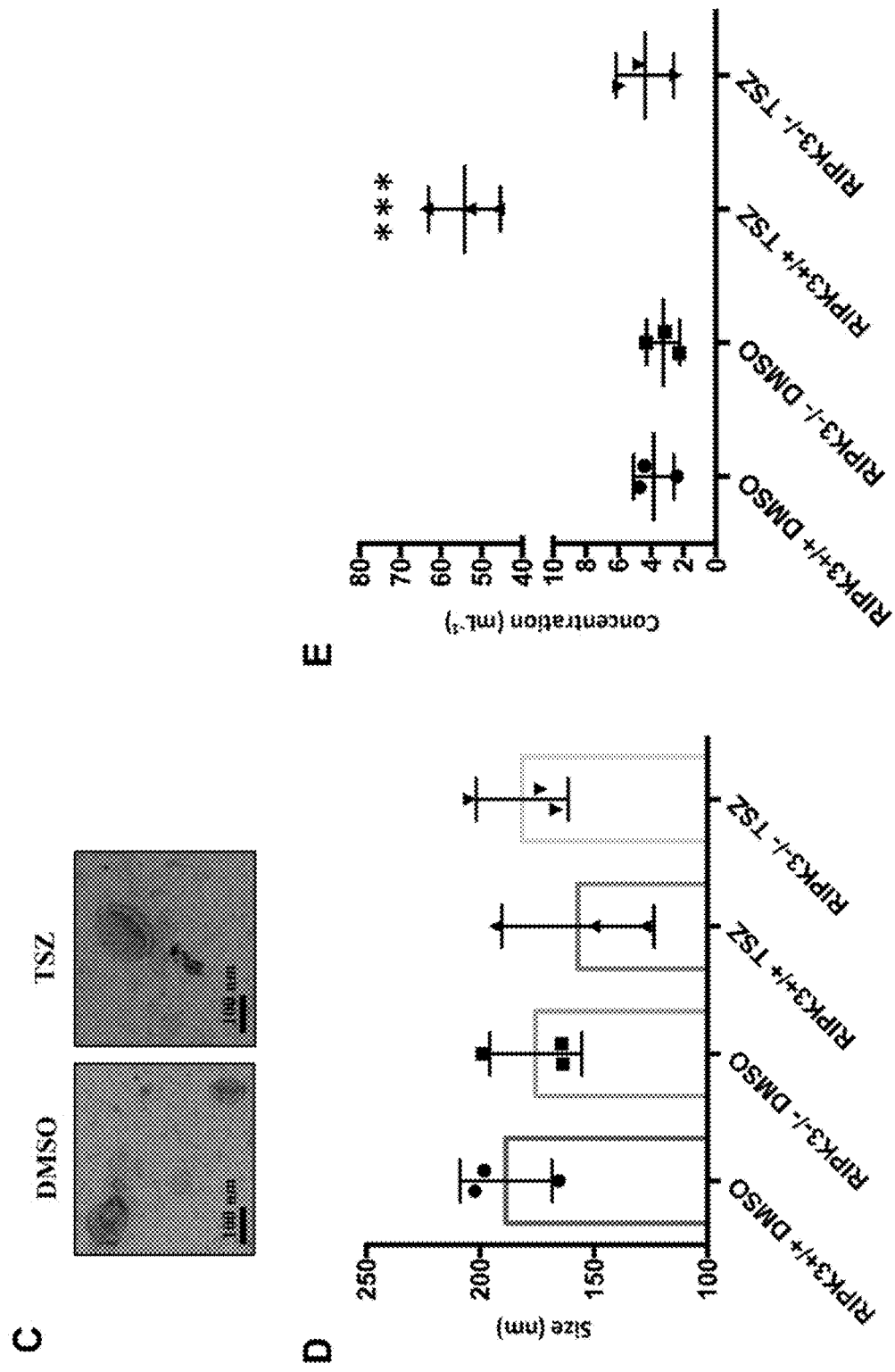

Extracellular Vesicles from Necroptotic cells are associated with increased vesicle number. Mouse embryonic fibroblasts (MEFs) derived from Ripk3+/+ or Ripk3−/− mice were treated with DMSO or with TNFα in the presence of Smac-mimetic and zVAD (hereafter referred to as TSZ) and necroptosis was measured. As expected, TSZ caused significant necrosis was in Ripk3+/+ MEFs (FIG. 13, panel A). Next, ultracentrifugation-based isolation was utilized to purify SEVs and characterized them using Nanoparticle Tracking Analysis (NTA) (FIG. 13, panel B) and transmission electron microscopy (TEM) (FIG. 13, panel C). The vesicles fit the size characteristics of small SEVs regardless of the treatment used (FIG. 13, panel D) and are hereby referred to as SEVs. Unexpectedly, necroptosis led to a dramatic increase in SEV numbers that was absent in SEVs released from Ripk3−/− MEFs stimulated with TSZ (FIG. 13, panel E), a finding consistent with other reports[15].

Figure 14:
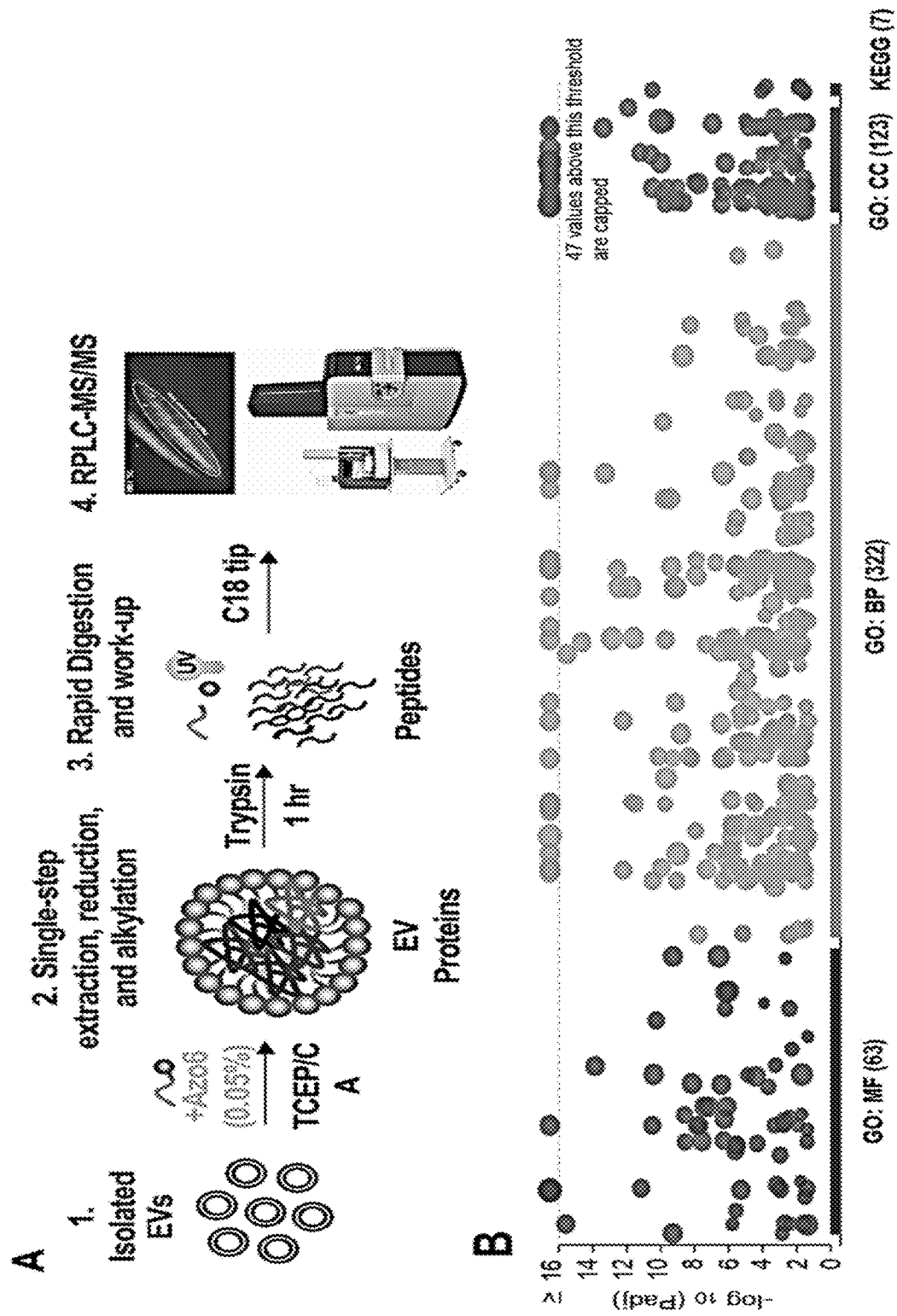
FIG. 14: Mass spectrometry analysis of NEEs. Panel A) shows a schematic representation of mass-spectrometry workflow in an embodiment of the present invention. Panels B, C) provide GO analysis performed using MF, BP, CC, KEGG and REAC databases. The cutoff for selected pathways is depicted in panel (B) and the pathways are represented in panel (C). In panel D), significantly enriched proteins from NEEs compared with the top 100 proteins available in the ExoCarta and Vesiclepedia databases and overlapping proteins are depicted in the Venn diagram.

Proteomic analysis of necrotic SEVs reveals known and novel protein cargo. Whether necroptosis alters protein cargos in SEVs is unknown. MS-based proteomics were utilized to assess the protein cargo inside SEVs released from health or necroptotic cells (FIG. 14, panel A). SEVs released by necroptotic cells contained more varieties of proteins than those released by healthy cells. In one experiment, 806 unique protein identification were found in the necroptotic cells, 10 unique proteins in the healthy, and 1062 shared. Next, various gene ontology enrichment analyses were performed on the protein cargo uniquely found in the SEVs released from necrotic cells (FIG. 14, panel B). Notably, it was found that these proteins had molecular functions such as RNA binding and protein binder were (FIG. 14, panel C). Proteins specifically found in the necrotic SEVs were involved in biological processes such as intracellular transportation and cellular localization. The necroptotic SEV-specific proteins were generally located in the cytosol, cytoplasm, intracellular anatomical structure, organelle, or vesicles, and analysis of their Reactome indicated involvement with the metabolism of RNA, membrane trafficking, and vesicle-mediated transportation. Overall, the GO enrichment analysis provided further evidence of the successful isolation and proteomic analysis of proteins belonging to SEVs which enabled the identification of the unique cargo belonging to necroptosis SEVs.

The protein cargo identified in the proteomic analysis were also compared with the top markers for SEV cargo available in ExoCarta and Vesiclepedia. 65 small SEV proteins were identified common among these and necrotic SEVs providing an internal validation for the isolation technique. In one experiment, approximately 1670 proteins were also found that were unique to NEEs (FIG. 14, panel D). Based on the characteristics of increased number and unique cargo, the SEVs secreted under necroptosis were termed as necroptosis enhanced SEVs (NEEs) to distinguish them from other SEVs.

Figure 15:
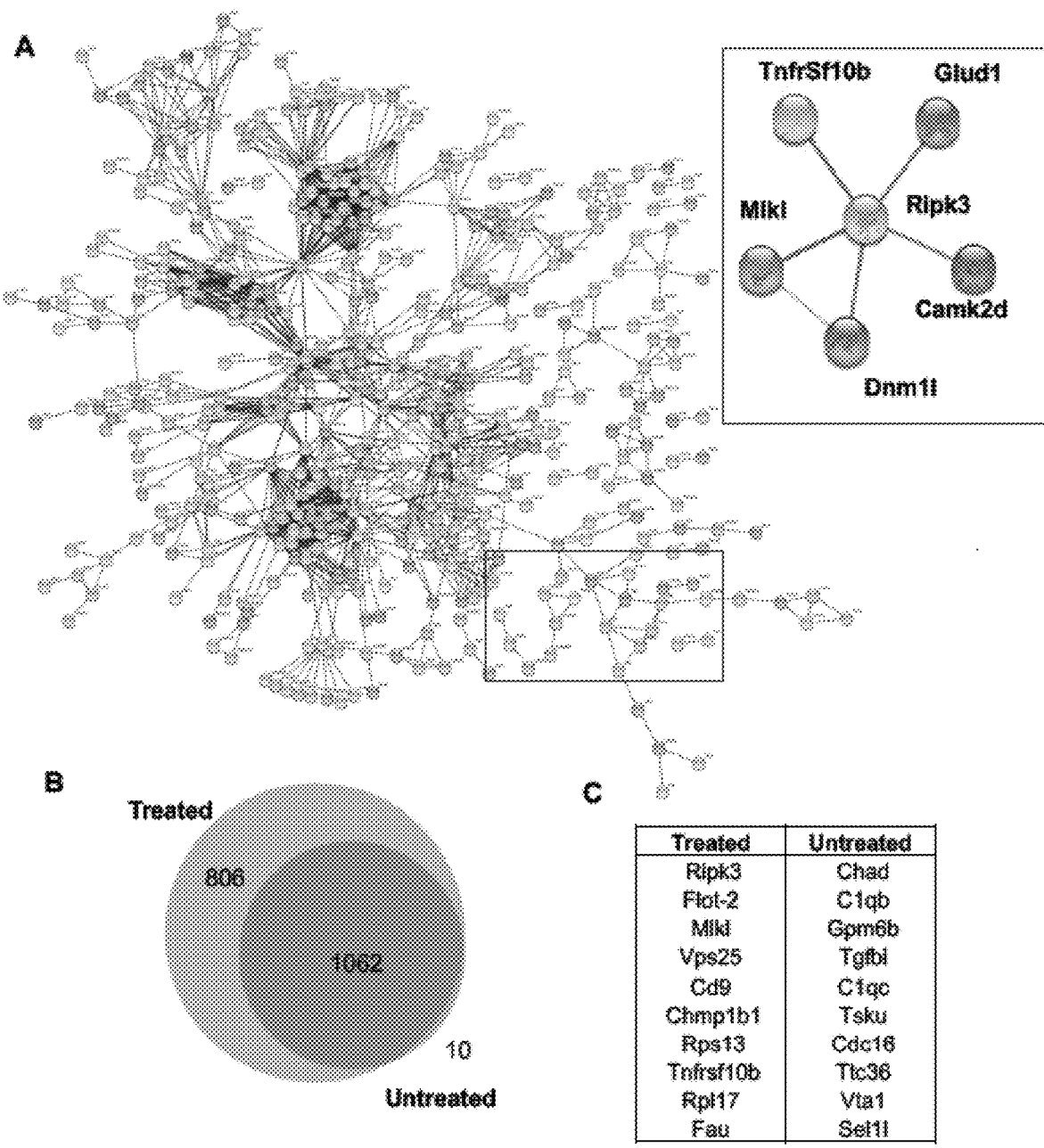
FIG. 15: NEEs are associated with RIPK3 and MLKL. SEVs are isolated from MEFs treated with DMSO or TSZ and analyzed by mass spectrometry. Panel A) presents an interactome generated from STRING analysis performed to ascertain known interactions in significantly enriched proteins in NEEs. Panel B) depicts a Venn diagram of significantly enriched proteins in SEVs isolated from treated and untreated cells. Panel C) depicts proteins pertinent to necroptosis and SEV biogenesis or function.

Necroptotic and lysosomal proteins are enriched in NEEs. Next, it was asked whether the pathway enrichment analysis is linked with a subset of proteins that share known biological interactions. STRING analysis was performed on the proteins found in NEEs which showed functional clustering of proteins that belong to common biological pathways such as signaling, protein secretion and cell death (FIG. 15, panel A). Further, NEEs shared 1062 proteins from the untreated condition but also contained 806 unique proteins (FIG. 15, panel B). Among these, it was found that numerous cell death proteins themselves enriched inside NEEs (FIG. 15, panel C). Curiously, the necroptotic proteins RIPK3 and MLKL were themselves enriches inside NEEs and are absent from other non-necroptotic SEVs. The presence of MLKL and various ESCRT members such as Vps25, Vps37, TSG-101 and Chmp1b1 specifically in SEVs was reported by others and is also found in NEEs suggesting common features associated with these necroptotic vesicles. To this end, the discovery of RIPK3 in NEEs is novel.

Figure 16:
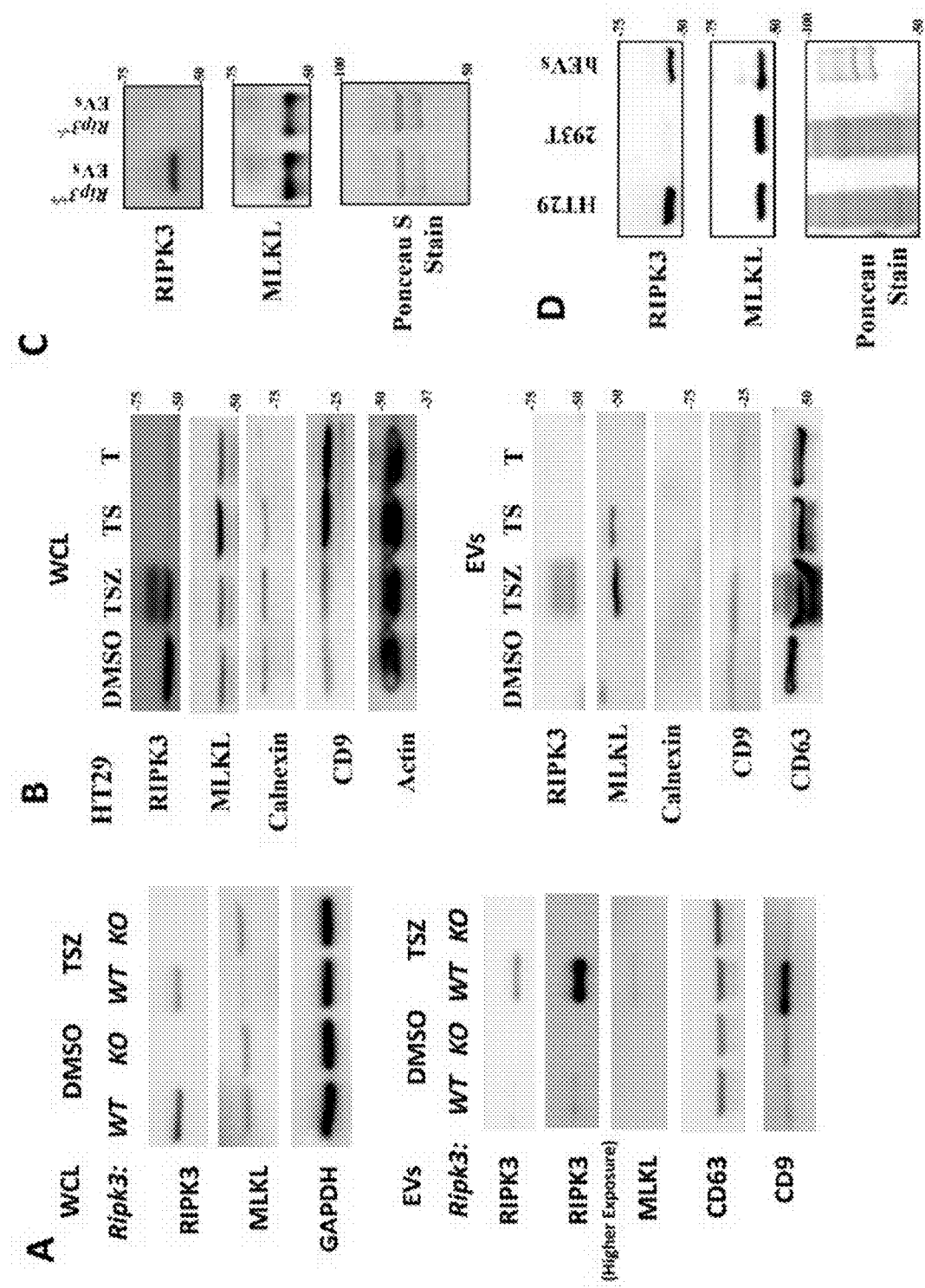
FIG. 16: RIPK3 is a luminal cargo protein in SEVs identifiable in diverse sources. Panel (A) shows Ripk3+/+ and Ripk3-/- treated with DMSO and TSZ. SEVs were isolated from cell culture and the cellular (top) and SEV fractions (bottom) were analyzed by western blotting. Panel (B) shows HT29 cells treated with DMSO, TSZ, TS or T as indicated. Whole cell extracts (top) and SEVs isolated from conditioned media (bottom) were analyzed via Western blotting. Panel C) shows SEVs isolated from Ripk3+/+ and Ripk3-/- mouse plasma and analyzed by western blotting for indicated proteins. Ponsceau S staining is used to ensure equal protein amounts. Panel D) shows SEVs from human plasma isolated and analyzed by western blotting. HT29 cells and 293T cells are used as positive and negative controls. Ponsceau S staining is used to ensure equal protein amounts. Panel E) shows SEVs derived from TSZ treated Ripk3+/+ MEFs treated with proteinase K along with indicated reagents (see methods section in corresponding examples) and analyzed by western blotting. CD63 is used as a non-liminal (transmembrane) protein control whereas GAPDH is used as a luminal protein control. Panels (F) and (G) show SEV samples from Ripk3+/+ DMSO or TSZ treated MEFs and human plasma fixed on carbon sputtered grids and processed for TEM images and analyzed by NTA.
Figure 16:
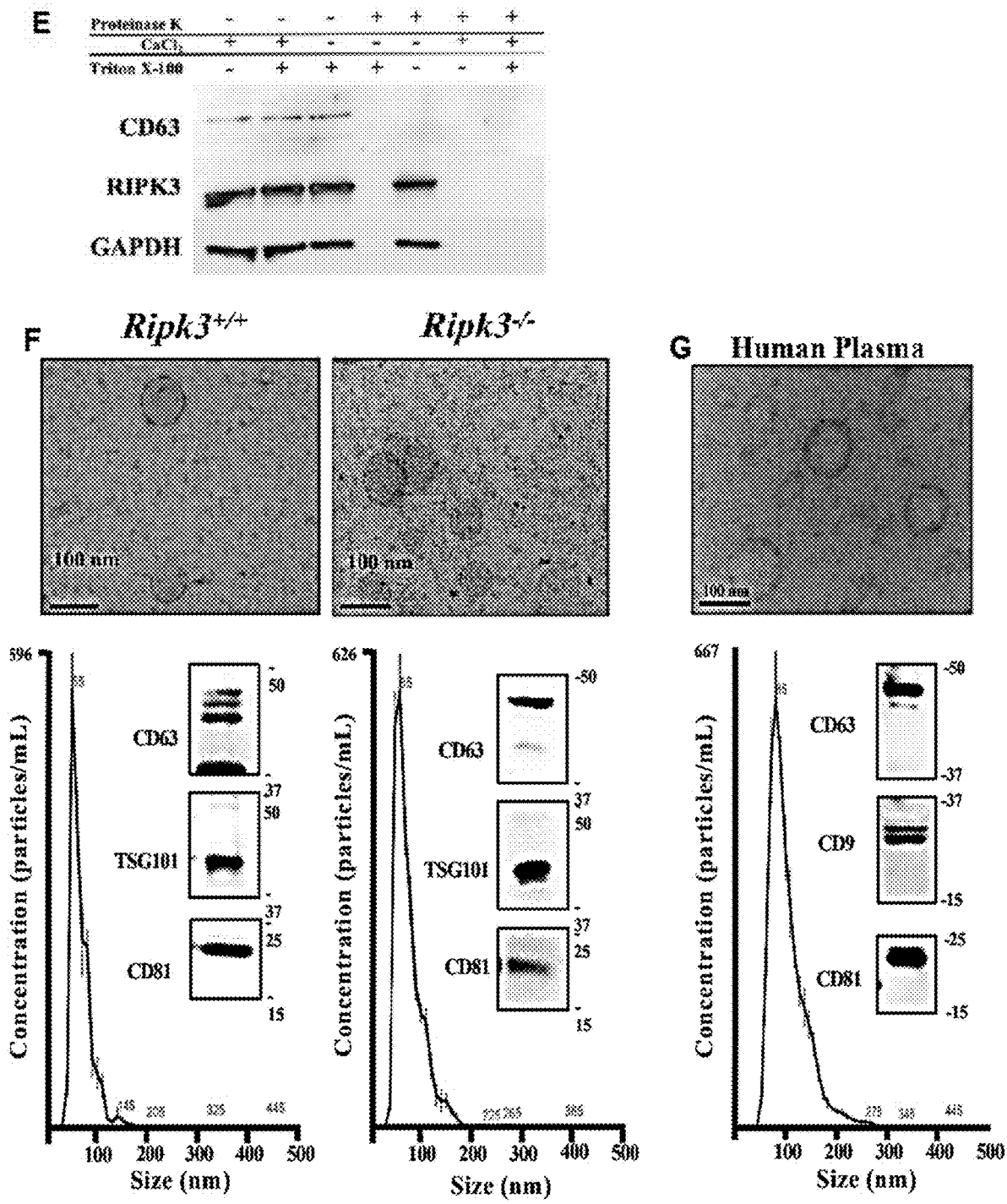

RIPK3 is a luminal cargo protein in NEEs and is present in diverse sources of SEVs. Next, western blot analysis was utilized for quantitative characterization of the necroptosis-specific protein cargo found in NEEs. Ripk3+/+ or Ripk3−/− MEFs were treated with DMSO or TSZ and western blotting was performed on whole cell lysate (WCL) and isolated SEVs. In agreement with mass spectrometry data, RIPK3 was specifically enriched in TSZ treated Ripk3+/+ MEFs (FIG. 16, panel A). Notably, a small fraction of RIPK3 was observed in SEVs isolated from DMSO-treated cells. Next, HT-29 cells—a commonly used human cell line in necroptosis assays—were utilized to test the assay for necroptosis-specific RIPK3 incorporation in SEVs in a cell line of human origin.

As expected, RIPK3 was specifically enriched in SEVs from TSZ treated HT29 cells but not in TS or T treated cells alone (FIG. 16, panel B), indicating necroptosis-specific RIPK3 incorporation in SEVs. SEVs from Ripk3+/+ or Ripk3−/− mice and human plasma were also isolated and characterized and found RIPK3 in SEVs (FIG. 16, panels C, D, F and G). The sub-vesicular localization of RIPK3 and utilized proteinase K protection assay, a commonly utilized technique28, were then assayed for this. As controls, GAPDH (a previously reported luminal SEV protein) and CD63 (a transmembrane protein) (FIG. 16, panel E) were used. As expected, RIPK3 was "protected" against Proteinase K-dependent proteolytic cleavage but was degraded in the presence of Triton-X100 which disrupts the vesicles. Since RIPK3 and MLKL were both found to be in NEEs, it was asked whether calcium can also result in proteinase K access to RIPK3. It was found that $CaCl_2$) led to a loss of protection against proteinase K. Together, it was identified that RIPK3 is found in the lumen of SEVs and is released in response to calcium.

Figure 17:
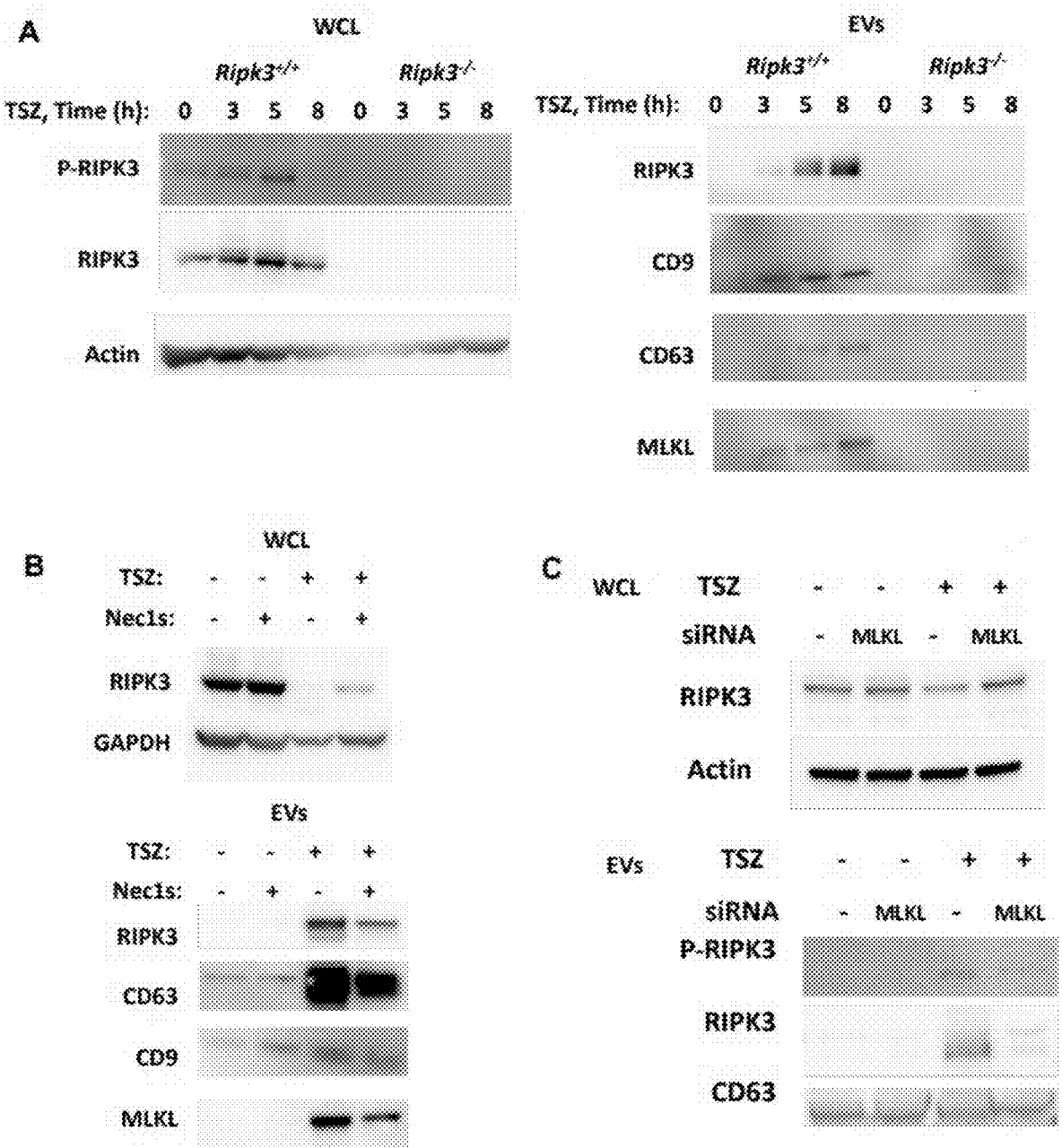
FIG. 17: RIPK3 packaging coincides with its pro-necrotic phosphorylation and dependent on MLKL. Panel A) shows Ripk3+/+ and Ripk3-/- treated with DMSO and TSZ for indicated times. SEVs are isolated and Western blotting is performed on the whole cell lysate (WCL, left) and SEVs (right). Panel B) shows Ripk3+/+ MEFs pretreated with DMSO or Nec1s and subsequently by DMSO or TSZ. SEVs are isolated using ultracentrifugation. Western blotting is performed on WCL (up) and SEVs (below). Panel C) shows siRNA mediated knockdown performed on MEFs for Control of MLKL. Necroptosis was induced using TSZ and SEVs are isolated. Western blot analysis is performed on WCL (up) and SEVs (below).

Necroptotic phosphorylation of RIPK3 is associated with NEE incorporation and is dependent on MLKL. RIPK3 is extensively regulated via key phosphorylation events and their impact on necroptosis regulation has been well characterized. The commercially available RIPK3 phospho T231/S232 antibody was first utilized to test the correlation between RIPK3 phosphorylation and SEV incorporation. As expected, there is a time-dependent increase in RIPK3 incorporation in SEVs that also correlated with its phosphorylation; at 8 h, a substantial fraction of RIPK3 was found in SEVs (FIG. 17, panel A). It was then observed that inhibiting upstream activation of RIPK3 by Nec1s can attenuate its SEV packaging and "locks" RIPK3 inside the cells (FIG. 17, panel B). siRNA was then used against MLKL to test whether RIPK3 incorporation inside SEVs depends upon MLKL. It was observed that MLKL knockdown, similar to Nec1s, prevents RIPK3 release inside SEVs (FIG. 17, panel C); however, it is unclear whether this decrease is due to MLKL's role in SEV biogenesis or cell-rupture.

Figure 18:
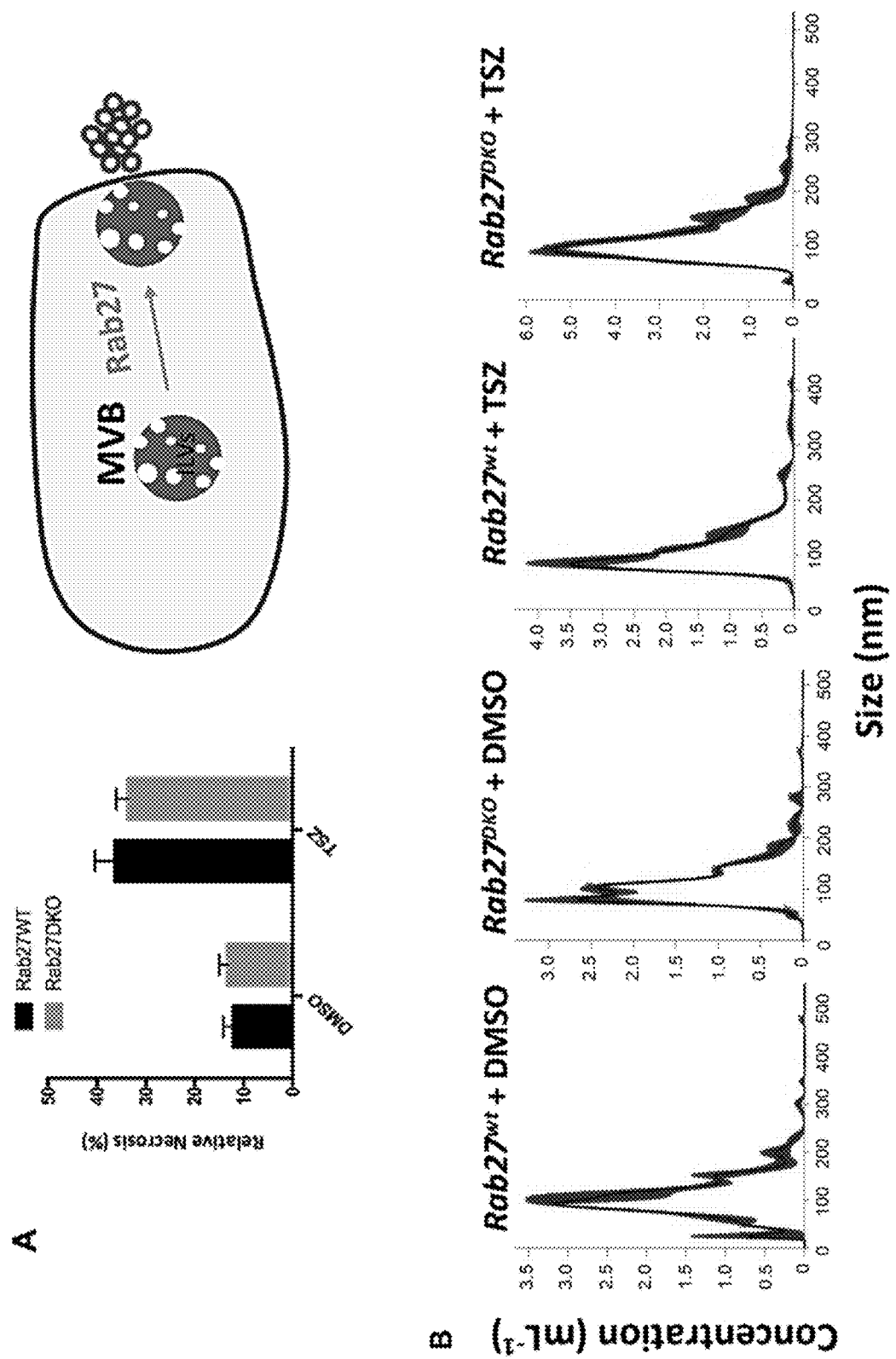
FIG. 18: Necroptotic EVs and RIPK3 secretion are independent of Rab27a and b. Panel A) shows that no significant differences in cell death in Rab27WT and Rab27DKO MEFs were observed in response to TSZ treatment. As shown in panel B), SEVs from these cells were isolated and subjected them to NTA analysis for SEV concentration and size. As expected, SEVs derived from Rab27DKO MEFs showed reduced SEV numbers when compared with WT cells (shown in panel C)). As shown in panel D), no size differences were observed among Rab27DKO and WT groups regardless of the treatment. Western blot analysis was then performed on the WCL and SEVs and found that although RIPK3 in SEVs is attenuated when derived from Rab27DKO relative to Rab27WT, RIPK3 levels remained unchanged between SEVs derived from Rab27WT and Rab27DKO cells treated with TSZ (shown in panel E)).
Figure 18:
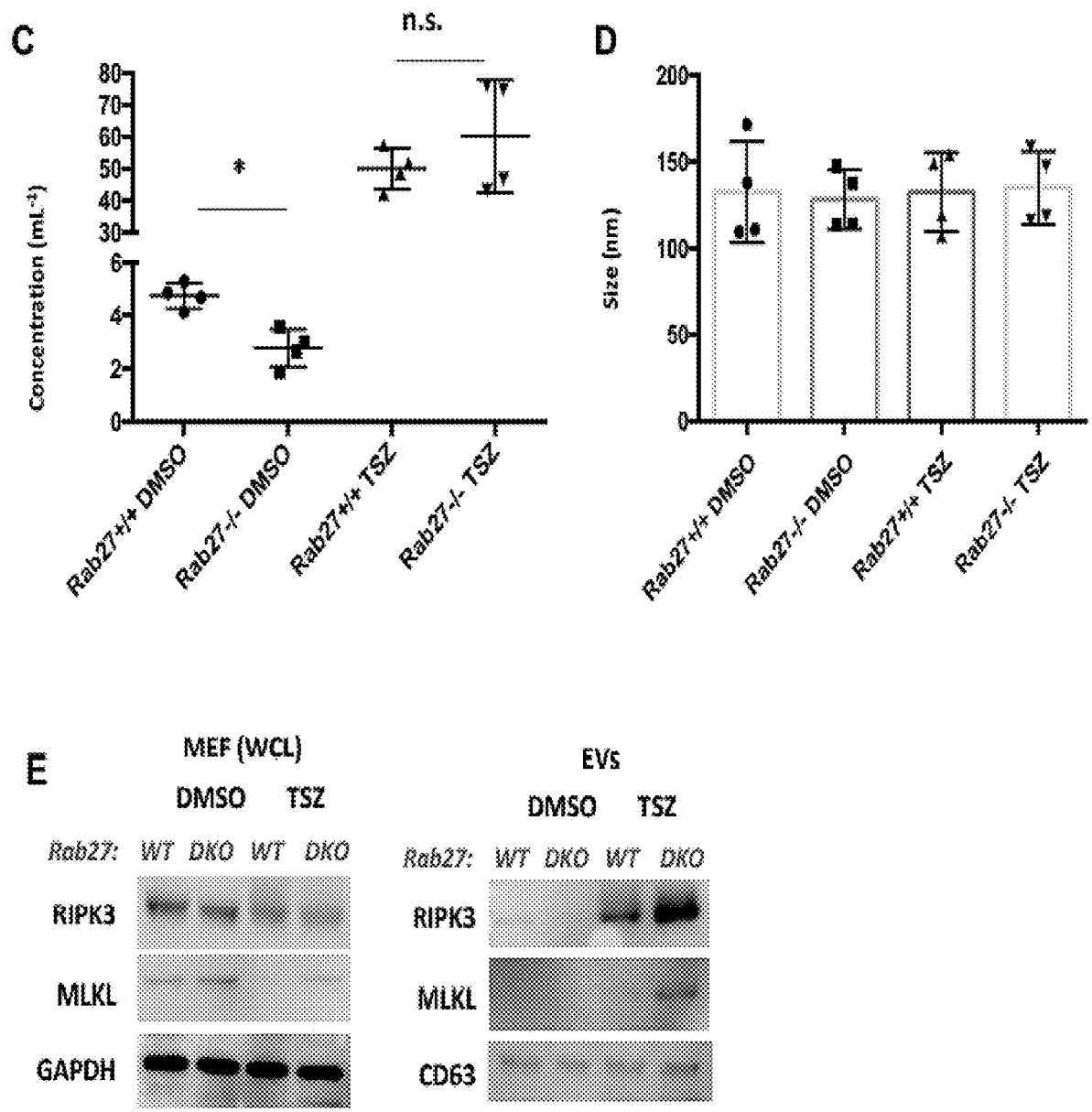

NEE Release during necroptosis is independent of Rab27A and Rab27B. The Rab27 family members RAB27A and B are reported to be involved in exosome release by fusion to the plasma membrane[29]. It was tested whether the release of RIPK3 in SEVs is dependent on Rab27 and procured Rab27A and B double knock out (Rab27DKO) mice. MEFs isolated from Rab27WT or Rab27DKO mice were then subjected to DMSO or TSZ treatment and analyzed cell death. No significant differences in cell death in Rab27WT and Rab27DKO MEFs were observed in response to TSZ treatment (FIG. 18, panel A). Next, SEVs from these cells were isolated and subjected them to NTA analysis (FIG. 18, panel B) for SEV concentration and size. As expected, SEVs derived from Rab27DKO MEFs showed reduced SEV numbers when compared with WT cells (FIG. 18, panel C). Unexpectedly, SEVs isolated from Rab27DKO TSZ treated cells bore no difference in SEV numbers when compared to Rab27WT, although both groups recapitulated an increase in SEV number in response to TSZ treatment. It was then tested whether the loss of Rab27-dependent SEV regulation in TSZ treatment was linked to an alteration in the type of small SEVs produced and measured the size of these SEVs. As shown, no size differences were observed among the Rab27DKO and WT groups regardless of the treatment (FIG. 18, panel D). Western blot analysis was then performed on the WCL and SEVs and found that although RIPK3 in SEVs is attenuated when derived from Rab27DKO relative to Rab27WT, in agreement with the NTA data, RIPK3 levels remained unchanged between SEVs derived from Rab27WT and Rab27DKO cells treated with TSZ (FIG. 18, panel E).

Discussion During necroptosis, an increase in the production of EVs is known to occur[15]. In contrast to an artifact of cell-lysis typical of necrosis, SEV biogenesis during necroptosis is a well-orchestrated process. Due to its link to necroptosis, the discovery of MLKL in SEV biogenesis partly describes the mechanism of production of these necroptotic SEVs; however, MLKL can also regulate SEV biogenesis in cells naturally lacking RIPK315 and independent of necroptosis induction. In the current examples, it was identified that RIPK3 might be more fundamentally involved in the mechanism of generation of these necroptotic SEVs and may redirect the mode of SEV release through MLKL-mediated calcium influx and activation of lysosomal exocytosis.

In this example, it was demonstrated that SEVs produced by necroptotic cells differ in their number and protein cargo but not in their mean size. Further, it was identified using mass spectrometry that these SEVs contain RIPK3 and resemble MLKL carrying vesicles defined previously during necroptosis. To indicate their unique nature such as increased number and cargo proteins, they are called NEEs. Rather than an artifact of cellular debris, NEEs contain RIPK3 (in addition to MLKL) in their lumen, which may indicate the mechanism by which these SEVs are generated and their functional importance. Using SEVs derived from Rab27WT Rab27DKO MEFs, it was observed that the endosomal machinery, typically attenuated upon Rab27 loss, also abrogated baseline RIPK3 packaging inside SEVs. In contrast, during necroptosis, the loss of Rab27 had no effect on the heightened RIPK3 packaging inside SEVs, suggesting that RIPK3's extrusion may occur via two different modes depending on its phosphorylation. Regardless, loss of MLKL rescues RIPK3 inside SEVs and NEEs.

REFERENCES IN EXAMPLE 3

(1) Sedger, L. M.; McDermott, M. F. TNF and TNF-Receptors: From Mediators of Cell Death and Inflammation to Therapeutic Giants—Past, Present and Future. Cytokine Growth Factor Rev. 2014, 25 (4), 453-472.

(2) Hsu, H.; Huang, J.; Shu, H. B.; Baichwal, V.; Goeddel, D. V. TNF-Dependent Recruitment of the Protein Kinase RIP to the TNF Receptor-1 Signaling Complex. Immunity 1996, 4 (4), 387-396.

(3) Kanayama, A.; Seth, R. B.; Sun, L.; Ea, C. K.; Hong, M.; Shaito, A.; Chiu, Y. H.; Deng, L.; Chen, Z. J. TAB2 and TAB3 Activate the NF-KB Pathway through Binding to Polyubiquitin Chains. Mol. Cell 2004, 15 (4), 535-548.

(4) Ea, C. K.; Deng, L.; Xia, Z. P.; Pineda, G.; Chen, Z. J. Activation of IKK by TNFα Requires Site-Specific Ubiquitination of RIP1 and Polyubiquitin Binding by NEMO. Mol. Cell 2006, 22 (2), 245-257.

(5) Kist, M.; Kömüves, L. G.; Goncharov, T.; Dugger, D. L.; Yu, C.; Roose-Girma, M.; Newton, K.; Webster, J. D.; Vucic, D. Impaired RIPK1 Ubiquitination Sensitizes Mice to TNF Toxicity and Inflammatory Cell Death. Cell Death Differ. 2020, 1-16.

(6) Zhang, X.; Zhang, H.; Xu, C.; Li, X.; Li, M.; Wu, X.; Pu, W.; Zhou, B.; Wang, H.; Li, D.; Ding, Q.; Ying, H.; Wang, H.; Zhang, H. Ubiquitination of RIPK1 Suppresses Programmed Cell Death by Regulating RIPK1 Kinase Activation during Embryogenesis. Nat. Commun. 2019, 10 (1), 4158.

(7) He, S.; Wang, L.; Miao, L.; Wang, T.; Du, F.; Zhao, L.; Wang, X. Receptor Interacting Protein Kinase-3 Determines Cellular Necrotic Response to TNF-α. Cell 2009, 137 (6), 1100-1111.

(8) Cho, Y. S.; Challa, S.; Moquin, D.; Genga, R.; Ray, T. D.; Guildford, M.; Chan, F. K. M. Phosphorylation-Driven Assembly of the RIP1-RIP3 Complex Regulates Programmed Necrosis and Virus-Induced Inflammation. Cell 2009, 137 (6), 1112-1123.

(9) Sun, X.; Yin, J.; Starovasnik, M. A.; Fairbrother, W. J.; Dixit, V. M. Identification of a Novel Homotypic Interaction Motif Required for the Phosphorylation of Receptor-Interacting Protein (RIP) by RIP3. J. Biol. Chem. 2002, 277 (11), 9505-9511.

(10) Cai, Z.; Jitkaew, S.; Zhao, J.; Chiang, H. C.; Choksi, S.; Liu, J.; Ward, Y.; Wu, L.; Liu, Z. G. Plasma Membrane Translocation of Trimerized MLKL Protein Is Required for TNF-Induced Necroptosis. Nat. Cell Biol. 2014, 16 (1), 55-65.

(11) Hildebrand, J. M.; Tanzer, M. C.; Lucet, I. S.; Young, S. N.; Spall, S. K.; Sharma, P.; Pierotti, C.; Garnier, J. M.; Dobson, R. C. J.; Webb, A. I.; Tripaydonis, A.; Babon, J. J.; Mulcair, M. D.; Scanlon, M. J.; Alexander, W. S.; Wilks, A. F.; Czabotar, P. E.; Lessene, G.; Murphy, J. M.; Silke, J. Activation of the Pseudokinase MLKL Unleashes the Four-Helix Bundle Domain to Induce Membrane Localization and Necroptotic Cell Death. Proc. Natl. Acad. Sci. 2014, 111 (42), 15072-15077.

(12) Su, L.; Quade, B.; Wang, H.; Sun, L.; Wang, X.; Rizo, J. A Plug Release Mechanism for Membrane Permeation by MLKL. Struct. Lond. Engl. 1993 2014, 22 (10), 1489-1500.

(13) Fan, W.; Guo, J.; Gao, B.; Zhang, W.; Ling, L.; Xu, T.; Pan, C.; Li, L.; Chen, S.; Wang, H.; Zhang, J.; Wang, X. Flotillin-Mediated Endocytosis and ALIX-Syntenin-1-Mediated Exocytosis Protect the Cell Membrane from Damage Caused by Necroptosis. Sci. Signal. 2019, 12 (583).

(14) Gong, Y. N.; Guy, C.; Olauson, H.; Becker, J. U.; Yang, M.; Fitzgerald, P.; Linkermann, A.; Green, D. R. ESCRT-III Acts Downstream of MLKL to Regulate Necroptotic Cell Death and Its Consequences. Cell 2017, 169 (2), 286-300.e16.

(15) Yoon, S.; Kovalenko, A.; Bogdanov, K.; Wallach, D. MLKL, the Protein That Mediates Necroptosis, Also Regulates Endosomal Trafficking and Extracellular Vesicle Generation. Immunity 2017, 47 (1), 51-65.e7.

(16) Zargarian, S.; Shlomovitz, I.; Erlich, Z.; Hourizadeh, A.; Ofir-Birin, Y.; Croker, B. A.; Regev-Rudzki, N.; Edry-Botzer, L.; Gerlic, M. Phosphatidylserine Externalization, "Necroptotic Bodies" Release, and Phagocytosis during Necroptosis. PLOS Biol. 2017, 15 (6), e2002711.

(17) Wu, J.; Huang, Z.; Ren, J.; Zhang, Z.; He, P.; Li, Y.; Ma, J.; Chen, W.; Zhang, Y.; Zhou, X.; Yang, Z.; Wu, S. Q.; Chen, L.; Han, J. Mlkl Knockout Mice Demonstrate the Indispensable Role of Mlkl in Necroptosis. Cell Res. 2013, 23 (8), 994-1006.

(18) Rock, K. L.; Kono, H. The Inflammatory Response to Cell Death. Annu. Rev. Pathol. 2008, 3, 99-126.

(19) Harmati, M.; Gyukity-Sebestyen, E.; Dobra, G.; Janovak, L.; Dekany, I.; Saydam, O.; Hunyadi-Gulyas, E.; Nagy, I.; Farkas, A.; Pankotai, T.; Ujfaludi, Z.; Horvath, P.; Piccinini, F.; Kovacs, M.; Biro, T.; Buzas, K. Small Extracellular Vesicles Convey the Stress-Induced Adaptive Responses of Melanoma Cells. Sci. Rep. 2019, 9 (1), 15329.

(20) Walbrecq, G.; Margue, C.; Behrmann, I.; Kreis, S. Distinct Cargos of Small Extracellular Vesicles Derived from Hypoxic Cells and Their Effect on Cancer Cells. Int. J. Mol. Sci. 2020, 21 (14).

(21) Tanzer, M. C.; Frauenstein, A.; Stafford, C. A.; Phulphagar, K.; Mann, M.; Meissner, F. Quantitative and Dynamic Catalogs of Proteins Released during Apoptotic and Necroptotic Cell Death. Cell Rep. 2020, 30 (4), 1260-1270.e5.

(22) Samson, A. L.; Zhang, Y.; Geoghegan, N. D.; Gavin, X. J.; Davies, K. A.; Mlodzianoski, M. J.; Whitehead, L. W.; Frank, D.; Garnish, S. E.; Fitzgibbon, C.; Hempel, A.; Young, S. N.; Jacobsen, A. V.; Cawthorne, W.; Petrie, E. J.; Faux, M. C.; Shield-Artin, K.; Lalaoui, N.; Hildebrand, J. M.; Silke, J.; Rogers, K. L.; Lessene, G.; Hawkins, E. D.; Murphy, J. M. MLKL Trafficking and Accumulation at the Plasma Membrane Control the Kinetics and Threshold for Necroptosis. Nat. Commun. 2020, 11 (1), 3151.

(23) Reddy, A.; Caler, E. V.; Andrews, N. W. Plasma Membrane Repair Is Mediated by Ca2+-Regulated Exocytosis of Lysosomes. Cell 2001, 106 (2), 157-169.

(24) Metabolites released from apoptotic cells act as tissue messengers | Nature.

(25) Proteomic analysis of necroptotic extracellular vesicles | bioRxiv.

(26) Exosomes Induce Fibroblast Differentiation into Cancer-Associated Fibroblasts through TGFβ Signaling | Molecular Cancer Research.

(27) Ostrowski, M.; Carmo, N. B.; Krumeich, S.; Fanget, I.; Raposo, G.; Savina, A.; Moita, C. F.; Schauer, K.; Hume, A. N.; Freitas, R. P.; Goud, B.; Benaroch, P.; Hacohen, N.; Fukuda, M.; Desnos, C.; Seabra, M. C.; Darchen, F.; Amigorena, S.; Moita, L. F.; Thery, C. Rab27a and Rab27b Control Different Steps of the Exosome Secretion Pathway. Nat. Cell Biol. 2010, 12 (1), 19-30.

(28) Chen, W.; Zhou, Z.; Li, L.; Zhong, C. Q.; Zheng, X.; Wu, X.; Zhang, Y.; Ma, H.; Huang, D.; Li, W.; Xia, Z.; Han, J. Diverse Sequence Determinants Control Human and Mouse Receptor Interacting Protein 3 (RIP3) and Mixed Lineage Kinase Domain-like (MLKL) Interaction in Necroptotic Signaling. J. Biol. Chem. 2013, 288 (23), 16247-16261.

(29) Orozco, S.; Yatim, N.; Werner, M. R.; Tran, H.; Gunja, S. Y.; Tait, S. W.; Albert, M. L.; Green, D. R.; Oberst, A.

RIPK1 Both Positively and Negatively Regulates RIPK3 Oligomerization and Necroptosis. Cell Death Differ. 2014, 21 (10), 1511-1521.

(30) Huynh, C.; Andrews, N. W. The Small Chemical Vacuolin-1 Alters the Morphology of Lysosomes without Inhibiting Ca2+-Regulated Exocytosis. EMBO Rep. 2005, 6 (9), 843-847.

Example 4—Material and Methods Used in Example 3

Cell Culture. Mouse embryonic fibroblasts (MEFs) were isolated from E12.5 littermate Ripk3+/+ or Ripk3−/− mice. HT29 cells were obtained from American Type Culture Center. All cells were cultured in DMEM medium (4.5 g/L glucose) under 10% FBS and 1% penicillin-streptomycin in a humidified chamber at 37° C. under 5% CO2. Media was changed every 2-3 days and cells were passaged using 0.05% trypsin. EV-depleted FBS (System Biosciences) was used for cells whoseSEVs were used in experiments.

Cell-Death Induction. For induction of necroptosis, MEFs were pre-treated with 10 μM BV6 (Smac mimetic) and 20 μM zVAD-fmk (hereafter zVAD) for 1 hour. Recombinant mouse TNFα (50 ng/ml, R&D systems) was added for 6 hours. HT29 cells were pre-treated with 10 μM BV6 and/or 20 μM zVAD for 1 hour. Recombinant human TNFα (30 ng/mL) was added for 4 hours. Cell death was evaluated using Annexin V/7-AAD (BD Biosciences) coupled with flow-cytometry.

Extracellular Vesicle (EV) Isolation from Cells. Differential centrifugation was also used for SEV isolation. Briefly, conditioned media or plasma was spun at 800 g for 10 min to remove cells and large cell debris. The supernatant was transferred and spun at 10,000×g for 30 min at 4° C. The supernatant was carefully harvested and centrifugation was performed at 100,000×g at 4°C for 90 minutes. The supernatant was discarded and the pellet was dissolved in PBS. SEVs were isolated from human and mouse plasma using ExoQuick Ultra (System Biosciences) according to the manufacturer's instructions. Differential centrifugation was also used for SEV isolation. Briefly, plasma was spun at 10,000×g for 1 hour at 4° C. The supernatant was carefully harvested and centrifugation was performed at 100,000×g at 4° C. for 90 minutes. The supernatant was discarded and the pellet was dissolved in PBS.

For size exclusion chromatography, qEVoriginal/35 nm Gen 2 Column (IZON Science LTD, MA) were used as per manufacturer's instructions. Briefly, conditioned media was pre-cleared using step-wise centrifugation described above. An enrichment of EVs (along with any putative protein contaminants) was performed using ultracentrifugation and resuspension in 500 μL of PBS. Next, to separate any putative protein contaminants from EVs, size exclusion chromatography was performed. The fraction corresponding to EVs (expected to be separated from protein contaminants) was collected in 1.5 mL PBS. Because the amount of EVs collected after SEC was low, a concentrating step was added and EVs were resuspended in a final volume of 100 μL.

Extracellular Vesicle (EV) Isolation from Human and Mouse Plasma. Mouse blood was collected from 8-12-week-old mice via inferior vena cava (IVC) puncture and supplemented with 3.2% sodium citrate as an anticoagulant (9:1). Blood samples were centrifuged at 1,000×g for 10 minutes at 4° C. The supernatant was collected and spun at 10,000×g for 20 minutes at 4° C. to remove residual platelets. EVs were isolated from human and mouse plasma using ExoQuick Ultra (System Biosciences) according to manufacturer's instructions. Prior to EV isolation from plasma, plasma samples were treated with PureProteome Albumin/IgG Depletion kit (Millipore Sigma, LSKMAGD12) according to manufacturer's instructions. Differential centrifugation was also used for EV isolation. Briefly, plasma was spun at 10,000×g for 1 hour at 4° C. The supernatant was carefully harvested and centrifugation was performed at 100,000×g at 4°C for 90 minutes. The supernatant was discarded and the pellet was dissolved in PBS.

Nanoparticle Tracking Analysis (NTA). The size distribution and particle concentration of the isolated EVs were measured using a Nanosight NS300 equipped with Nanosight NTA 3.3 software and a 532 nm laser (Malvern Instruments, UK). 3 videos of 60 s each were recorded for all EV samples at camera level 15 and syringe pump speed of 70. The analysis was done at 25 frames/sec with a detection threshold of 4. All samples were diluted to the appropriate concentration in PBS prior to measurement.

Mass Spectrometry. Isolate exosomes in 225 μL of ammonium bicarbonate (ABC) pH 7 were lysed with 25 μL of the solubilization buffer consisting of 0.5% 4-hexylphenylazosulfonate (final surfactant concentration, 0.05%). Samples were then reduced using 4 μL of 100 mM TCEP and alkylated with 4 μL of 500 mM 2-chloroacetamide solution and incubated at room temperature for 30 min. Proteins were digested using 2 μL of 0.3 μg/μL Trypsin solution and incubated at 37° C. for 1 h. The surfactant was degraded with 5 min of UV. 2 μL of 10% TFA was added to samples, which were then vortexed and centrifuged at 20,000 g for 2 min. The surfactant was degraded with 5 min of UV irradiation using a 100 W mercury lamp (Nikon housing with Nikon HB-10101AF power supply; handle with caution). The sample was reconstituted in 25 L of mobile phase solvent A (99.8% water and 0.2% formic acid). The peptide concentration was determined using NanoDrop operating at 280 nm.

Approximately 200 ng of peptide were loaded onto an Ion Optics column (25 cm×75 μm, C18 1.6 μm) heated to 55° C. The separation was performed using the following gradient: 0-60 min 2-17% B, 60-90 min 17-25% B, 90-100 min 37% B, 100-110 min 37-85% B, and 110-120 min 85% B using a flow rate of 400 nL/min and mobile phase B consisting of 99.8% ACN and 0.2% formic acid. Eluting peptides were directly ionized via electrospray ionization (CaptiveSpray) using a capillary voltage of 1500V, dry gas of 3.0 l/min, and dry temp of 180° C. Ions measured from 100-1700 m/z using a timsTOF Pro Q-TOF (Bruker Daltonics) operating in PASEF mode (PMC6283298) with an ion mobility range (1/k0) of 0.60 to 1.60 Vs/cm$^2$.

For tandem MS, the following parameters were used: number of PASEF MS/MS scans (10); total cycle time (1.16 s); target intensity (20000); intensity threshold (2500); charge range (0-5); active exclusion on, release after 0.4 min, reconsider if current intensity 4× previous; isolation width (2 m/z for m/z<700 and 3 m/z for m/z>700); collisional energy (20-59 eV). The performance of the instrument (as well as validation of the peptide loading amount) was monitored periodically by running 200 ng of standard K652 digestion (Promega). Data were processed using MaxQuant V1.6.17.0 software (PMC7261821).

For searches, the reviewed *Mus musculus* (Mouse) UniProt sequences were used using a 1% false discovery rate. All searches were performed with carbamidomethyl (C) has a fixed modification and oxidation (M), protein N-terminal acetylation, and phosphorylation (STY) set as variable modifications. Match between runs was enabled. Otherwise, the MaxQuant parameters were not changed from their default values.

For the co-IPs samples were precipitated in 500 μL acetone overnight. After centrifugation (20,000 g, 10 minutes, 4° C.), 30 μL of ABC was added to each along with 10 mM TCEP, 20 mM CA, and 1 μg trypsin. Samples were digested overnight at 4° C. 2 μL of TFA (10%) was added to quench the digestion. Data were processed using MSFragger V15 (see Kong et al., Nat Methods 14, 513-520 (2017)). For searches, the reviewed *Mus musculus* (Mouse) UniProt sequences were used using a 1% false discovery rate. All searches were performed with carbamidomethyl (C) has a fixed modification and oxidation (M), protein N-terminal acetylation, and phosphorylation (STY) set as variable modifications. Match between run was enabled. Otherwise, the MSFragger parameters were not changed from their default values. The data were deposited to the ProteomeXchange Consortium via the PRIDE (PMC6323896) partner repository with the dataset identifier PXD.

Electron Microscopy (EM). Isolated SEVs were fixed with 2% paraformaldehyde, adhered to a carbon-grid for 20 minutes, and analyzed by transmission electron microscopy after 8 washes and embedded in 2% methylcellulose with 0.4% uranyl acetate.

Proteinase-K Digestion of SEVs. EVs isolated from MEFs treated with TNFα, Smac-mimetic, and zVAD (TSZ) via ExoQuick were resuspended in Dulbecco's phosphate-buffered saline. The mix was incubated at 37° C. with or without Triton X-100 (1% v/v) where indicated. For proteinase K digestion, SEVs were treated with $10^{-5}$ units/mL proteinase K (New England BioLabs, Cat #: P8107S), Triton X-100 (1% v/v), and 15 mm $CaCl_2$). The presence of RIPK3 was then detected via Western blotting.

Example 5—Rapid Exosome Proteomics Enabled by Azo and TimsTOF Pro

Exosomes are extracellular nanovesicles between 30 and 150 nm in diameter. The proteomic contents of these vesicles have potential for detection and as therapeutics for pathologies such as cancer and cardiovascular disease. Bottom-up mass spectrometry (MS)-based proteomics represents a powerful tool for detecting potential proteomic biomarkers in exosomes. Traditional bottom-up sample preparation results in poor proteome coverage and though more sensitive methods for exosome sample preparation have been developed, these methods rely on lengthy digestions, cleanup steps or offline multidimensional separations, which limit sample throughput. This example describes a dedicated protocol for exosome lysis and protein extraction combined with trapped ion mobility (TIMS)-LC-MS/MS analysis separation for a rapid, sensitive, and quantitative approach to exosome proteomics. This method was applied to study protein expression differences between wild-type and alpha-5 integrin knockdown mammary fibroblast exosomes.

Following isolation and purification, the photocleavable surfactant 4 hexophenylazosulfonate (Azo) at 0.1% was used to lyse and extract proteins from lipid vesicles. Proteins were subsequently reduced, alkylated, and rapidly digested with trypsin. The Azo surfactant was degraded with UV irradiation and removed for TIMS-LC-MS analysis on a timsTOF Pro instrument. Total sample prep time required less than two hours.

Figure 20:
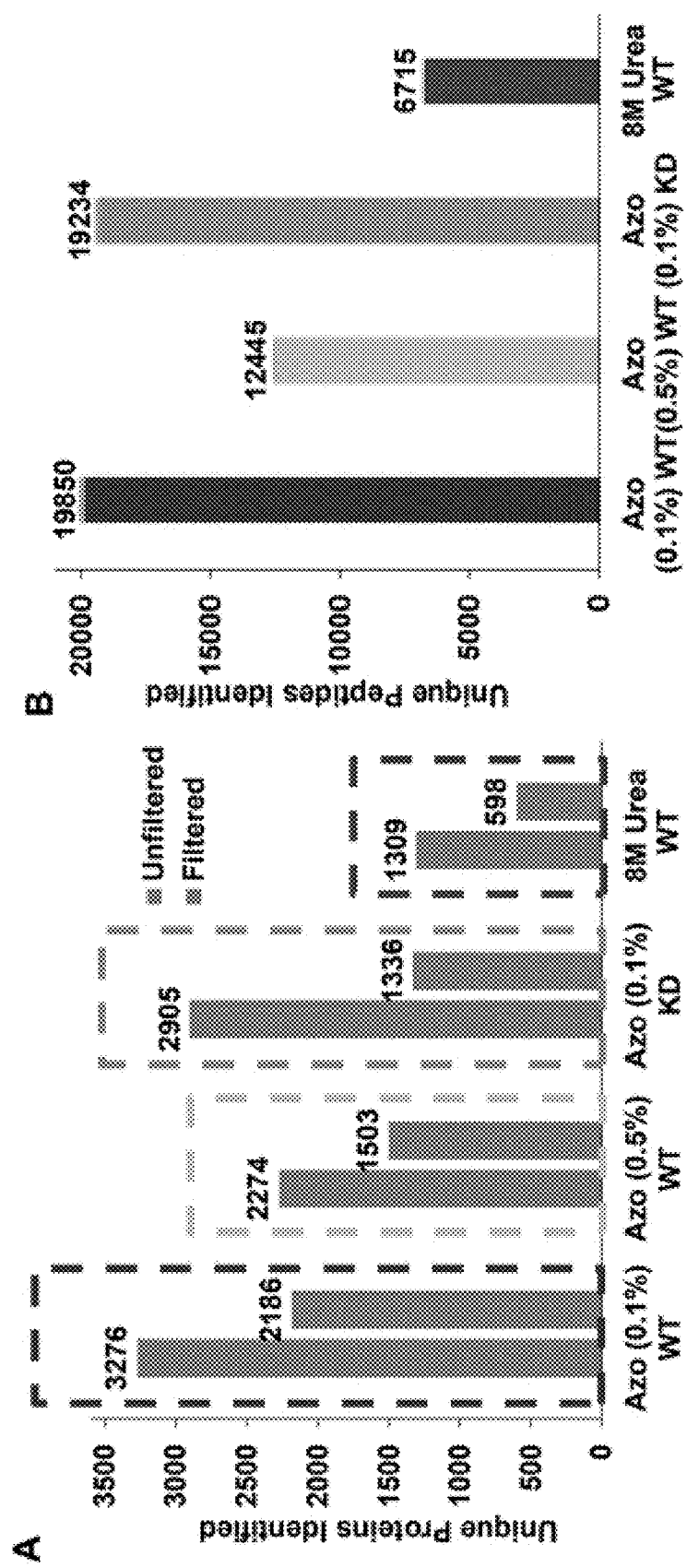
FIG. 20: Panel A) shows absolute numbers of unique protein identifications from several extraction conditions: 0.1% Azo surfactant wild-type (WT) mammary fibroblast exosomes, 0.5% Azo extracted WT exosomes, 0.1% Azo extracted alpha-5 integrin knockdown exosomes, and WT exosome proteins extracted from urea in-solution digests. Bars on the left side of each pair show unprocessed identifications, while bars on the right side of each pair show number of identifications after filtering for valid LFQ intensities in multiple replicates. The optimal concentration of Azo surfactant was determined to be 0.1%. Panel B) shows absolute numbers of unique peptide identifications corresponding to the extraction groups from panel A).
Figure 21:
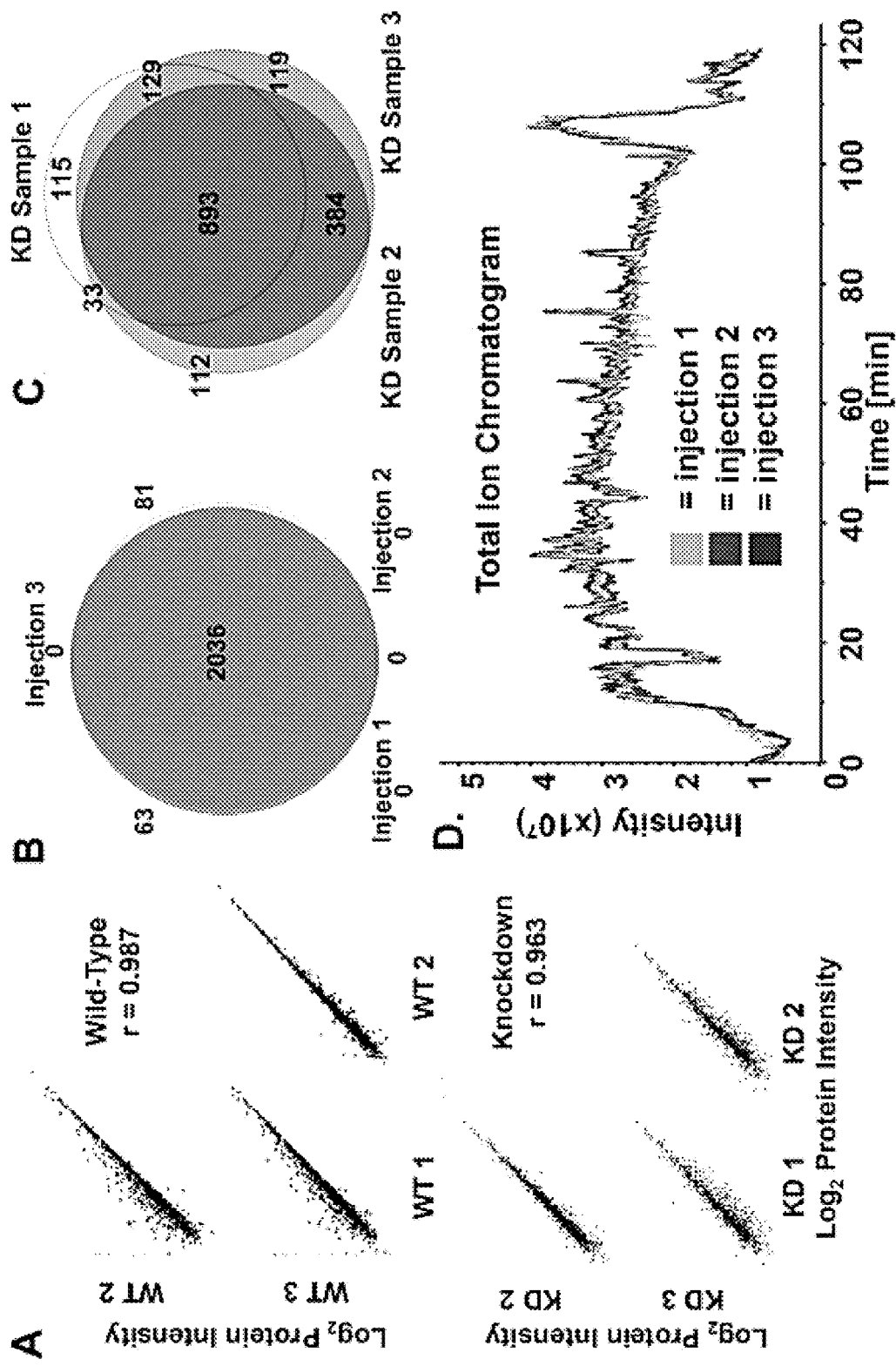
FIG. 21: Panel A) shows Pearson correlation coefficients of wild type (WT) and knockdown (KD) samples, showing strong association across replicates. Panel B) shows proteins identified in injection replicates of WT samples, showing high overlap. Panel C) shows the proteins identified in technical replicates of knockdown samples. Panel D) shows total ion chromatogram of three injection replicates of WT samples, demonstrating reproducible analysis.

FIG. 19 shows the results of NanoSight nanoparticle tracking analysis (NTA) used for the determination of vesicle size and concentration in wild-type exosome samples (top) and alpha-5 integrin knockdown samples (bottom). FWHM vesicle size was 101.3 nm for wild-type exosomes and 104 nm for knockdown exosomes. As seen in FIG. 20, the Azo-based exosome proteomics yielded high numbers of unique protein and peptide identifications. This method was reproducible across multiple replicate experiments (see FIG. 21).

Figure 22:
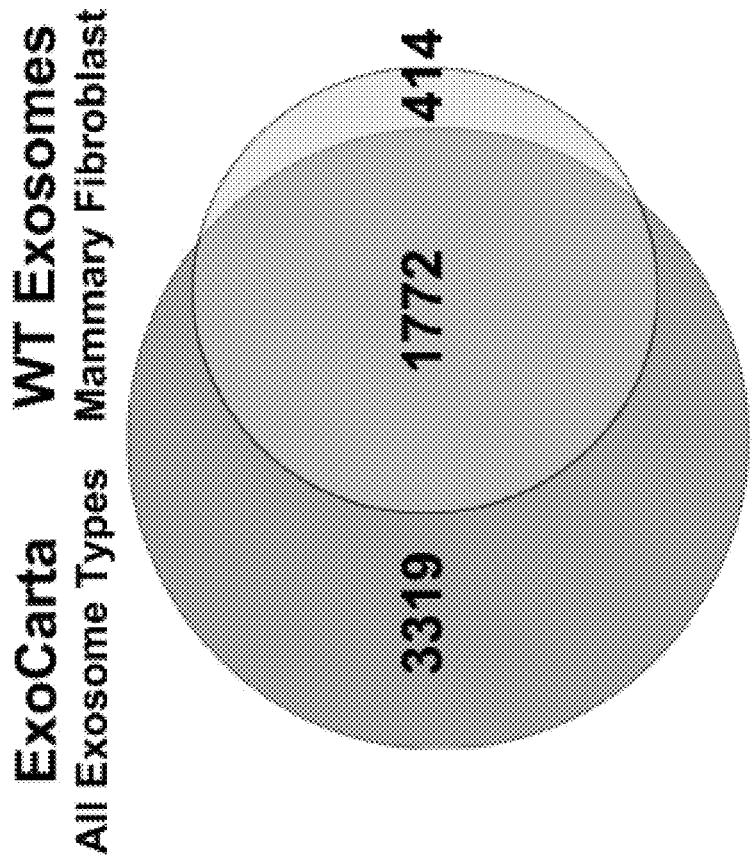
FIG. 22: Overlap between WT sample and all human proteins identified by MS in ExoCarta (left), an exosome-specific database. The table (right) shows nine of the top 100 most commonly identified exosome proteins from ExoCarta and their associated $Log_2$ normalized LFQ intensities, showing they were highly abundant.
Figure 23:
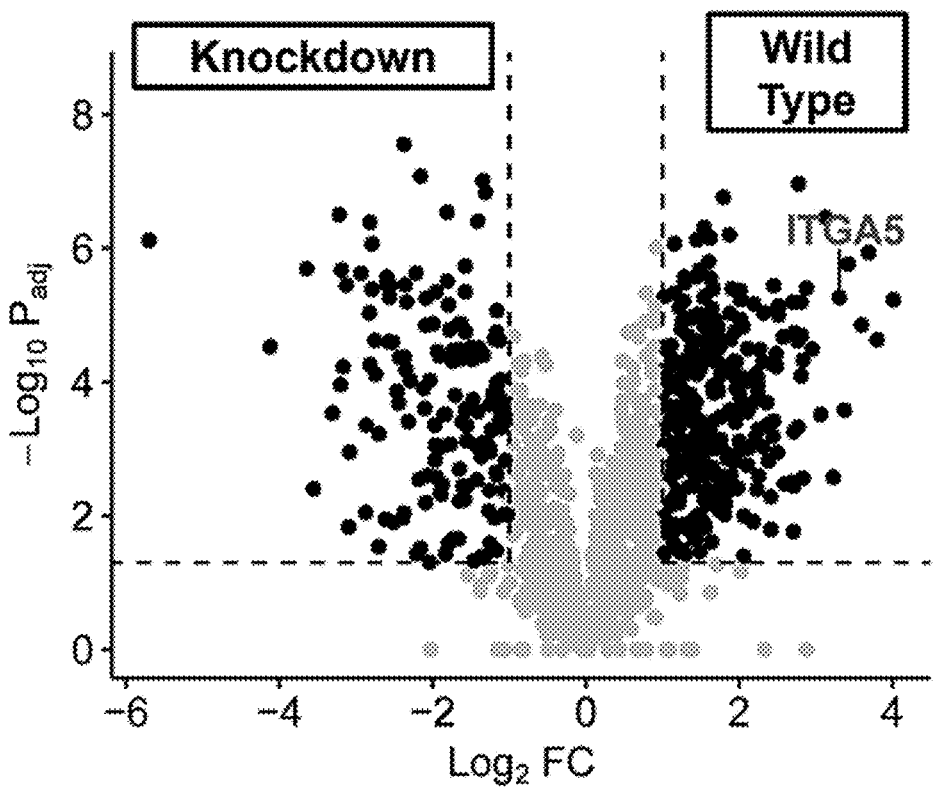
FIG. 23: A volcano plot showing significance of log fold changes in protein expression between WT and ITGA5-KD exosomes. The corresponding table shows a selection of highly differentially-expressed proteins with associated -log (P) values showing significance.
Figure 24:
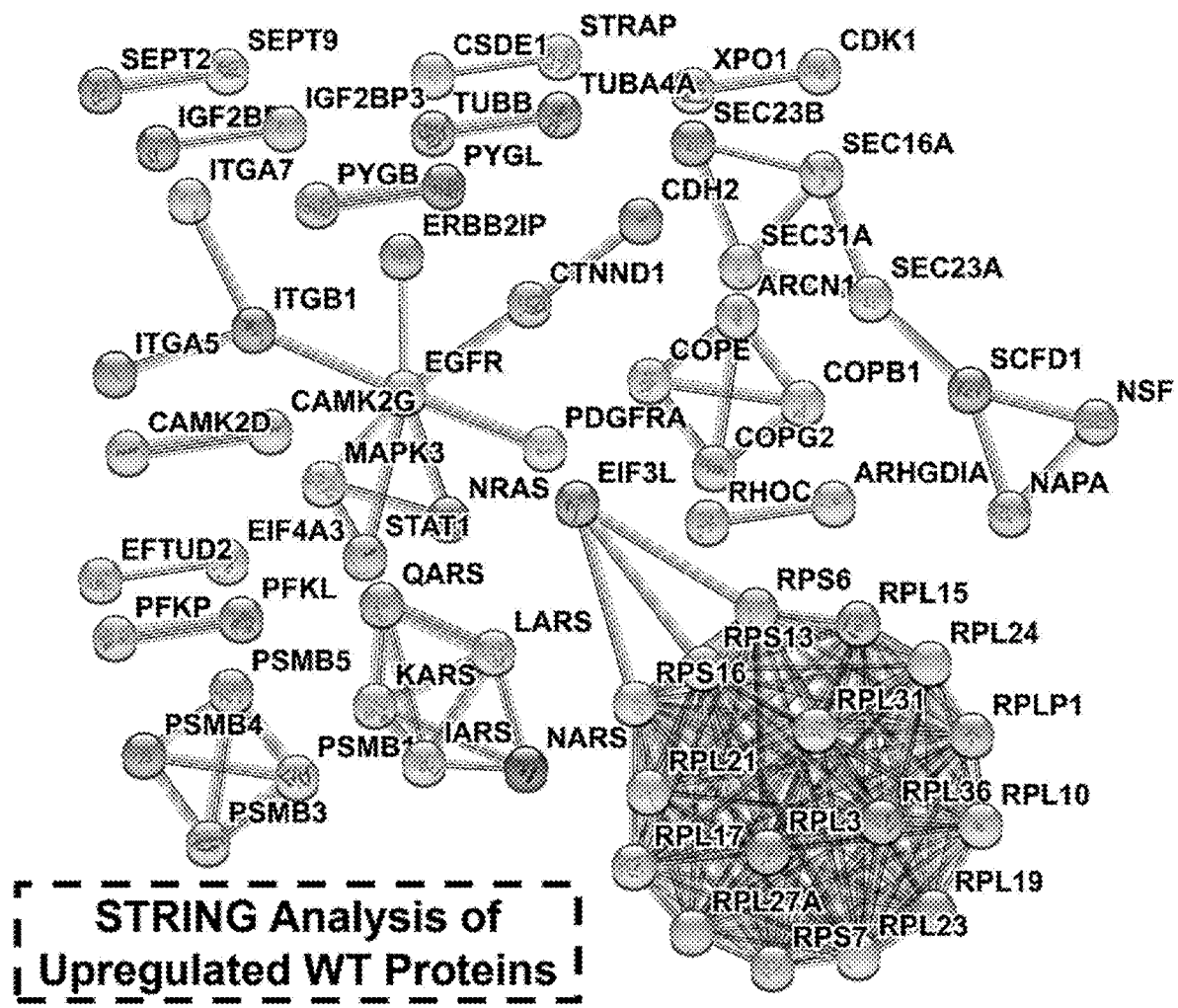
FIG. 24: STRING analysis of significant differentially expressed proteins from the wild type exosome sample. FDR stringency was set to one percent, and minimum interaction confidence required to assign an association was set to 0.95. Interactions included several ribosomal proteins (large cluster), tRNA synthetases, vesicular proteins, proteasomal proteins, and integrins/other proteins in the EGF signaling pathway.

The protein identifications from the mammary fibroblast exosomes showed high overlap with the extracellular vesicle database for all human cell types. FIG. 22 illustrates the overlap between the proteins identified in wild type (WT) exosomes using the method in this experiment and all human proteins identified by MS present in ExoCarta (an exosome-specific database). Furthermore, this experiment was able to successfully identify expression differences between the wild-type and alpha-5 integrin knockdown samples (FIGS. 23 and 24).

In summary, this method was used to characterize the protein content of exosomes and was able to achieve reproducible, deep coverage of the proteome. Use of the photocleavable surfactant Azo in conjunction with PASEF (parallel accumulation-serial fragmentation) on timsTOF Pro enabled greater sensitivity of exosome peptide analysis in a shorter timeframe than conventional techniques. This method was further used to compare protein expression in wild-type and alpha-5 integrin knockdown exosomes and was able to show a large impact on ribosomal proteins and translation-associated genes. Accordingly, this method shows promise for the study of exosomes, including samples obtained from biofluids.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A method for analyzing one or more lipid vesicles comprising the steps of:
   a) contacting the one or more lipid vesicles with a photo-cleavable anionic surfactant in a solution, thereby lysing the one or more lipid vesicles and generating a mixture of dissolved compounds comprising compounds obtained from within the one or more lipid vesicles, wherein the photo-cleavable anionic surfactant comprises: i) a hydrophilic head, ii) a hydrophobic tail, and iii) a photo-cleavable moiety covalently linking the hydrophilic head and hydrophobic tail; and
   b) exposing the solution containing the photo-cleavable anionic surfactant and mixture of dissolved compounds to electromagnetic radiation, thereby decomposing the photo-cleavable moiety and generating an irradiated solution containing the mixture of dissolved compounds, wherein the photo-cleavable anionic surfactant has the formula:

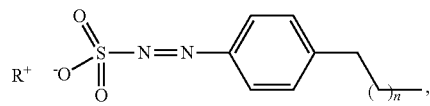

where n is an integer selected from 2 to 30, and R is any atom or molecule able to form a cation.

2. The method of claim 1 wherein the one or more lipid vesicles are one or more extracellular vesicles obtained from one or more cells or samples from a subject.

3. The method of claim 1 wherein the one or more lipid vesicles are one or more exosomes.

4. The method of claim 1, wherein the one or more lipid vesicles have an average diameter between 30 and 150 nm.

5. The method of claim 1 comprising performing mass spectrometry (MS) analysis on a portion of the irradiated solution containing the mixture of dissolved compounds.

6. The method of claim 5 comprising performing a separation step on the irradiated solution prior to performing MS analysis.

7. The method of claim 5 comprising exposing the solution containing the photo-cleavable anionic surfactant and mixture of dissolved compounds to electromagnetic radiation prior to injecting or spraying the irradiated solution in a MS device.

8. The method of claim 5 comprising exposing the solution containing the photo-cleavable anionic surfactant and mixture of dissolved compounds to electromagnetic radiation after injecting or spraying the solution in a MS device, wherein the electromagnetic radiation is provided by the MS device.

9. The method of claim 8 wherein the electromagnetic radiation is provided during ultraviolet photo-dissociation.

10. The method of claim 1, wherein the mixture of dissolved compounds comprises nucleic acids, lipids, saccharides, proteins, protein fragments, and combinations thereof.

11. The method of claim 1, wherein the mixture of dissolved compounds comprises one or more proteins or protein fragments.

12. The method of claim 10, wherein the proteins are part of pathways involved with tumorigenesis, metastasis, cardiac regeneration, necroptosis or apoptosis.

13. The method of claim 1, wherein R is calcium, sodium, potassium, or combinations thereof.

14. The method of claim 1, wherein the photo-cleavable anionic surfactant comprises 4-hexylphenylazosulfonate.

15. The method of claim 1, wherein the photo-cleavable anionic surfactant remains stable at a pH of 4 or lower.

16. The method of claim 1 comprising exposing the solution containing the photo-cleavable surfactant and mixture of dissolved compounds to ultraviolet (UV) light.

17. The method of claim 16, wherein the UV light has a wavelength between 250-350 nm.

* * * * *